United States Patent
Guo et al.

(10) Patent No.: US 11,903,924 B2
(45) Date of Patent: Feb. 20, 2024

(54) HBV INHIBITOR AND ITS USE

(71) Applicant: XI'AN XINTONG PHARMACEUTICAL RESEARCH CO., LTD., Shaanxi (CN)

(72) Inventors: Weibo Guo, Shaanxi (CN); Dengke Zhang, Shaanxi (CN); Weili Jin, Shaanxi (CN); Mingzhe Ji, Shaanxi (CN); Yanxia Zhang

(73) Assignee: Xi'an Xintong Pharmaceutical Research Co., Ltd., Shaanxi (CN)

( * ) Notice: Subject to any disclaimer, the term of this patent is extended or adjusted under 35 U.S.C. 154(b) by 33 days.

(21) Appl. No.: 17/593,632

(22) PCT Filed: Jan. 20, 2020

(86) PCT No.: PCT/CN2020/073160
§ 371 (c)(1),
(2) Date: Sep. 22, 2021

(87) PCT Pub. No.: WO2021/093172
PCT Pub. Date: May 20, 2021

(65) Prior Publication Data
US 2022/0184035 A1    Jun. 16, 2022

(30) Foreign Application Priority Data

Nov. 13, 2019  (CN) .......................... 201911103300.1
Nov. 22, 2019  (CN) .......................... 201911154337.7

(51) Int. Cl.
| | |
|---|---|
| A61K 31/4025 | (2006.01) |
| A61P 31/20 | (2006.01) |
| A61K 31/341 | (2006.01) |
| A61K 31/381 | (2006.01) |
| A61K 31/404 | (2006.01) |
| A61K 31/4178 | (2006.01) |
| A61K 31/4184 | (2006.01) |
| A61K 31/4192 | (2006.01) |
| A61K 31/42 | (2006.01) |
| A61K 31/421 | (2006.01) |
| A61K 31/423 | (2006.01) |
| A61K 31/427 | (2006.01) |
| A61K 31/428 | (2006.01) |
| A61K 31/4709 | (2006.01) |
| A61K 31/498 | (2006.01) |
| A61K 31/513 | (2006.01) |
| A61K 31/522 | (2006.01) |
| A61K 31/536 | (2006.01) |
| A61K 31/675 | (2006.01) |
| A61K 31/7056 | (2006.01) |
| C07D 263/34 | (2006.01) |
| C07D 277/56 | (2006.01) |
| C07D 307/68 | (2006.01) |
| C07D 333/38 | (2006.01) |
| C07D 405/12 | (2006.01) |
| C07D 405/14 | (2006.01) |
| C07D 407/12 | (2006.01) |
| C07D 409/12 | (2006.01) |

(Continued)

(52) U.S. Cl.
CPC ........ *A61K 31/4025* (2013.01); *A61K 31/341* (2013.01); *A61K 31/381* (2013.01); *A61K 31/404* (2013.01); *A61K 31/4178* (2013.01); *A61K 31/4184* (2013.01); *A61K 31/4192* (2013.01); *A61K 31/42* (2013.01); *A61K 31/421* (2013.01); *A61K 31/423* (2013.01); *A61K 31/427* (2013.01); *A61K 31/428* (2013.01); *A61K 31/4709* (2013.01); *A61K 31/498* (2013.01); *A61K 31/513* (2013.01); *A61K 31/522* (2013.01); *A61K 31/536* (2013.01); *A61K 31/675* (2013.01); *A61K 31/7056* (2013.01); *A61P 31/20* (2018.01); *C07D 263/34* (2013.01); *C07D 277/56* (2013.01); *C07D 307/68* (2013.01); *C07D 333/38* (2013.01); *C07D 405/12* (2013.01); *C07D 405/14* (2013.01); *C07D 407/12* (2013.01); *C07D 409/12* (2013.01); *C07D 409/14* (2013.01); *C07D 417/12* (2013.01); *C07D 417/14* (2013.01)

(58) Field of Classification Search
CPC . A61K 31/341; A61K 31/381; A61K 31/4025
See application file for complete search history.

(56) References Cited

U.S. PATENT DOCUMENTS

| | | |
|---|---|---|
| 10,450,270 B2 | 10/2019 | Vandyck et al. |
| 2018/0161307 A1 | 6/2018 | Du et al. |
| 2019/0241514 A1 | 8/2019 | Schinazi et al. |

FOREIGN PATENT DOCUMENTS

| | | |
|---|---|---|
| CN | 108047115 A | 5/2018 |
| CN | 108250122 A | 7/2018 |

(Continued)

OTHER PUBLICATIONS

International Search Report (PCT/ISA/210) with an English translation, and Written Opinion (PCT/ISA/237) dated Aug. 20, 2020, by the China National Intellectual Property Administration as the International Searching Authority for International Application No. PCT/CN2020/073160.

*Primary Examiner* — Marcos L Sznaidman
(74) *Attorney, Agent, or Firm* — BUCHANAN, INGERSOLL & ROONEY PC

(57) ABSTRACT

The present invention provides anti-HBV compounds, pharmaceutically acceptable compounds or stereoisomers thereof, and preparation methods and uses for treating, eradicating or inhibiting HBV infection or for alleviating liver injury caused by HBV infection, and so on.

10 Claims, 1 Drawing Sheet

(51) Int. Cl.
 *C07D 409/14* (2006.01)
 *C07D 417/12* (2006.01)
 *C07D 417/14* (2006.01)

(56) References Cited

FOREIGN PATENT DOCUMENTS

| | | |
|---|---|---|
| CN | 109153640 A | 1/2019 |
| CN | 109790168 A | 5/2019 |
| WO | 2015011281 A1 | 1/2015 |
| WO | 2017156255 A1 | 9/2017 |
| WO | 2018039531 A1 | 3/2018 |
| WO | 2018121689 A1 | 7/2018 |
| WO | 2019118358 A1 | 6/2019 |
| WO | 2019154343 A1 | 8/2019 |
| WO | 2019165374 A1 | 8/2019 |
| WO | 2019185016 A1 | 10/2019 |

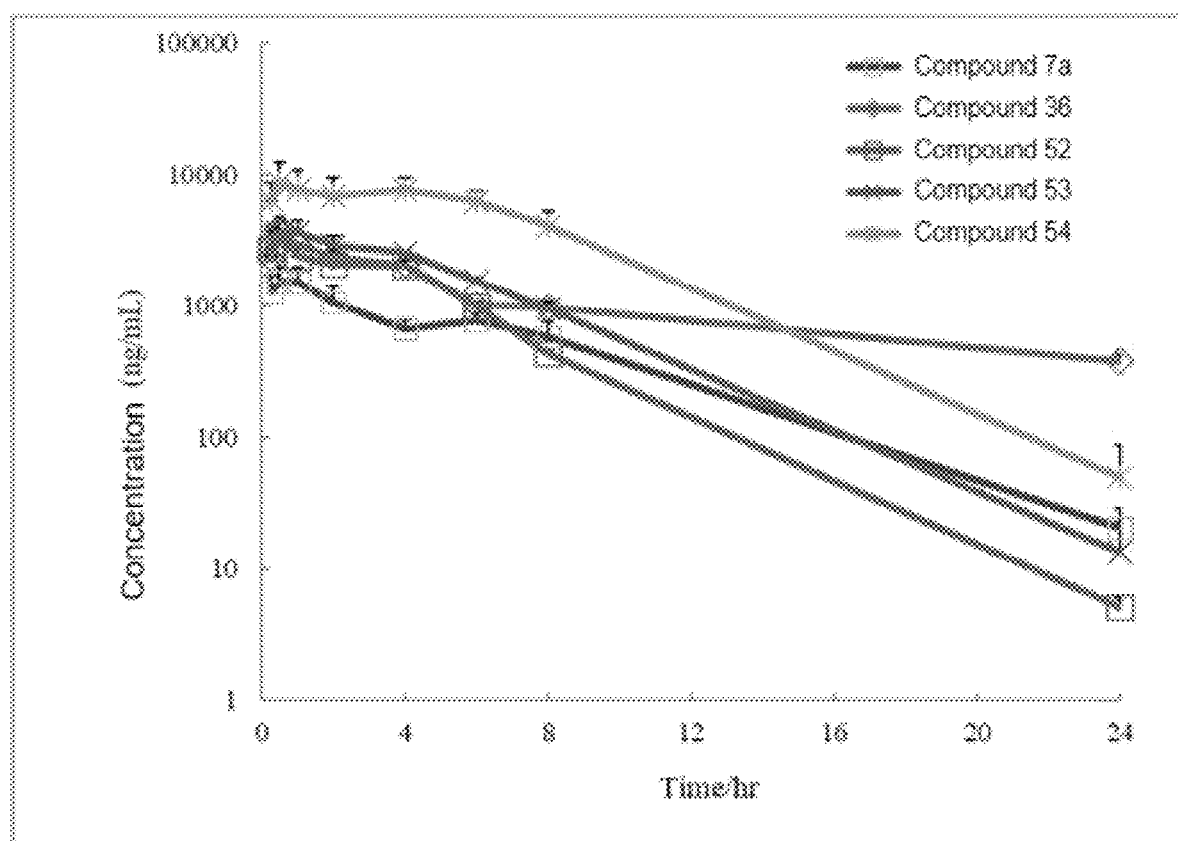

HBV INHIBITOR AND ITS USE

TECHNICAL FIELD

This application involves antiviral compounds. Specifically, the present invention is related to anti-HBV compounds and their pharmaceutically acceptable compounds or stereoisomers thereof, as well as methods for their preparation and their use in the treatment, eradication or inhibition of HBV infection or in alleviating the liver injury as caused by HBV infection, etc.

BACKGROUND TECHNIQUES

Chronic hepatitis B (as abbreviated as CHB) is a major "killer" of human health. It is a disease caused by hepatitis B virus (HBV), which is mainly caused by liver inflammatory lesions and can cause injury to multiple organs. Hepatitis B virus is a DNA virus, which belongs to the family of hepadnaviridae. Hepatitis B is widespread in countries around the world. About 250 million people worldwide are infected with hepatitis B virus, which mainly affects children and young adults. A considerable number of patients can later transform into liver cirrhosis or liver cancer (patients). Therefore, it has become a worldwide disease that seriously threatens human health.

The anti-hepatitis B virus nucleoside (acid) drugs currently on the market include Lamivudine, Telbivudine, Entecavir, Tenofovir Disoproxil, and Clavudine. There are many shortcomings of this kind of drugs, such as irregular course of treatment, prone to viral resistance, and likely relapse after stopping the administration.

In addition, during the replication process of hepatitis B virus, the viral DNA enters the host cell nucleus. Under the action of DNA polymerase, the gaps in the two strands are filled to form a superspiral covalent, closed and circular DNA molecule (covalently closed circular DNA, or cccDNA). Extracellular hepatitis B virus DNA is a relaxed circular double-stranded DNA (or relaxed circular DNA, aka rcDNA) molecule. cccDNA is the original template for the replication of hepatitis B virus' pre-genomic RNA. Although its content is small, there are only about 5-50 copies in each liver cell, it has very important meaning for the replication of hepatitis B virus and the establishment of infection status.

The virus carrying state of hepatitis B patients can be completely eliminated only if the cccDNA in the nucleus can be thoroughly eradicated, which is the goal of antiviral therapy.

Unlike polymerase target nucleoside drugs, capsid protein target inhibitors can reduce the latent form of hepatitis B virus, namely cccDNA. At present, there have been some reports on capsid protein target inhibitor targets. For example, patents WO 2015/011281, WO 2017/156255, WO 2018/039531, WO 2018/121689, WO 2019/165374, WO 2019/154343, WO 2019/118358 and WO 2019/185016 reported some capsid protein target inhibitors.

However, the inhibitory activity and cytotoxicity related to drug safety reported in the prior arts are mixed, and it is difficult to predict the structural formula of a compound with a good drug effect. Based on long-term research experience, the inventors have obtained a series of new anti-HBV compounds. It is particularly surprising that many of the compounds with non-obvious structures have excellent effects and have promising pharmaceutical prospects.

SUMMARY OF THE INVENTION

The present invention provides a compound represented by general formula I or general formula II, or its pharmaceutically acceptable salt or tautomer or enantiomer or diastereomer:

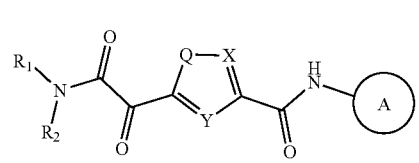

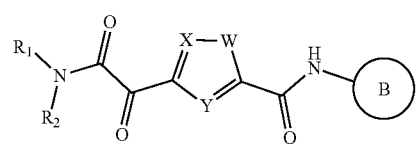

in which:

X is selected from N or $CR_3$;

Y is selected from N or $CR_4$;

Q is selected from O, S;

W is selected from O, S, $NR_5$;

$R_1$ is selected from: H, $C_1$-$C_6$ alkyl, $C_2$-$C_6$ alkenyl, and $C_2$-$C_6$ alkynyl;

$R_2$ is selected from $C_1$-$C_6$ alkyl, $C_2$-$C_6$ alkenyl, $C_2$-$C_6$ alkynyl, $C_3$-$C_8$ cycloalkyl, $C_3$-$C_8$ saturated or unsaturated heterocyclic ring containing N, O, S heteroatoms, and/or aryl;

wherein each occurrence of $R_2$ is optionally substituted with one or more substituents selected from the below groups consisting of halogen, hydroxy, $C_1$-$C_6$ alkyl, $C_2$-$C_6$ alkenyl, $C_2$-$C_6$ alkynyl, $C_3$-$C_8$ Cycloalkyl, $C_1$-$C_6$ alkyl substituted by $C_1$-$C_3$ alkoxy, $C_3$-$C_8$ saturated or unsaturated heterocyclic ring containing N, O, S heteroatoms, aryl, $CF_3$, —OR, —$N(R)_2$, —SR, —C(O)OR, —C(O)N(R)$_2$, —C(O)R, —S(O)R, —S(O)$_2$R, —S(O)$_2$N (R)$_2$, and —N(R)C(O)R;

$R_3$ and $R_4$ are each independently selected from: H, halogen, $C_1$-$C_6$ alkyl, $C_2$-$C_6$ alkenyl, $C_2$-$C_6$ alkynyl, $C_3$-$C_8$ cycloalkyl, and halogen-substituted $C_1$-$C_6$ alkyl;

$R_5$ is selected from: H, $C_1$-$C_6$ alkyl, $C_2$-$C_6$ alkenyl, $C_2$-$C_6$ alkynyl, $C_3$-$C_8$ cycloalkyl, hydroxy substituted $C_1$-$C_6$ alkyl, $C_1$-$C_3$ alkoxy substituted $C_1$-$C_6$ alkyl, $C_1$-$C_6$ alkyl substituted by halogen, —C(O)OR, —C(O)N(R)$_2$, —C(O)R, —S(O)R, —S(O)$_2$R, and —S(O)$_2$N (R)$_2$; wherein, when B is a monocyclic ring, R5 is not H, $C_1$-$C_6$ alkyl, $C_2$-$C_6$ alkenyl, or $C_2$-$C_6$ alkynyl; R is selected from: H, $C_1$-$C_6$ alkyl, $C_2$-$C_6$ alkenyl, $C_2$-$C_6$ alkynyl, $C_3$-$C_8$ cycloalkyl, halogen substituted $C_1$-$C_6$ alkyl, hydroxy substituted $C_1$-$C_6$ alkyl, and $C_1$-$C_6$ alkyl substituted with $C_1$-$C_3$ alkoxy;

ring A and Ring B are each independently selected from 5-12 membered substituted or unsubstituted monocyclic or bicyclic fused rings, the monocyclic or bicyclic fused ring is a saturated monocyclic or bicyclic fused ring, a partially unsaturated monocyclic ring or a bicyclic ring or an aromatic monocyclic or bicyclic ring, and the ring carbon atoms on the monocyclic or bicyclic ring are substituted with 0 to 5 heteroatoms, and the heteroatom refers to O, N or S.

In the first aspect, a novel structural anti-hepatitis B virus (HBV) inhibitor compound or its pharmaceutically acceptable salt or stereoisomer thereof, which is characterized in that ring A or ring B is each independently selected from:

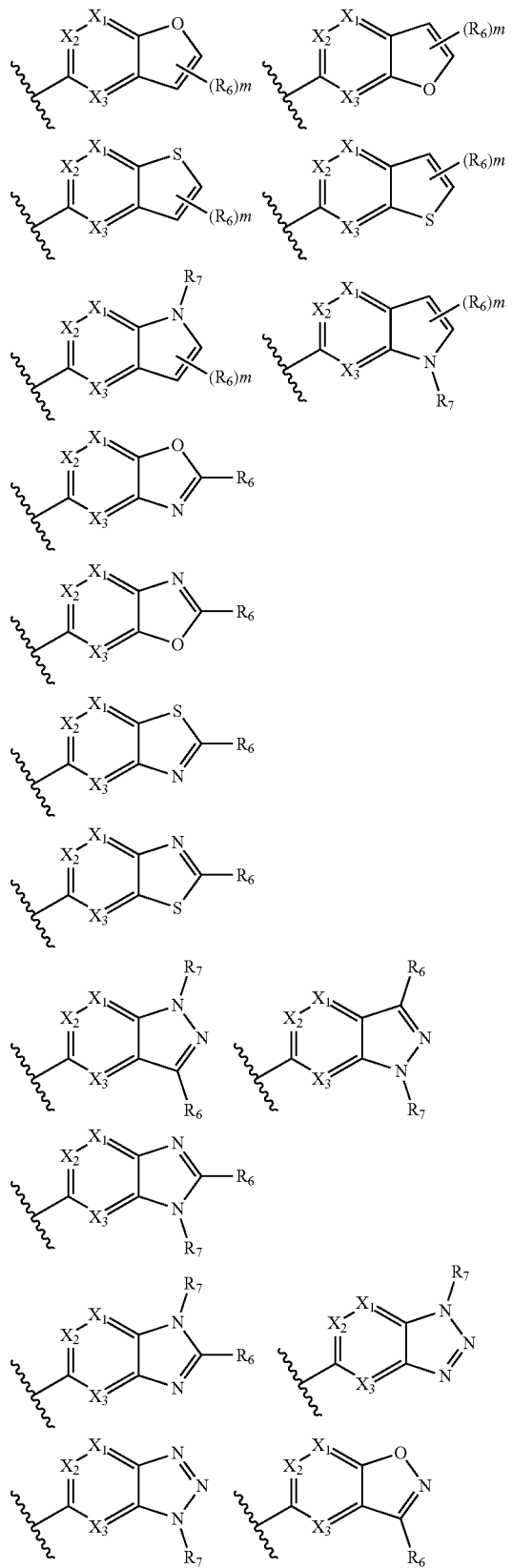

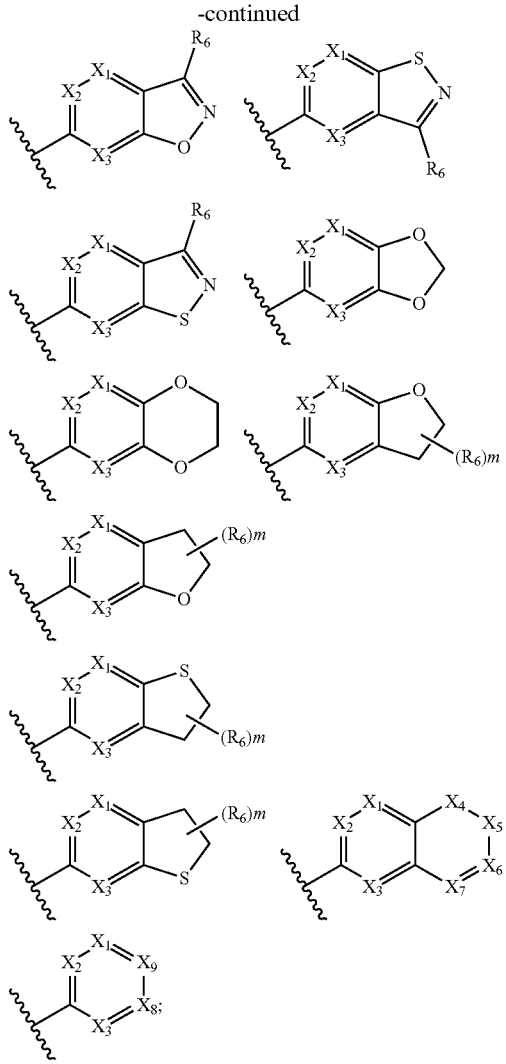

in which:

m is selected from 0, 1 or 2;

$X_1$, $X_2$, $X_3$, $X_4$, $X_5$, $X_6$, $X_7$, $X_8$, $X_9$ are independently selected from: $CR_6$ or N;

$R_6$ is selected from: H, halogen, $C_1$-$C_6$ alkyl, $C_2$-$C_6$ alkenyl, $C_2$-$C_6$ alkynyl, $C_3$-$C_8$ cycloalkyl, halogen-substituted $C_1$-$C_6$ alkyl, hydroxy-substituted $C_1$-$C_6$ alkyl, Alkoxy substituted $C_1$-$C_6$ alkyl, aryl, heteroaryl, nitro, cyano, —OR, —N(R)$_2$, —SR, —C(O)OR, —C(O)N(R)$_2$, —C(O)R, —S(O)R, —S(O)$_2$R, —S(O)$_2$N(R)$_2$, and/or —N(R)C(O)R;

R7 is selected from: H, $C_1$-$C_6$ alkyl, $C_2$-$C_6$ alkenyl, $C_2$-$C_6$ alkynyl, $C_3$-$C_8$ cycloalkyl, halogen-substituted $C_1$-$C_6$ alkyl, hydroxy-substituted $C_1$-$C_6$ alkyl, and $C_1$-$C_6$ alkyl substituted with alkoxy;

each R is independently selected from: H, $C_1$-$C_6$ alkyl, $C_2$-$C_6$ alkenyl, $C_2$-$C_6$ alkynyl, $C_3$-$C_8$ cycloalkyl, halogen-substituted $C_1$-$C_6$ alkyl, hydroxy-substituted $C_1$-$C_6$ alkane Group, and $C_1$-$C_6$ alkyl substituted by alkoxy.

A novel structural anti-hepatitis B virus (HBV) inhibitor compound or its pharmaceutically acceptable salt or stereoisomer thereof, which is characterized in that ring A or ring B is independently selected from:

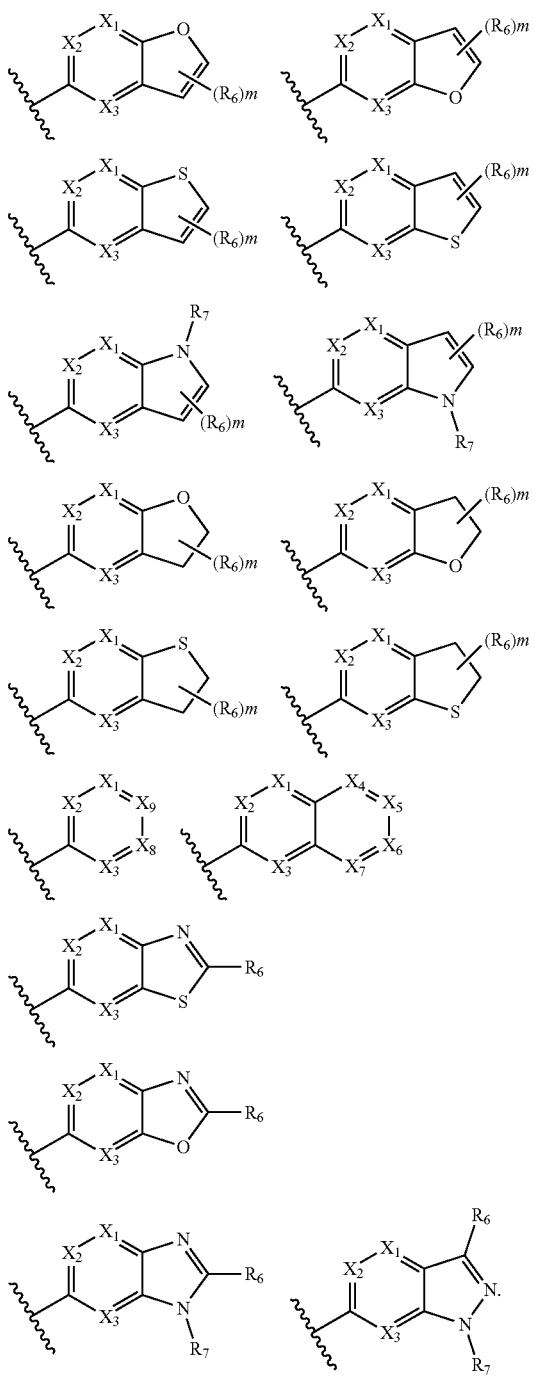

A novel structural anti-hepatitis B virus (HBV) inhibitor compound or its pharmaceutically acceptable salt or stereoisomer thereof, which is characterized in that ring A or ring B is independently selected from:

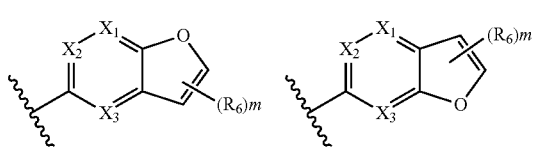

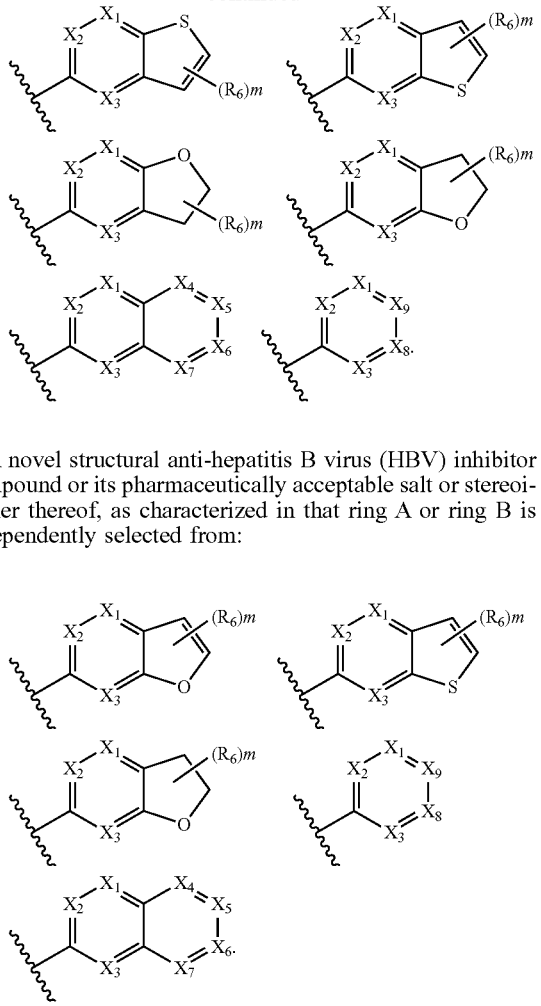

A novel structural anti-hepatitis B virus (HBV) inhibitor compound or its pharmaceutically acceptable salt or stereoisomer thereof, as characterized in that ring A or ring B is independently selected from:

A novel structural anti-hepatitis B virus (HBV) inhibitor compound or its pharmaceutically acceptable salt or stereoisomer thereof, as characterized in that:

$X_1$, $X_2$, $X_3$, $X_5$, $X_6$, $X_8$, $X_9$ are independently selected from: $CR_6$;

$X_4$ and $X_7$ are independently selected from: $CR_6$ or N.

A novel structural anti-hepatitis B virus (HBV) inhibitor compound or its pharmaceutically acceptable salt or stereoisomer thereof, as characterized in that:

$R_6$ is selected from: H, halogen, $C_1$-$C_6$ alkyl, $C_2$-$C_6$ alkenyl, $C_2$-$C_6$ alkynyl, $C_3$-$C_8$ cycloalkyl, halogen-substituted $C_1$-$C_6$ alkyl, hydroxy-substituted $C_1$-$C_6$ alkyl, Alkoxy substituted $C_1$-$C_6$ alkyl, nitro, cyano, —OR, —N(R)$_2$, —SR, —C(O)OR, —C(O)N(R)$_2$, —C(O)R, —S(O)R, —S(O)$_2$R, —S(O)$_2$N(R)$_2$, and/or —N(R)C(O)R;

$R_7$ is selected from: H, $C_1$-$C_6$ alkyl, $C_3$-$C_8$ cycloalkyl, and $C_1$-$C_6$ alkyl substituted by halogen;

each R is independently selected from: H, $C_1$-$C_6$ alkyl, $C_3$-$C_8$ cycloalkyl, and halogen-substituted $C_1$-$C_6$ alkyl.

A novel structural anti-hepatitis B virus (HBV) inhibitor compound or its pharmaceutically acceptable salt or stereoisomer thereof, as characterized in that:

$R_6$ is selected from: H, halogen, $C_1$-$C_6$ alkyl, $C_2$-$C_6$ alkynyl, and halogen-substituted $C_1$-$C_6$ alkyl;

$R_7$ is selected from: H, $C_1$-$C_6$ alkyl, and $C_3$-$C_8$ cycloalkyl.

A novel structural anti-hepatitis B virus (HBV) inhibitor compound or its pharmaceutically acceptable salt or stereoisomer thereof, as characterized in that:

X is selected from CR$_3$;
Y is selected from CRa;
Q is selected from O, S;
W is selected from NR$_5$;
R$_1$ is selected from: H;
R$_2$ is selected from C$_1$-C$_6$ alkyl, C$_2$-C$_6$ alkenyl, C$_2$-C$_6$ alkynyl, C$_3$-C$_8$ cycloalkyl, C$_3$-C$_8$ saturated or unsaturated heterocyclic ring containing N, O, S heteroatoms, and/or aryl;
wherein each occurrence of R2 is optionally substituted with one or more substituents selected from the below groups consisting of halogen, C$_1$-C$_6$ alkyl, C$_2$-C$_6$ alkenyl, C$_2$-C$_6$ alkynyl, C$_3$-C$_8$ cycloalkane Group, C$_1$-C$_6$ alkyl substituted by C$_1$-C$_3$alkoxy, C$_3$-C$_8$ saturated or unsaturated heterocyclic ring containing N, O, S heteroatoms, aryl, CF$_3$, —OR, —C(O)OR, and —C(O)N(R)$_2$;
R$_3$ and R$_4$ are each independently selected from: H, halogen, C$_1$-C$_6$ alkyl, C$_3$-C$_8$ cycloalkyl, and halogen-substituted C$_1$-C$_6$ alkyl;
R$_5$ is selected from: H, C$_1$-C$_6$ alkyl, C$_3$-C$_8$ cycloalkyl, halogen substituted C$_1$-C$_6$ alkyl, —C(O)OR, —C(O)N(R)$_2$, —C(O) R, —S(O)R, —S(O)$_2$R, and —S(O)$_2$N(R)$_2$;
wherein, when B is a monocyclic ring, R5 is not H or C$_1$-C$_6$ alkyl;
R is selected from: H, C$_1$-C$_6$ alkyl, C$_3$-C$_8$ cycloalkyl, and halogen-substituted C$_1$-C$_6$ alkyl.

A novel structural anti-hepatitis B virus (HBV) inhibitor compound or its pharmaceutically acceptable salt or stereoisomer thereof, as characterized in that:
R$_2$ is selected from: methyl, ethyl, isopropyl, tert-butyl, and/or cyclopentyl,

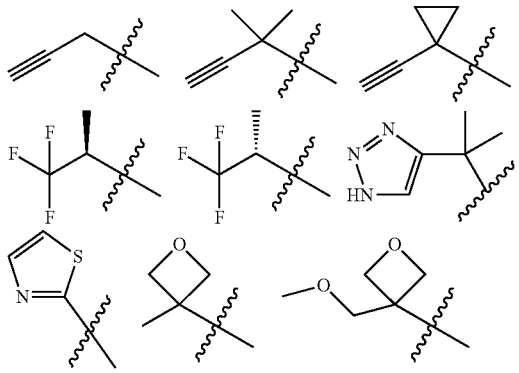

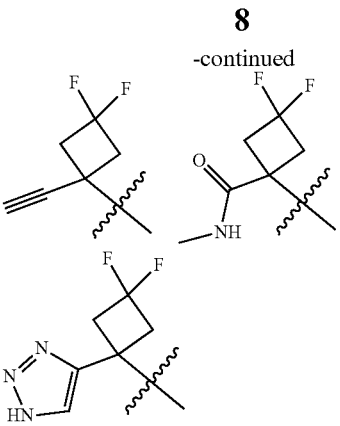

A novel structural anti-hepatitis B virus (HBV) inhibitor compound or its pharmaceutically acceptable salt or stereoisomer thereof, which is characterized in that:
R$_2$ is selected from: Tert-butyl and/or cyclopentyl,

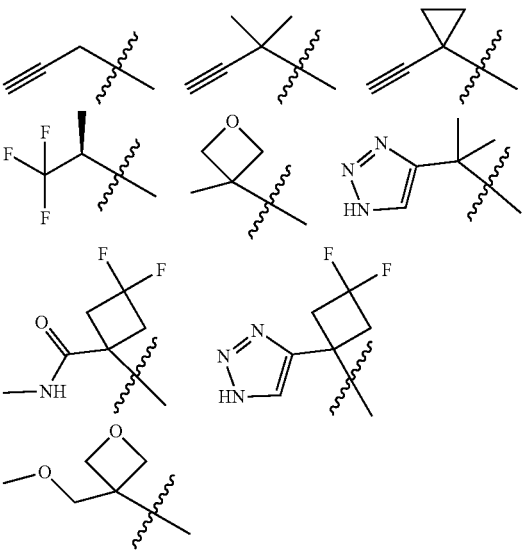

A novel structural anti-hepatitis B virus (HBV) inhibitor compound or its pharmaceutically acceptable salt or stereoisomer thereof, which is characterized in that it is preferably selected from the following compounds:

| Compound No. | Structural Formula |
|---|---|
| 1 | |
| 2 | |

-continued

| Compound No. | Structural Formula |
|---|---|
| 3 | |
| 4 | |
| 5 | |
| 6 | |
| 7 | |
| 8 | |
| 9 | |
| 10 | |

-continued
| Compound No. | Structural Formula |
|---|---|
| 11 | 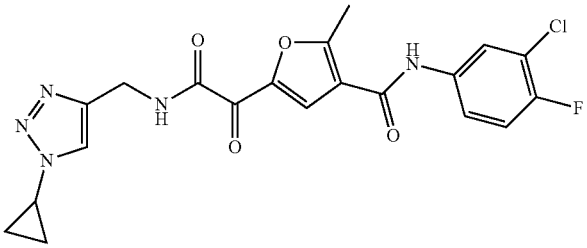 [SMILES: Cc1oc(C(=O)C(=O)NCc2cn(C3CC3)nn2)cc1C(=O)Nc1ccc(F)c(Cl)c1] |
| 12 | 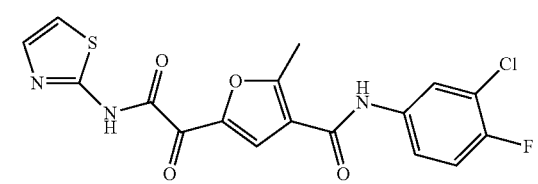 [SMILES: Cc1oc(C(=O)C(=O)Nc2nccs2)cc1C(=O)Nc1ccc(F)c(Cl)c1] |
| 13 | 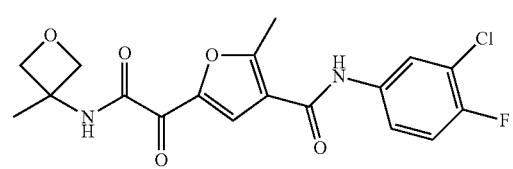 |
| 14 | 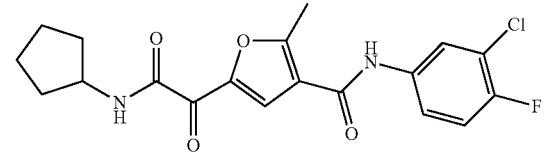 |
| 15 | 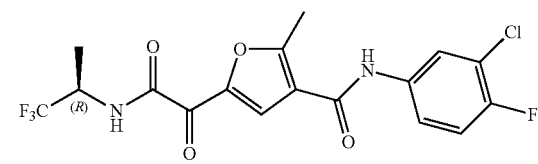 |
| 16 | 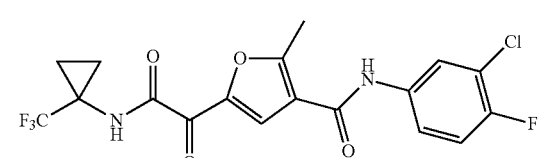 |
| 17 | 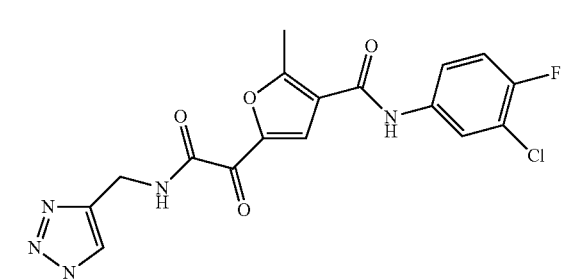 |
| 18 | 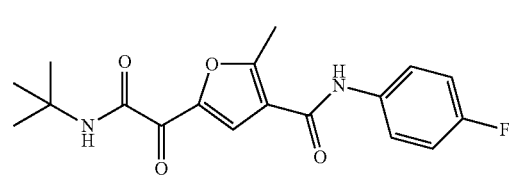 [SMILES: Cc1oc(C(=O)C(=O)NC(C)(C)C)cc1C(=O)Nc1ccc(F)cc1] |

-continued

| Compound No. | Structural Formula |
|---|---|
| 19 | *(tert-butyl-NH-C(O)-C(O)- furan(2-methyl)-C(O)-NH-(3,4-difluorophenyl))* |
| 20 | *(tert-butyl-NH-C(O)-C(O)- furan(2-methyl)-C(O)-NH-(3,4,5-trifluorophenyl))* |
| 21 | *(tert-butyl-NH-C(O)-C(O)- furan(2-methyl)-C(O)-NH-(3-cyano-4-fluorophenyl))* |
| 22 | *(tert-butyl-NH-C(O)-C(O)- furan(2-methyl)-C(O)-NH-(4-trifluoromethylphenyl))* |
| 23 | *(tert-butyl-NH-C(O)-C(O)- furan(2-methyl)-C(O)-NH-(3-bromo-4-fluorophenyl))* |
| 24 | *(tert-butyl-NH-C(O)-C(O)- furan(2-methyl)-C(O)-NH-(3-iodophenyl))* |
| 25 | *(tert-butyl-NH-C(O)-C(O)- furan(2-methyl)-C(O)-NH-(3-((trimethylsilyl)ethynyl)-4-fluorophenyl))* |
| 26 | *(tert-butyl-NH-C(O)-C(O)- furan(2-methyl)-C(O)-NH-(3-((trimethylsilyl)ethynyl)phenyl))* |

-continued

| Compound No. | Structural Formula |
|---|---|
| 27 | *(structure: tert-butyl NH-C(O)-C(O)- furan (2-methyl) -C(O)NH- phenyl(3-ethynyl, 4-F))* |
| 28 | *(structure: tert-butyl NH-C(O)-C(O)- furan (2-methyl) -C(O)NH- phenyl(3-ethynyl))* |
| 29 | *(structure: tert-butyl NH-C(O)-C(O)- thiophene (2-methyl) -C(O)NH- phenyl(3-Cl, 4-F))* |
| 30 | *(structure: propargyl NH-C(O)-C(O)- thiophene (2-methyl) -C(O)NH- phenyl(3-Cl, 4-F))* |
| 31 | *(structure: 3-methyloxetan-3-yl NH-C(O)-C(O)- thiophene (2-methyl) -C(O)NH- phenyl(3-Cl, 4-F))* |
| 32 | *(structure: cyclopentyl NH-C(O)-C(O)- thiophene (2-methyl) -C(O)NH- phenyl(3-Cl, 4-F))* |
| 33 | *(structure: (R)-1,1,1-trifluoropropan-2-yl NH-C(O)-C(O)- thiophene (2-methyl) -C(O)NH- phenyl(3-Cl, 4-F))* |
| 34 | *(structure: tert-butyl NH-C(O)-C(O)- thiophene (2-methyl) -C(O)NH- phenyl(3,4-diF))* |
| 35 | *(structure: tert-butyl NH-C(O)-C(O)- thiophene (2-methyl) -C(O)NH- phenyl(3,4,5-triF))* |

-continued

| Compound No. | Structural Formula |
|---|---|
| 36 | *(structure: N-tert-butyl oxamide linked to 2,4-dimethylthiophene-3-carboxamide with 3-chloro-4-fluorophenyl)* |
| 37 | *(structure: 3-(methoxymethyl)oxetan-3-yl oxamide linked to 2,4-dimethylthiophene-3-carboxamide with 3-chloro-4-fluorophenyl)* |
| 38 | *(structure: 2-methylbut-3-yn-2-yl oxamide linked to 2,4-dimethylthiophene-3-carboxamide with 3-chloro-4-fluorophenyl)* |
| 39 | *(structure: 2-methylbut-3-yn-2-yl oxamide linked to 2,4-dimethylthiophene-3-carboxamide with benzofuran-5-yl)* |
| 40 | *(structure: 1-ethynylcyclopropyl oxamide linked to 2,4-dimethylthiophene-3-carboxamide with benzofuran-5-yl)* |
| 41 | *(structure: 3-(methoxymethyl)oxetan-3-yl oxamide linked to 2,4-dimethylthiophene-3-carboxamide with benzofuran-5-yl)* |
| 42 | *(structure: N-tert-butyl oxamide linked to 2-methylfuran-3-carboxamide with 4-fluorophenyl)* |
| 43 | *(structure: N-tert-butyl oxamide linked to 2-tert-butylfuran-3-carboxamide with 4-fluorophenyl)* |
| 44 | *(structure: N-tert-butyl oxamide linked to thiazole-4-carboxamide with 3-chloro-4-fluorophenyl)* |

-continued

| Compound No. | Structural Formula |
|---|---|
| 45 | |
| 46 | |
| 47 | |
| 48 | |
| 49 | |
| 50 | |
| 51 | |
| 52 | |
| 53 | |

-continued
| Compound No. | Structural Formula |
|---|---|
| 54 | 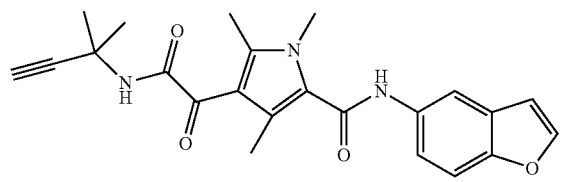 [SMILES: C#CC(C)(C)NC(=O)C(=O)c1c(C)c(C(=O)Nc2ccc3occc3c2)n(C)c1C] |
| 55 | 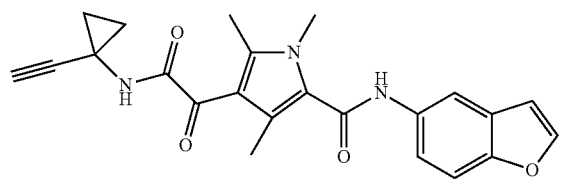 [SMILES: C#CC1(NC(=O)C(=O)c2c(C)c(C(=O)Nc3ccc4occc4c3)n(C)c2C)CC1] |
| 56 | 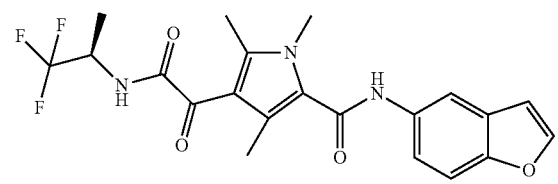 [SMILES: Cc1c(C(=O)C(=O)N[C@H](C)C(F)(F)F)c(C)n(C)c1C(=O)Nc1ccc2occc2c1] |
| 57 | 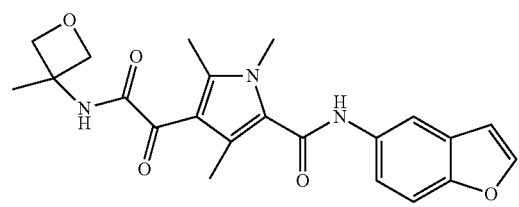 [SMILES: Cc1c(C(=O)C(=O)NC2(C)COC2)c(C)n(C)c1C(=O)Nc1ccc2occc2c1] |
| 58 | 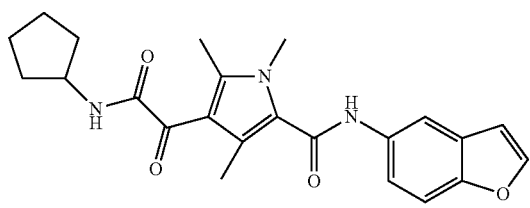 [SMILES: Cc1c(C(=O)C(=O)NC2CCCC2)c(C)n(C)c1C(=O)Nc1ccc2occc2c1] |
| 59 | 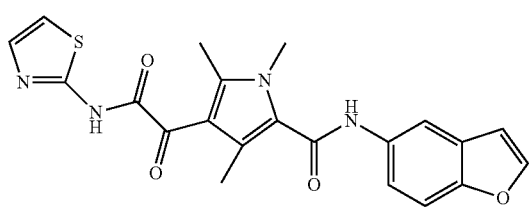 [SMILES: Cc1c(C(=O)C(=O)Nc2nccs2)c(C)n(C)c1C(=O)Nc1ccc2occc2c1] |
| 60 | 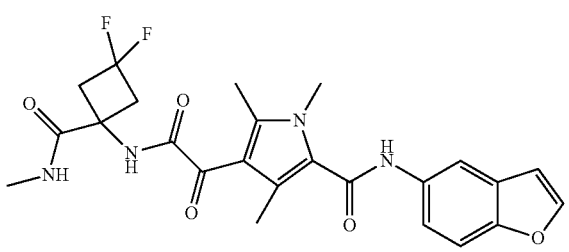 [SMILES: CNC(=O)C1(NC(=O)C(=O)c2c(C)c(C(=O)Nc3ccc4occc4c3)n(C)c2C)CC(F)(F)C1] |

-continued
| Compound No. | Structural Formula |
|---|---|
| 61 | 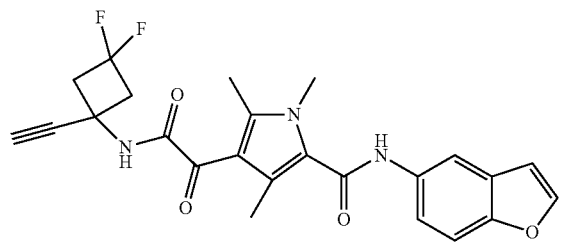 [SMILES: C#CC1(NC(=O)C(=O)c2c(C)c(C(=O)Nc3ccc4occc4c3)n(C)c2C)CC(F)(F)C1] |
| 62 | 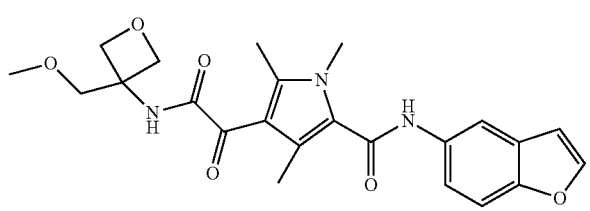 [SMILES: COCC1(NC(=O)C(=O)c2c(C)c(C(=O)Nc3ccc4occc4c3)n(C)c2C)COC1] |
| 63 | 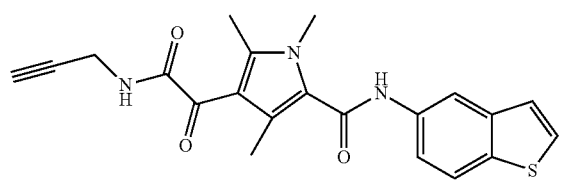 [SMILES: C#CCNC(=O)C(=O)c1c(C)c(C(=O)Nc2ccc3sccc3c2)n(C)c1C] |
| 64 | 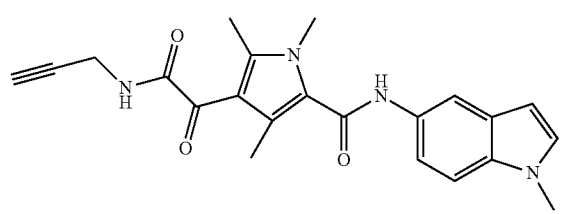 [SMILES: C#CCNC(=O)C(=O)c1c(C)c(C(=O)Nc2ccc3c(ccn3C)c2)n(C)c1C] |
| 65 | 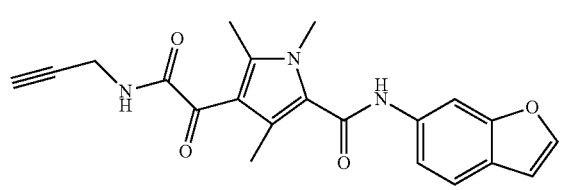 [SMILES: C#CCNC(=O)C(=O)c1c(C)c(C(=O)Nc2ccc3ccoc3c2)n(C)c1C] |
| 66 | 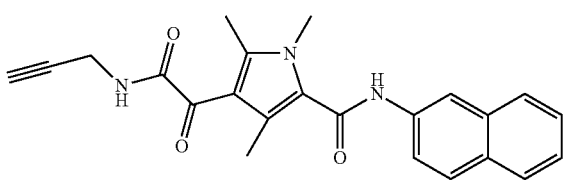 [SMILES: C#CCNC(=O)C(=O)c1c(C)c(C(=O)Nc2ccc3ccccc3c2)n(C)c1C] |
| 67 | 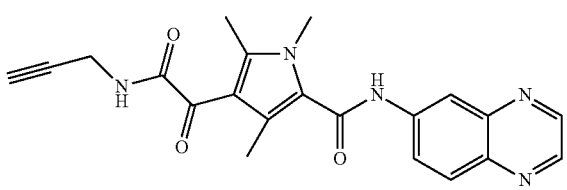 [SMILES: C#CCNC(=O)C(=O)c1c(C)c(C(=O)Nc2ccc3nccnc3c2)n(C)c1C] |

-continued

| Compound No. | Structural Formula |
|---|---|
| 68 | |
| 69 | |
| 70 | |
| 71 | |
| 72 | |
| 73 | |
| 74 | |
| 75 | |

-continued

| Compound No. | Structural Formula |
|---|---|
| 76 | (structure) |
| 77 | (structure) |
| 78 | (structure) |
| 79 | (structure) |
| 80 | (structure) |
| 81 | (structure) |
| 82 | (structure) |

-continued

| Compound No. | Structural Formula |
|---|---|
| 83 | |
| 84 | |
| 85 | |
| 86 | |
| 87 | |
| 88 | |
| 89 | |
| 90 | |

| Compound No. | Structural Formula |
|---|---|
| 91 | 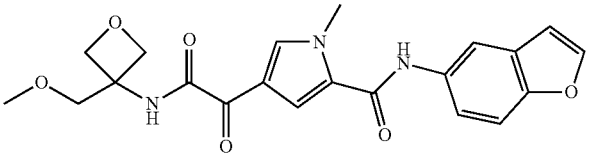 [SMILES: COCC1(NC(=O)C(=O)c2cc(C(=O)Nc3ccc4occc4c3)n(C)c2)COC1] |
| 92 | 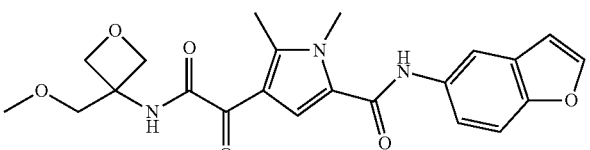 |

More preferably, the novel structure anti-hepatitis B virus (HBV) inhibitor compound is selected from:

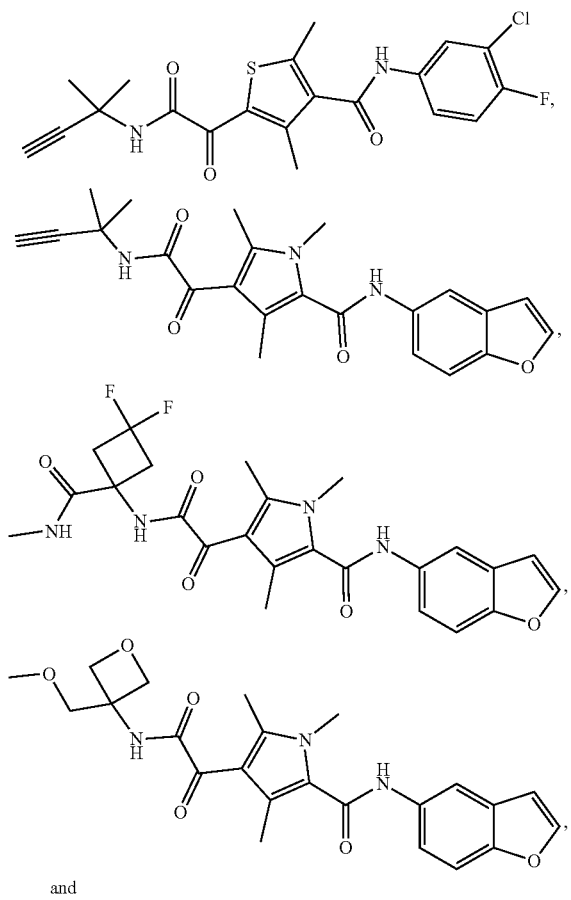

and

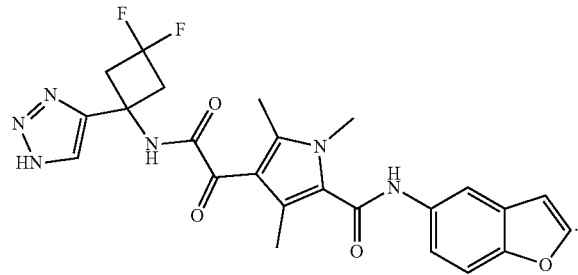

In the second aspect, the present invention provides a pharmaceutical composition, which includes the compound of the first aspect of the present invention, its pharmaceutically acceptable salt, its solvent compound or its N-oxide compound, and the pharmaceutically acceptable auxiliary material.

Preferably, in the pharmaceutical composition in the second aspect of the present invention, the pharmaceutically acceptable auxiliary material is selected from at least one of auxiliary material, diluent, disintegrant, glidant and lubricant, the preferably and the pharmaceutically acceptable auxiliary material include dicalcium phosphate, cellulose, compressible sugars, dicalcium phosphate dehydrate, lactose mannitol, microcrystalline cellulose, starch and/or tricalcium phosphate.

Preferably, the pharmaceutical composition in the second aspect of the present invention further includes one or more antiviral agents, and the antiviral agent is preferably selected from: At least one among the Hepatitis B virus (HBV) polymerase inhibitor, interferon, virus entry inhibitor, virus maturation inhibitors, assembly regulators, reverse transcriptase inhibitors, and TLR-agonists.

More preferably, in the pharmaceutical composition in the second aspect of the present invention, the reverse transcriptase inhibitor is selected from: Entecavir, Tenofovir, HepDirect-tenofovir, Entricitabine, Adefovir, HepDirect-Adefovir, Pradefovir, Acyclovir, Ganciclovir, GS-7340 (TAF), Besifovir, Birinapant (HY-16591), Ribavirin and Efavirenz, and preferably Tenofovir.

In the third aspect, the present invention provides the compound of the first aspect of the present invention, its pharmaceutically acceptable salt, its solvent compound or its N-oxide compound in the preparation of drugs for the treatment of hepatitis B virus (HBV) infection or preparation of drug for use as an alleviating method for liver injury as caused by hepatitis B virus (HBV) infection.

In the fourth aspect, the present invention provides a method for treating, eradicating, reducing, alleviating or inhibiting hepatitis B virus (HBV) infection or a method for alleviating liver damage caused by hepatitis B virus (HBV) infection, which includes that the individual in need is administered with an effective dosage of the compound of the first aspect of the present invention, its pharmaceutically acceptable salt, its solvent compound, or its N-oxide compound.

In the fifth aspect, the present invention provides a preparation method of the compound of the first aspect of the present invention, which includes the following four preparation processes:

Scheme 1: The synthesis of the compound of general formula I can be carried out as described in Scheme 1. The carboxylic acid I-A and the amine I-B are coupled under the action of a condensing agent to obtain the intermediate amide I-C. Intermediate I-C can yield intermediate I-D through the Lewis acid such as AlCl₃ or LDA, n-butyllithium and/or tert-butyllithium; intermediate I-D is hydrolyzed under alkaline conditions to give intermediate I-E, the α-keto acid of the intermediate I-E is coupled with the intermediate I-F in presence of a condensing agent, the compound of general formula I is thus obtained.

Scheme 1: Synthetic route of the compound of general formula I

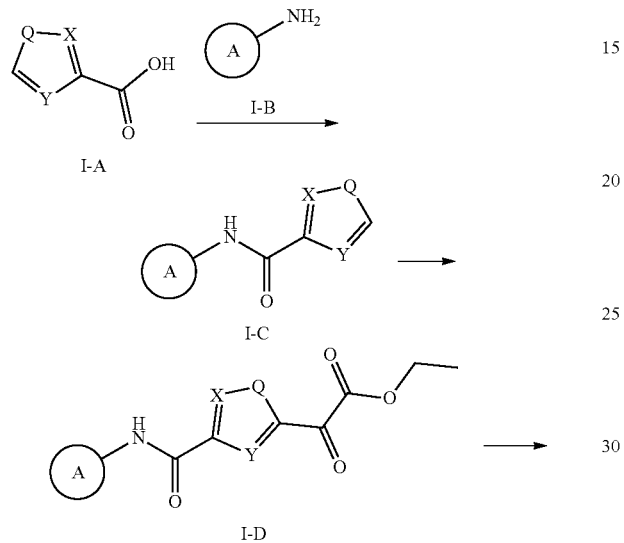

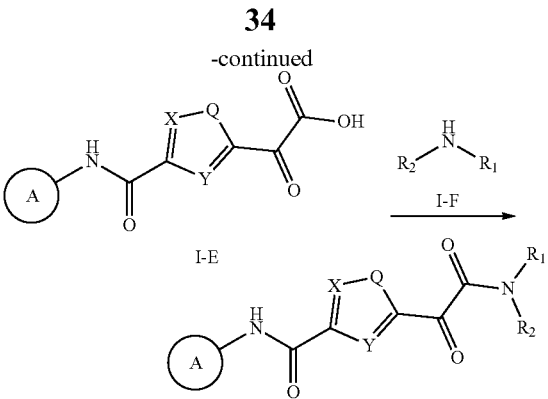

Scheme 2: The synthesis of the compound of general formula I can also be carried out as the two routes described in Scheme 2.

a) The carboxylate I-G is firstly hydrolyzed and then directly coupled with the amine I-B under the presence of a condensing agent to obtain the amide of the intermediate I-H. Intermediate I-H then yields the intermediate I-D by Lewis acid such as AlCl₃ or LDA, n-butyllithium, and/or tert-butyllithium. Intermediate I-D is selectively hydrolyzed with inorganic base NaOH to obtain intermediate I-E, the α-keto acid of I-E and amine of intermediate IF are coupled in the presence of a condensing agent to obtain the compound of general formula I.

b) Intermediate II is obtained by reaction of carboxylate I-G and alkylmethylene amine. Intermediate II is hydrolyzed to yield intermediate I-J in the general formula. The carboxylic acid of intermediate I-J and amine of I-B are coupled under the presence of a condensing agent to obtain the compound in general formula I.

Scheme 2: Synthetic route of the compound of general formula 1

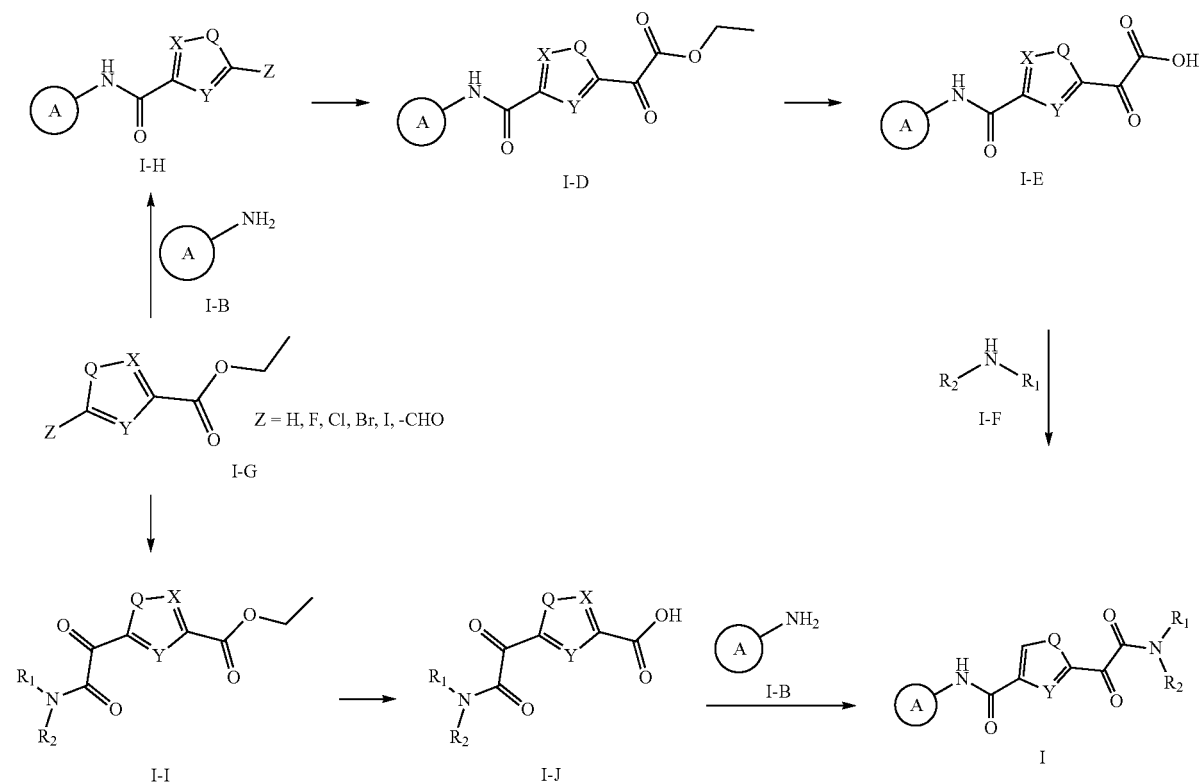

Scheme 3: The synthesis of the compound of general formula II can be carried out as described in scheme 3. Carboxylic acid ester II-A is synthesized under Lewis acid such as AlCl₃ or LDA, n-butyl lithium, and/or tert-butyl lithium to obtain intermediate II-B, and intermediate II-B is selectively hydrolyzed to yield the corresponding oxalic acid II-C; intermediate II-C and amine of I-F are coupled under the presence of a condensing agent to obtain intermediate II-D; then the intermediate II-D is further hydrolyzed to yield II-E; and intermediate II-E and amine are coupled under the action of a condensing agent to obtain the compound in general formula II.

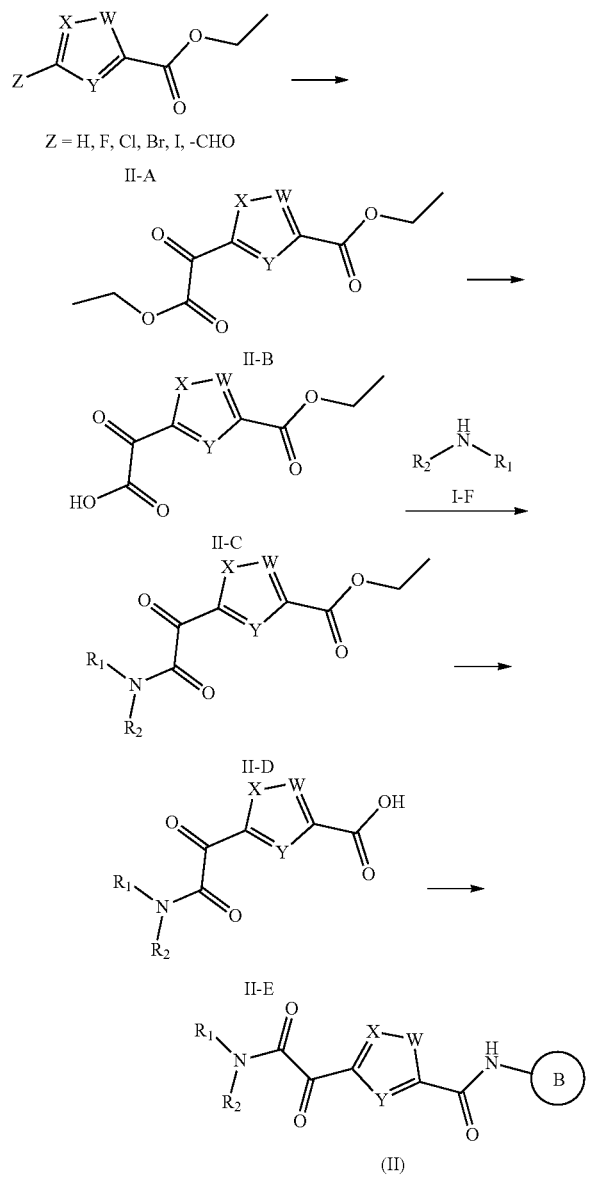

Scheme 4: The synthesis of the compound in general formula II can also be carried out as described in scheme 4. The carboxylate II-A is firstly hydrolyzed to obtain the corresponding carboxylic acid intermediate II-F. The intermediate II-F is coupled with the amine under the presence of a condensing agent to yield the intermediate II-G. The intermediate II-G is placed in a Lewis acid such as AlCl₃ Or LDA, n-butyl lithium, tert-butyl lithium to give the intermediate II-H; then the intermediate II-H is further hydrolyzed to obtain II-I; and intermediate II-I and amine of I-F are coupled under the action of a condensing agent to obtain the compound in general formula II.

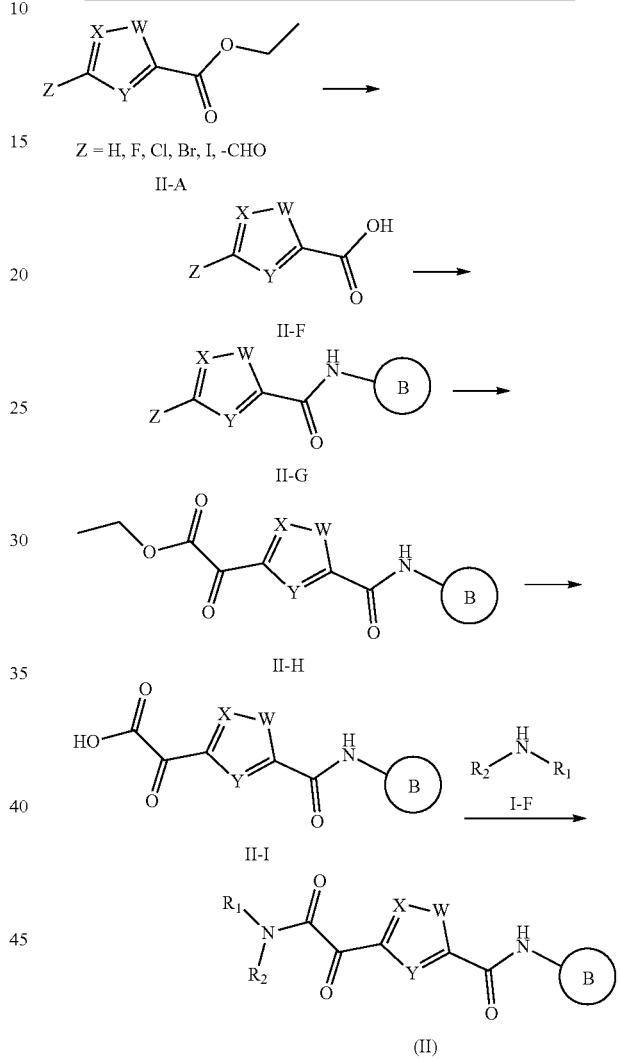

Now some implementation schemes of the present invention will be described in detail.

The present invention intends to cover all alternatives, modifications and equivalent technical solutions, which are all included in the scope of the present invention as defined by the claims. Those skilled in the art should recognize that many methods and materials similar or equivalent to those described herein can be used to implement the present invention. The invention is by no means limited to the methods and materials described herein. In the case where one or more of the combined documents, patents and similar files are different or contradictory to this application (including but not limited to the defined terms, term applications, described technologies, etc.), the present invention shall prevail.

Unless otherwise defined, the terms used in the present invention have the meaning generally accepted in this field. Further, some of the terms used in the present invention are defined as follows:

The term "include" is an open expression, that is, includes the content specified in the present invention, but does not exclude other aspects.

The term "patient" used in the present invention may include humans (adults and children) or other animals. In some implementation schemes, the "patient" refers to a human being.

The term "halogen" refers to fluorine, chlorine, bromine and iodine. In particular, halogen refers to fluorine, chlorine and bromine.

The term "cyano" refers to the group —CN.
The term "hydroxy" refers to the group —OH.
The term "carbonyl" refers to the group —C(=O)—.
The term "oxalate" refers to the group

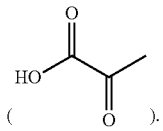

( ).

The term "carboxy" refers to the group —COON
The term "alkynyl" refers to the group

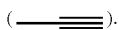

( ).

The term "amino" refers to a primary (—NH$_2$), secondary (—NH—) or tertiary amino group

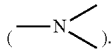

( ).

The term of "alkyl" refers to a saturated aliphatic hydrocarbon group that is straight or branched. The alkyl group in the present application is preferably a C$_{1-6}$ alkyl group, which means a saturated linear or branched alkyl group containing 1 to 6 carbon atoms; the particularly preferred alkyl group in the present application is a C$_4$ alkyl group, namely saturated linear or branched alkyl groups of 1 to 4 carbon atoms, such as methyl, ethyl, n-propyl, isopropyl, 1-butyl, 2-butyl, tert-butyl and the like.

"Alkoxy" refers to the (alkyl-O—) group. Wherein, the alkyl group is as defined above. A preferred alkoxy group is a C$_{1-6}$ alkoxy group, and a particularly preferred alkoxy group is a C$_{1-4}$ alkoxy group. The term C$_{1-6}$ alkoxy includes methoxy, ethoxy, n-propoxy, isopropoxy and the like.

The term "cycloalkyl" means a saturated carbocyclic ring of 3 to 12 carbon atoms, particularly 3 to 6 carbon atoms, such as the cyclopropyl, cyclobutyl, cyclopentyl, cyclohexyl and the like.

"Haloalkyl" or "haloalkoxy" means that an alkyl or alkoxy group is substituted with one or more halogen atoms which may be the same or different. Examples include but are not limited to: difluoromethyl, trifluoromethyl, trifluoromethoxy and the like.

The term "tautomers" refers to structural isomers of the organic compounds that are easily converted into each other through a chemical reaction called tautomerization. This reaction usually results in the migration of hydrogen atoms or protons as accompanied by the conversion of single bonds and adjacent double bonds.

The term "chiral" refers to a molecule that has the property of not being able to overlap with its mirror image; and "achiral" refers to a molecule that can overlap with its mirror image.

The term "enantiomers" refers to two isomers of a compound that cannot overlap but are mirror images of each other.

The term "diastereomer" refers to a stereoisomer thereof with two or more chiral centers and whose molecules are not mirror images of each other. Diastereomers generally have different physical properties, such as boiling point, melting point, spectral properties and reactivity.

As described in the present invention, the compounds of the present invention can be optionally substituted with one or more substituents, such as the above general formula compounds, or the specific compounds of the present invention, or specific examples and subclasses in the examples, and a class of compounds included in the present invention.

It should be understood that the term "optionally substituted" and the term "substituted or unsubstituted" can be used interchangeably. Generally speaking, the term "substituted" means that one or more hydrogen atoms in a given structure are replaced by specific substituents. Unless otherwise indicated, an optional substituent group can be substituted at each substitutable position of the group. When more than one position in the given structural formula can be substituted by one or more substituents selected from specific groups, the substituents can be substituted at each position with the same or different substitutions. The substituents can be but are not limited to: fluorine, chlorine, bromine, iodine, methylene

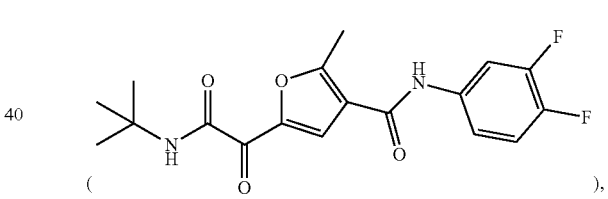

oxo

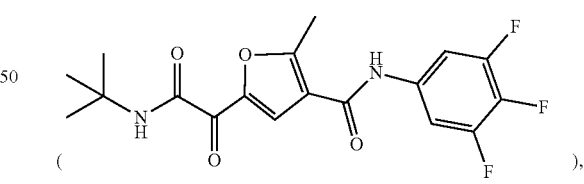

alkyl, alkoxy, cyano, nitro, alkylamino, mercapto and amino, etc.

The term "pharmaceutically acceptable salts" refers to certain salts of the above-mentioned compounds that can maintain the original biological activity and are suitable for medicinal use. The pharmaceutically acceptable salts of the compounds represented by Formula I and Formula II may be salts formed with suitable acids. The suitable acids include inorganic acids and organic acids, such as acetic acid, benzenesulfonic acid, benzoic acid, camphorsulfonic acid, citric acid, ethanesulfonic acid, fumaric acid, gluconic acid, glutamic acid, hydrobromic acid, hydrochloric acid, isethionic acid, lactic acid, malic acid, maleic acid, mandelic acid, methanesulfonic acid, nitric acid, phosphoric acid, succinic acid, sulfuric acid, tartaric acid and p-toluenesulfonic acid.

For the sake of understanding, the present invention will be described in detail below through specific embodiments (or examples) and drawings. It should be particularly pointed out that these descriptions are merely exemplary ones and do not constitute a limitation on the scope of the present invention. Based on the description of this specification, many changes and modifications of the present invention are obvious to those skilled in the art. In addition, the present invention cites published documents for the purpose of describing the present invention more clearly, and their full content is incorporated herein by reference, as if their full text has been repeated and clearly described in this document.

DESCRIPTION OF THE DRAWINGS

FIG. 1 is a graph showing the plasma concentration of compounds 36, 52, 53, and 54 of the present invention and control Cpd 7a administered intragastrically (20 mg/kg) in rats.

DETAILED WAYS

The following reactions are generally operated under a positive pressure of nitrogen. The reaction flasks are all plugged with suitable rubber stoppers, and the substrate can be injected through a syringe. The glassware is dried. The chromatographic column is a silica gel one. The NMR data was measured by the Bruker Advance 400 NMR instrument, using $CDCl_3$, DMSO-$d^6$ or $CD_3OD$ as the solvent (reported in ppm), and TMS (0 ppm) or chloroform (7.25 ppm) served as the reference standard. When there are multiple peaks, use the following abbreviations: s (singlet), s, s (singlet, singlet), d (doublet), t (triplet), m (multiplet), br (broad peak), dd (doublet of doublets), ddd (doublet of doublet of doublets), ddt (doublet of doublet of triplets), dddd (doublet of doublet of doublet of doublets), td (triplet of doublets), brs (broadened singlet). The coupling constant is expressed in Hertz (Hz).

Low-resolution mass spectrometry (MS) data was measured by an Agilent 1100 series LC-MS spectrometer. The ESI source is used in the LC-MS spectrometer.

The purity of the compound is evaluated by Agilent 1100 series high performance liquid chromatography (HPLC), where UV detection is at 220 nm and 254 nm, Zorbax SB-C18 column whose specification is 2.1×30 mm, 4 μm, 10 minutes, and the flow rate is 0.6 ml/min, 5-95% (0.1% formic acid acetonitrile solution) and (0.1% formic acid aqueous solution), keep the column temperature at 40° C.

The following abbreviations are used throughout the present invention:

| | |
|---|---|
| DCM or $CH_2Cl_2$ | Dichloromethane |
| EtOAc or EA | Ethyl acetate |
| THF | Tetrahydrofuran |
| Me | Methyl |
| MeOH | Methanol |
| LDA | Lithium Diisopropylamide |
| HATU | 2-(7-benzotriazole oxide)-N,N,N',N'-tetramethylurea hexafluorophosphate |
| TEA | Triethylamine |
| RT | Room temperature |
| DIPEA | N,N-Diisopropylethylamine |
| DMF | N,N-Dimethylformamide |
| TMSCL | Trimethylchlorosilane |
| $CDCl_3$ | Deuterated chloroform |
| $Ph_3P$ | Triphenylphosphine |
| Boc | Tert-Butoxycarbonyl |
| $Pd(OAc)_2$ | Palladium(□) acetate |
| Sodium ascorbate | Sodium Ascorbate |
| DMSO-$d^6$ | Deuterated Dimethyl Sulfoxide |
| DMSO | Dimethyl sulfoxide |
| KOAc | Potassium acetate |
| NBS | Bromosuccinimide |
| TLC | Thin layer chromatography |
| c | Concentration |
| g | Gram |
| mg | Milligram |
| v/v or v:v | Volume ratio |
| mol | Mole |
| mmol | Millimoles |
| mL | Milliliter |
| nM (nmol/L) | Nanomole per liter |
| L | Liter |
| h | Hour |
| t1/2 | Half-life period |
| AUC | Area under the drug-time curve |
| Vss | Steady-state apparent volume of distribution |
| CL or clearance | Clearance rate |
| F, | absolute |
| Dose | Dosage |
| Tmax | Peak time |
| Cmax | Max. Concentration |
| hr * ng/mL | Blood concentration * time |

PREPARATION EXAMPLES

The following synthetic schemes (Schemes 1-4) can be used to synthesize the compounds of the present invention. The methods described are illustrative scheme descriptions for easier understanding of the examples, and do not constitute a limitation on the scope of the present invention.

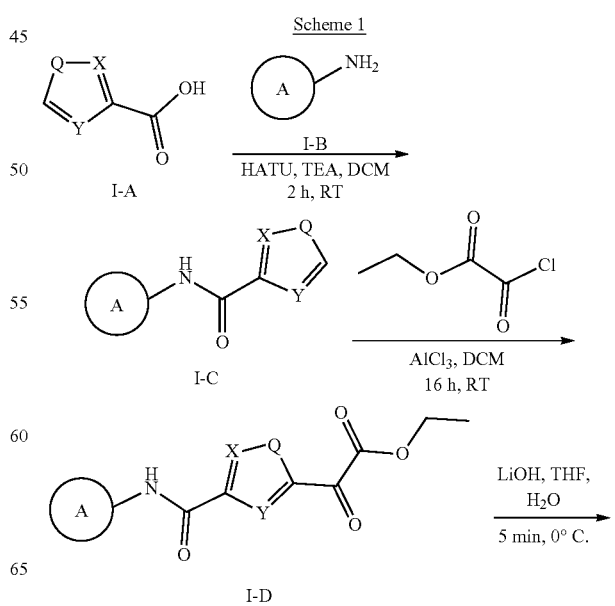

Scheme 1

41
-continued
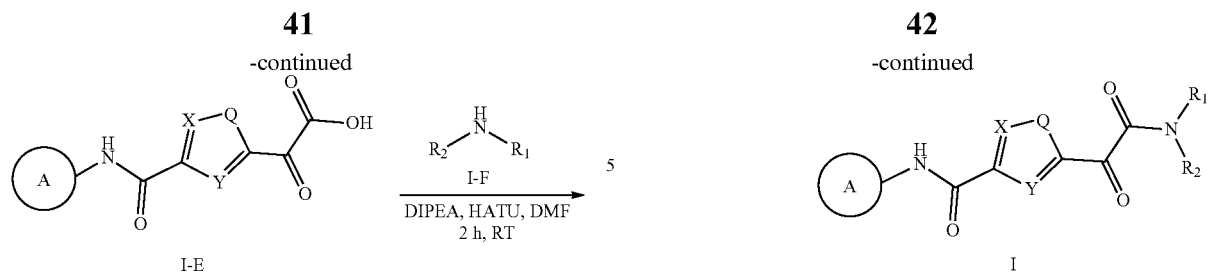
42
-continued
Scheme 2
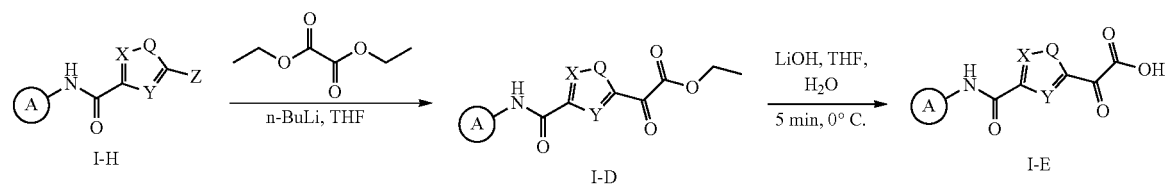
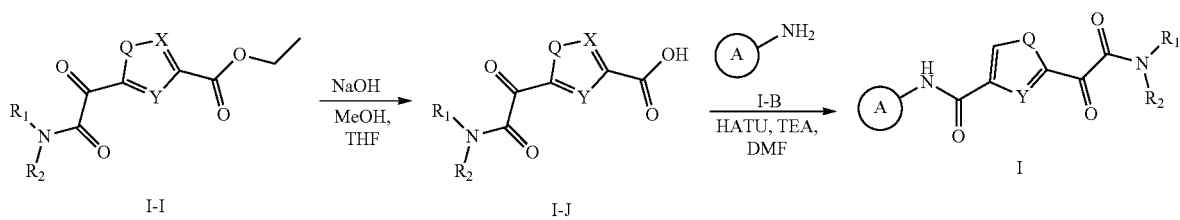

Scheme 3
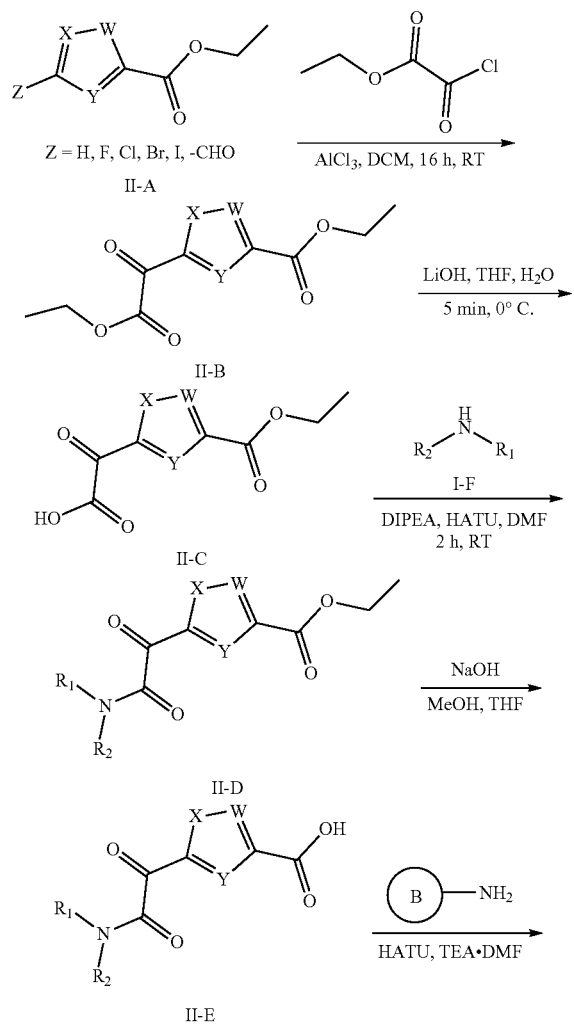
Scheme 4
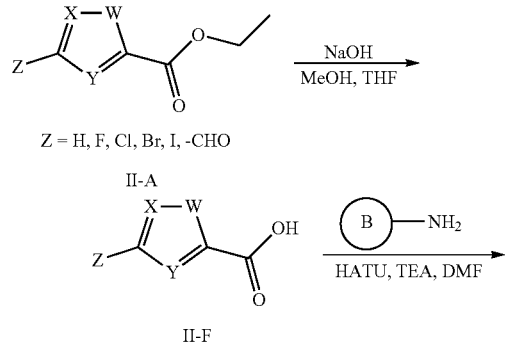
-continued
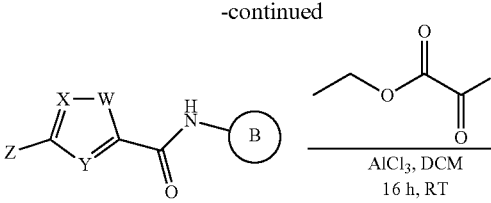
The present invention will be further described below in conjunction with embodiments (or examples), but the embodiments/examples are not used to limit the protection scope of the present invention.
Example 1 to Example 17 were Synthesis According to the Specific Route Shown in Scheme 1 Below
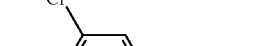

-continued

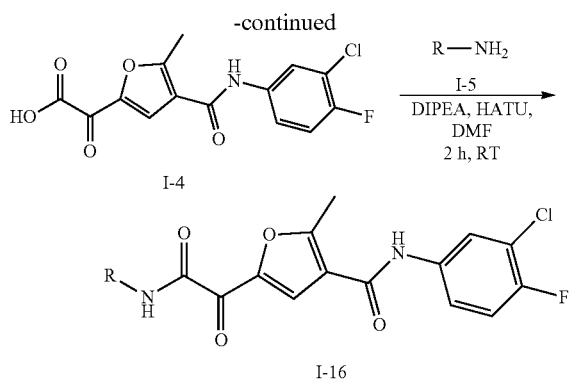

Example 1

2-Methyl-3-amide-N-(3-chloro-4-fluorophenyl)-5-(2-tert-butylamino-oxalyl)-furan (compound 1)

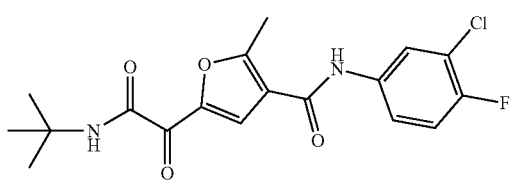 [SMILES: Cc1oc(C(=O)C(=O)NC(C)(C)C)cc1C(=O)Nc1ccc(F)c(Cl)c1]

Step 1a: 2-Methyl-3-amide-N-(3-chloro-4-fluorophenyl)-furan (Compound I-2)

2-Methylfuran-3-formic acid (I-1, 10.1 g, 1.0 eq.) was dissolved in 300 mL of dichloromethane, and triethylamine (24.2 g, 3.0 eq.) and HATU (36.5 g, 1.2 eq.) were added under agitation. After reacting at room temperature for 5 min, 3-chloro-4-fluoroaniline (13.9 g, 1.2 eq.) was added, and the reaction was carried out at room temperature for 2 h. TLC monitored the completion of the reaction. The reaction was terminated by adding water, and washed with 30 mL of saturated brine by three times, the organic phase was dried and concentrated under reduced pressure, and separated by silica gel column to obtain 12.7 g of the target compound with a yield of 63%. (ES, m/z): [M+1]$^+$=254.

Step 1b: 2-Methyl-3-amide-N-(3-chloro-4-fluorophenyl)-5-oxalatoethyl-furan (Compound I-3)

Under nitrogen protection, AlCl$_3$ (17.1 g, 4.0 eq.) was dissolved in dichloromethane, then the reaction solution was cooled to 0° C., ethyl oxalyl chloride (17.4 g, 4.0 eq.) was added with stirring, and the mixture was stirred at 0° C. for 30 min. Then I-2 (8.1 g, 1.0 eq.) was added to the above reaction solution, and the reaction was allowed to warm up naturally for 16 h. TLC monitored the completion of the reaction. The reaction was quenched by adding dilute hydrochloric acid, and then washed with water and saturated brine. The organic phase was dried and concentrated under reduced pressure, and separated by silica gel column to obtain 5.0 g of the target compound with a yield of 44%. (ES, m/z): [M+1]$^+$=354.

Step 1c: 2-Methyl-3-amide-N-(3-chloro-4-fluorophenyl)-5-oxalo-furan (Compound I-4)

I-3 (353 mg, 1.0 eq.) was dissolved in 6 mL of tetrahydrofuran and 2 mL of water, the reaction solution was cooled to 0° C., and LiOH (84 mg, 2.0 eq.) was added. After 5 minutes of reaction, TLC monitored the completion of the reaction. The solution was concentrated under reduced pressure to remove tetrahydrofuran, then adjust to pH=3 with 1M dilute hydrochloric acid under ice bath, extract twice with 10 times ethyl acetate. The organic phases were combined and dried over anhydrous sodium sulfate, and then was concentrate under reduced pressure, and the product was used directly in the next step. (ES, m/z): [M+1]$^+$=326.

Step 1d: 2-Methyl-3-amide-N-(3-chloro-4-fluorophenyl)-5-(2-tert-butylamino-oxalyl)-furan (Compound 1)

Intermediate I-4 was dissolved in 5 mL DMF, DIPEA (387 mg, 3.0 eq.) and tert-butylamine (110 mg, 1.5 eq.) were added successively, HATU (456 mg, 1.2 eq.) was added, and the reaction was carried out at room temperature for 2 h. TLC monitored the completion of the reaction. The reaction was quenched by adding water, then ethyl acetate was added, and then the solution washed with saturated brine. The obtained organic phase was dried, concentrated under reduced pressure, and separated by silica gel column to obtain 90 mg of the target compound as a white solid with a yield of 24%. (ES, m/z): [M+1]$^+$=381, $^1$H-NMR: (400 MHz, DMSO-d6, ppm): δ10.33 (s, 1H), 8.49(s, 1H), 8.24(s, 1H), 8.05 (dd, J=6.8, 2.4 Hz, 1H), 7.70 (ddd, J=6.8, 4.0, 2.4 Hz, 1H), 7.42 (t, J=9.2 Hz, 1H), 2.70 (s, 3H), 1.38 (s, 9H).

Example 2

2-Methyl-3-amide-N-(3-chloro-4-fluorophenyl)-5-(2-propargylamino-oxalyl)-furan (Compound 2)

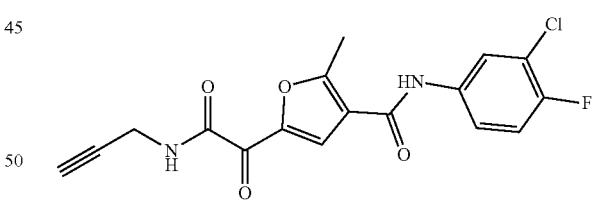

Dissolve the intermediate I-4 in 5 mL DMF, and DIPEA (387 mg, 3.0 eq.), propargylamine (83 mg, 1.5 eq.) and HATU (456 mg, 1.2 eq.) were added to react at room temperature for 2 h. TLC monitored the completion of the reaction. The reaction was quenched by adding water, then ethyl acetate was added, and then the solution was washed with saturated brine. The obtained organic phase was dried, concentrated under reduced pressure, and separated by a silica gel column to obtain 109 mg of the target compound as a white solid with a yield of 30%. (ES, m/z): [M+1]$^+$=363, H-NMR: (300 MHz, CDCl$_3$, ppm): δ8.45 (s, 1H), 7.87(dd, J=6.6, 2.4 Hz, 1H), 7.80(s, 1H), 7.60 (b, 1H), 7.39 (m, 1H), 7.15 (t, J=2.4 Hz,1H), 4.19 (dd, J=5.7, 2.4 Hz, 2H), 2.80 (s, 3H), 2.34 (t, J=2.4 Hz, 1H).

Example 3

2-Methyl-3-amide-N-(3-chloro-4-fluorophenyl)-5-(2-(1-methylpropynamido)-oxalyl)-furan (Compound 3)

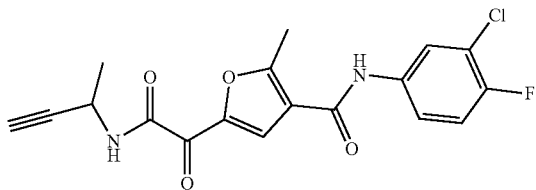 [SMILES: C#CC(C)NC(=O)C(=O)c1cc(C(=O)Nc2ccc(F)c(Cl)c2)c(C)o1]

Intermediate I-4 was dissolved in 5 mL DMF, DIPEA (387 mg, 3.0 eq.), 1-methylpropynamine (104 mg, 1.5 eq.) and HATU (456 mg, 1.2 eq.) were added in sequence. The system reacted at room temperature for 2 h. TLC monitored the completion of the reaction. The reaction was quenched by adding water, then ethyl acetate was added, and then the solution was washed with saturated brine. The obtained organic phase was dried, concentrated under reduced pressure, and separated by a silica gel column to obtain 85 mg of the target compound as a pale yellow solid with a yield of 23%. (ES, m/z): [M+1]$^+$=377, H-NMR: (400 MHz, CDCl$_3$, ppm): δ 8.43 (s, 1H), 8.88(dd, J=6.4, 2.4 Hz, 1H), 7.57(s, 1H), 7.52 (m, 1H), 7.43 (d, J=3.2 Hz,1H), 7.17 (t, J=8.4 Hz,1H), 4.84(m, 1H), 2.83 (d , J=12.4 Hz, 3H), 2.38(d, J=2.4 Hz, 1H), 2.34 (t, J=6.8 Hz, 3H).

Example 4

2-Methyl-3-amide-N-(3-chloro-4-fluorophenyl)-5-(2-(1,1-dimethylpropynamido)-oxalyl)-furan (Compound 4)

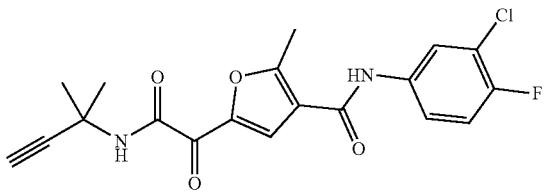 [SMILES: C#CC(C)(C)NC(=O)C(=O)c1cc(C(=O)Nc2ccc(F)c(Cl)c2)c(C)o1]

Intermediate I-4 was dissolved in 5 mL DMF, then DIPEA (387 mg, 3.0 eq.), 1,1-dimethylpropynamine (124 mg, 1.5 eq.), and HATU (456 mg, 1.2 eq.) were added successively. The system reacted at room temperature for 2 h. TLC monitored the completion of the reaction. The reaction was quenched by adding water, then ethyl acetate was added, and the solution was then washed with saturated brine. The obtained organic phase was dried, concentrated under reduced pressure, and separated by silica gel column to obtain 58 mg of the target compound as a white solid with a yield of 15%. (ES, m/z): [M+1]$^+$=391, H-NMR: (300 MHz, CDCl$_3$, ppm): δ8.50 (s, 1H), 7.88(dd, J=6.6, 2.7 Hz, 1H), 7.70(s, 1H), 7.44 (s, 1H), 7.37 (m, 1H), 7.16 (t, J=8.4 Hz,1H), 2.81(s, 3H), 2.45 (s, 1H), 1.75 (s, 3H), 1.70 (s, 3H).

Example 5

2-Methyl-3-amide-N-(3-chloro-4-fluorophenyl)-5-(2-(2-alkynylbutylamino)-oxalyl)-furan (Compound 5)

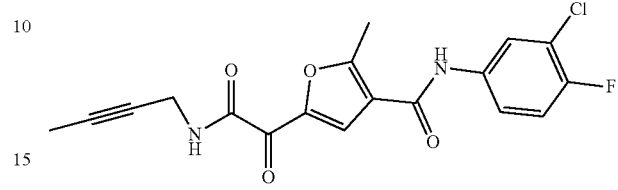

Intermediate I-4 was dissolved in 5 mL DMF, DIPEA (387 mg, 3.0 eq.), 1,1-dimethylpropynamine (104 mg, 1.5 eq.) and HATU (456 mg, 1.2 eq.) were added successively. The system reacted at room temperature for 2h. TLC monitored the completion of the reaction. The reaction was quenched by adding water, then ethyl acetate was added, and then the mixture was washed with saturated brine. The obtained organic phase was dried, concentrated under reduced pressure, and separated by a silica gel column to yield 74 mg of the target compound as an off-white solid with a yield of 20%. (ES, m/z): [M+1]$^+$=377, H-NMR: (400 MHz, DMSO-d$^6$, ppm): δ 10.33 (s, 1H), 9.35(t, J=5.6 Hz, 1H), 8.59(s, 1H), 8.05 (dd, J=6.8, 2.4 Hz, 1H), 7.70 (m, 1H), 7.43 (t, J=9.2 Hz,1H), 3.97(dd, J=5.6, 2.4 Hz, 2H), 2.71 (s, 3H), 1.79 (t, J=2.4 Hz, 3H).

Example 6

2-Methyl-3-amide-N-(3-chloro-4-fluorophenyl)-5-(2-(4-methyl-2-ynylpentylamino)-oxalyl)-furan (Compound 6)

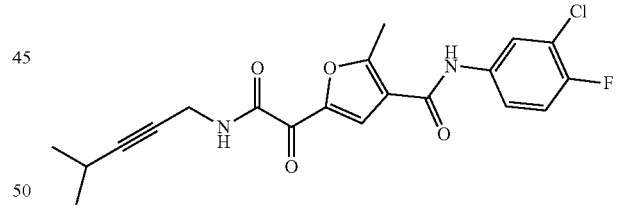

Intermediate I-4 was dissolved in 5 mL DMF, DIPEA (387 mg, 3.0 eq.), 2-(4-methyl-2-ynylpentylamine (146 mg, 1.5 eq.) and HATU (456 mg, 1.2 eq.) were added successively. The mixture reacted at room temperature for 2h. TLC monitored the completion of the reaction. The reaction was quenched by adding water, then ethyl acetate was added, and then the system was washed with saturated brine. The resulting organic phase was dried, concentrated under reduced pressure, and separated by a silica gel column. Obtain 102 mg of the target compound as a white solid with a yield of 25%. (ES, m/z): [M+1]$^+$=405, H-NMR: (300 MHz, DMSO-d$^6$, ppm): δ10.33 (s, 1H), 9.33(t, J=5.4 Hz, 1H), 8.58(s, 1H), 8.05 (dd, J=6.9, 2.4 Hz, 1H), 7.70 (m, 1H), 7.42 (t, J=9.0 Hz ,1H), 4.00(dd, J=5.7, 1.8 Hz, 2H), 2.71 (s, 3H), 2.60 (m, 1H), 1.12(s,3H), 1.10(s,3H).

Example 7

2-Methyl-3-amide-N-(3-chloro-4-fluorophenyl)-5-(2-(3-phenyl-2-eynylpropylamino)-oxalyl)-furan (Compound 7)

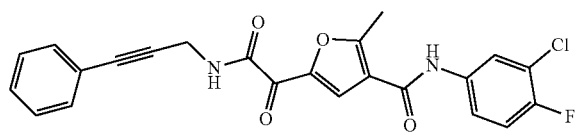 [SMILES: Cc1oc(C(=O)C(=O)NCC#Cc2ccccc2)cc1C(=O)Nc1ccc(F)c(Cl)c1]

Intermediate I-4 was dissolved in 5 mL DMF, DIPEA (387 mg, 3.0 eq.), 3-phenyl-2-alkynylpropylamine (196 mg, 1.5 eq.) and HATU (456 mg, 1.2 eq.) were added successively, and then the system reacted at room temperature for 2 h. TLC monitored the completion of the reaction. The reaction was quenched by adding water, then ethyl acetate was added, and then the mixture was washed with saturated brine. The obtained organic phase was dried, concentrated under reduced pressure, and separated by a silica gel column to obtain 86 mg of the target compound as a white solid with a yield of 20%. (ES, m/z): [M+1]$^+$=439, H-NMR: (300 MHz, DMSO-d$^6$, ppm): δ10.33 (s, 1H), 9.53(t, J=5.7 Hz, 1H), 8.62(s, 1H), 8.05 (dd, J=6.9, 2.4 Hz, 1H), 7.70 (m, 1H), 7.42 (m,6H), 4.29(d, J=5.7 Hz, 2H), 2.72 (s, 3H).

Example 8

2-Methyl-3-amide-N-(3-chloro-4-fluorophenyl)-5-(2-(1-methyl-imidazol-2-)methylamino)-oxalyl)-furan (Compound 8)

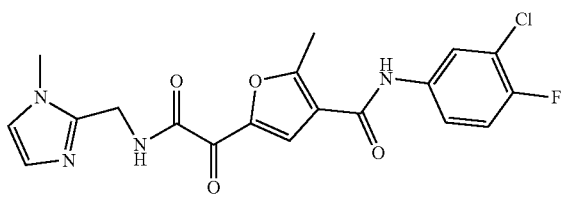 [SMILES: Cc1oc(C(=O)C(=O)NCc2nccn2C)cc1C(=O)Nc1ccc(F)c(Cl)c1]

Intermediate I-4 was dissolved in 5 mL DMF, DIPEA (387 mg, 3.0 eq.) and (1-methyl-imidazol-2-yl) methylamine (166 mg, 1.5 eq.) were added successively, and then HATU (456 mg, 1.2 eq.) was added and the system reacted at room temperature for 2 h. TLC monitored the completion of the reaction. The reaction was quenched by adding water, then ethyl acetate was added, and then the system was washed with saturated brine. The obtained organic phase was dried and concentrated under reduced pressure, and prepared by high performance liquid phase to obtain 16 mg of the target compound as a pale yellow solid with a yield of 4%. (ES, m/z): [M+1]$^+$=419, H-NMR: (300 MHz, DMSO-d$^6$, ppm): δ10.36 (s, 1H), 9.36(t, J=6.0 Hz, 1H), 8.58(s, 1H), 8.05 (dd, J=6.9, 2.4 Hz, 1H), 7.70 (m, 1H), 7.46 (d, J=9.2 Hz, 1H), 7.09(s, 1H), 6.80 (s, 1H), 4.47(d, J=5.7 Hz, 2H), 3.89 (s, 3H), 2.71 (s, 3H).

Example 9

2-Methyl-3-amide-N-(3-chloro-4-fluorophenyl)-5-(2-anilino-oxalyl)-furan (Compound 9)

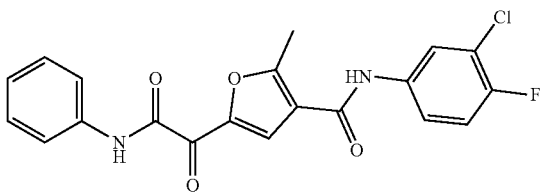 [SMILES: Cc1oc(C(=O)C(=O)Nc2ccccc2)cc1C(=O)Nc1ccc(F)c(Cl)c1]

Intermediate I-4 was dissolved in 5 mL DMF, DIPEA (387 mg, 3.0 eq.) and aniline (140 mg, 1.5 eq.) were added successively, then HATU (456 mg, 1.2 eq.) was added and the mixture reacted at room temperature for 2 h. TLC monitored the completion of the reaction. The reaction was quenched by adding water, then ethyl acetate was added, and then the system was washed with saturated brine. The obtained organic phase was dried and concentrated under reduced pressure, and prepared by high performance liquid phase to give 35 mg of the target compound as a pale yellow solid with a yield of 9%. (ES, m/z): [M+1]$^+$=401, H-NMR: (300 MHz, DMSO-d$^6$, ppm): δ10.89 (s, 1H), 10.36 (s, 1H), 8.63 (s , 1H), 8.05 (dd, J=6.9, 2.7 Hz, 1H), 7.78 (d, J=7.8 Hz, 1H), 7.70 (m, 1H), 7.40 (m, 3H), 7.18 (t, J=7.2 Hz, 2H), and 2.74 (s, 3H).

Example 10

2-Methyl-3-amide-N-(3-chloro-4-fluorophenyl)-5-(2-(1-allyl-1H-[1,2,3]-triazole-4-methylamino)-oxalyl)-furan (Compound 10)

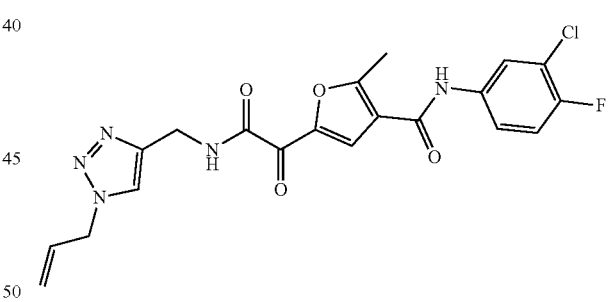

Intermediate I-4 was dissolved in 5 mL DMF, and DIPEA (387 mg, 3.0 eq.), 1-allyl-1H-[1,2,3]triazol-4-yl)methylamine (207 mg, 1.5 eq.), and HATU (456 mg, 1.2 eq.) were added and the system reacted at room temperature for 2 h. TLC monitored the completion of the reaction. The reaction was quenched by adding water, then ethyl acetate was added, and then the system was washed with saturated brine. The obtained organic phase was dried and concentrated under reduced pressure, and prepared by high performance liquid phase to obtain 35 mg of the target compound as a pale yellow solid with a yield of 8%. (ES, m/z): [M+1]$^+$=446, H-NMR: (300 MHz, DMSO-d$^6$, ppm): δ10.33 (s, 1H), 9.47(d, J=6.0 Hz, 1H), 8.60 (s, 1H), 8.06(dd, J=6.9, 2.4 Hz, 1H), 8.04(s, 1H), 7.71(m, 1H), 7.42(t, J=9.0 Hz, 1H), 6.04(m, 1H), 5.23(m, 2H), 5.00(d, J=2.7 Hz, 2H), 4.48(d, J=6.0 Hz, 2H), and 2.71 (s, 3H).

Example 11

2-Methyl-3-amide-N-(3-chloro-4-fluorophenyl)-5-(2-(1-cyclopropyl-1H-[1, 2, 3] triazole-4-ylmethyl-amino)-oxalyl)-furan (Compound 11)

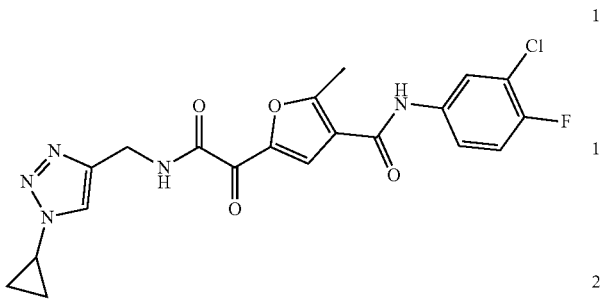

Intermediate I-4 was dissolved in 5 mL DMF, and DIPEA (387 mg, 3.0 eq.), 1-cyclopropyl-1H-[1,2,3]triazol-4-yl)methylamine (207 mg, 1.5 eq.), and HATU (456 mg, 1.2 eq.) were added and the mixture reacted at room temperature for 2 h. TLC monitored the completion of the reaction. The reaction was quenched by adding water, then ethyl acetate was added, and then the system was washed with saturated brine. The obtained organic phase was dried and concentrated under reduced pressure, and then prepared by high performance liquid phase to obtain 5 mg of the target compound as a pale yellow solid with a yield of 1%. (ES, m/z): $[M+1]^+$=446. H-NMR: (300 MHz, DMSO-$d^6$, ppm): δ 10.34 (s, 1H), 9.47(s, 1H), 8.60(s, 1H), 8.05(dd, J=6.9, 2.4 Hz, 1H), 7.95(s, 1H), 7.71 (m, 1H), 7.42(t, J=9.0 Hz, 2H), 6.04(m, 1H), 5.25(m, 2H), 5.00(m, 2H), 4.49(d, J=6.0 Hz, 2H), and 2.71(s, 3H).

Example 12

2-Methyl-3-amide-N-(3-chloro-4-fluorophenyl)-5-(2-(thiazol-2-amino)-oxalyl)-furan (Compound 12)

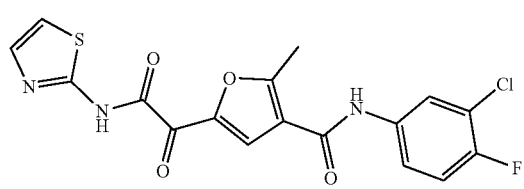 [SMILES: Cc1oc(C(=O)C(=O)Nc2nccs2)cc1C(=O)Nc1ccc(F)c(Cl)c1]

Dissolve Intermediate I-4 in 5 mL DMF, add DIPEA (387 mg, 3.0 eq.), 2-aminothiazole (150 mg, 1.5 eq.), and then HATU (456 mg, 1.2 eq.) at room temperature. Reaction for 2 h. TLC monitored the completion of the reaction. The reaction was quenched by adding water, then ethyl acetate was added, and then the system was washed with saturated brine. The obtained organic phase was dried and concentrated under reduced pressure, and prepared by high performance liquid phase to obtain 7 mg of the target compound as a pale yellow solid with a yield of 2%. (ES, m/z): $[M+1]^+$=408.

Example 13

2-Methyl-3-amide-N-(3-chloro-4-fluorophenyl)-5-(2-(3-methyl-3-oxetanino)-oxalyl)-furan (Compound 13)

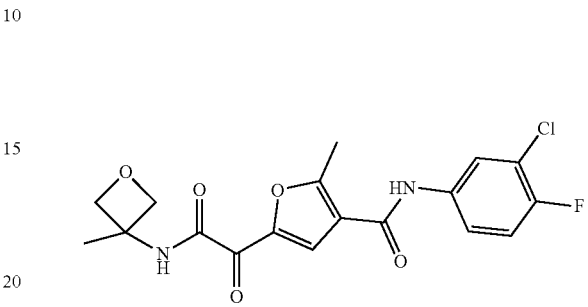

Intermediate I-4 was dissolved in 5 mL DMF, DIPEA (387 mg, 3.0 eq.) and 3-methyl-3-oxetanamine (130 mg, 1.5 eq.) were added successively, and then HATU (456 mg, 1.2 eq.) was added and the system reacted at room temperature for 2 h. TLC monitored the completion of the reaction. The reaction was quenched by adding water, then ethyl acetate was added, and then the mixture was washed with saturated brine. The obtained organic phase was dried, concentrated under reduced pressure, and separated by a silica gel column to obtain 40 mg of the target compound as a pale yellow solid with a yield of 10%. (ES, m/z): $[M+1]^+$=395.

Example 14

2-Methyl-3-amide-N-(3-chloro-4-fluorophenyl)-5-(2-cyclopentylamino-oxalyl)-furan (14)

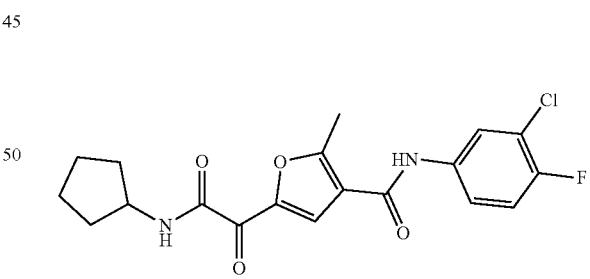

Intermediate I-4 was dissolved in 5 mL DMF, DIPEA (387 mg, 3.0 eq.) and cyclopentylamine (128 mg, 1.5 eq.) were added successively, then HATU (456 mg, 1.2 eq.) was added and the mixture reacted at room temperature 2h. TLC monitored the completion of the reaction. The reaction was quenched by adding water, then ethyl acetate was added, and then the system was washed with saturated brine. The obtained organic phase was dried, concentrated under reduced pressure, and separated by a silica gel column to obtain 36 mg of the target compound as a pale white solid with a yield of 9%. (ES, m/z): $[M+1]^+$=393.

Example 15

2-Methyl-3-amide-N-(3-chloro-4-fluorophenyl)-5-(2-((S)-1,1,1-trifluoropropan-2-amine)-oxalyl)-furan (15)

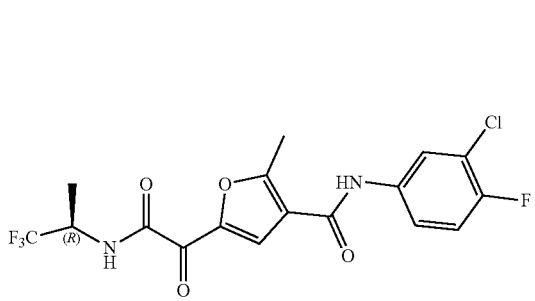

Dissolve Intermediate I-4 in 5 mL DMF, add DIPEA (387 mg, 3.0 eq.), (S)-1,1,1-trifluoropropan-2-amine (170 mg, 1.5 eq.) successively, then HATU (456 mg, 1.2 eq.) was added and the mixture reacted at room temperature for 2 h. TLC monitored the completion of the reaction. The reaction was quenched by adding water, then ethyl acetate was added, and then the system was washed with saturated brine. The obtained organic phase was dried, concentrated under reduced pressure, and was separated by silica gel column to obtain 53 mg of the target compound as a pale yellow solid with a yield of 13%. (ES, m/z): [M+1]$^+$=421.

Example 16

2-Methyl-3-amide-N-(3-chloro-4-fluorophenyl)-5-(2-(1-trifluoromethyl-cyclopropylamino)-oxalyl)-furan (16)

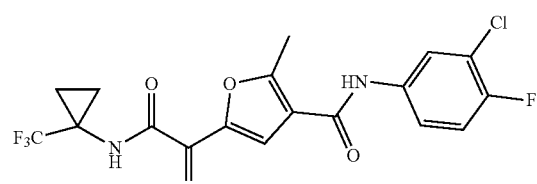

Intermediate I-4 was dissolved in 5 mL DMF, DIPEA (387 mg, 3.0 eq.) and 1-trifluoromethyl-cyclopropylamine (188 mg, 1.5 eq.) were added successively, and then HATU (456 mg, 1.2 eq.).) was added; the system reacted at room temperature for 2 h. TLC monitored the completion of the reaction. The reaction was quenched by adding water, then ethyl acetate was added, and the mixture was washed with saturated brine. The obtained organic phase was dried, concentrated under reduced pressure, and separated by silica gel column to obtain 76 mg of the target compound as a pale yellow solid with a yield of 18%. (ES, m/z): [M+1]$^+$=433.

Example 17

2-Methyl-3-amide-N-(3-chloro-4-fluorophenyl)-5-(2-(1H-1,2,3-triazole-4-methylamino)-oxalyl)-furan (Compound 17)

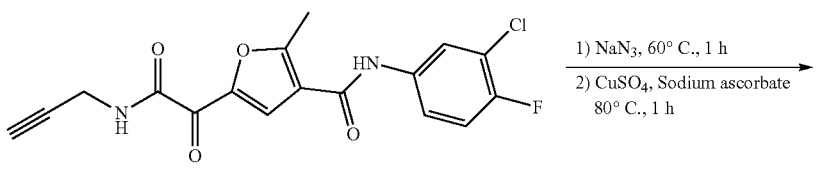

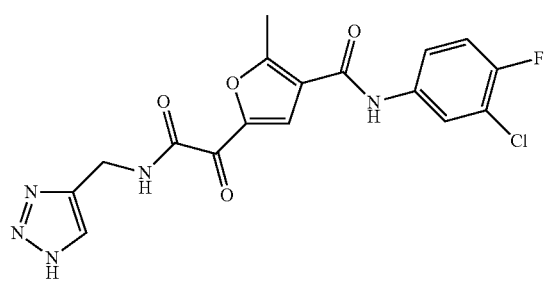

2 (300 mg, 1.0 eq.) was dissolved in 5 mL acetonitrile, NaN$_3$ (376 mg, 7.0 eq.) was added to the reaction solution that was heated to 60□ for 1 h, then was cooled to room temperature, and CuSO$_4$ and sodium ascorbate were added, the reation took place at 80□ for 1 h, the reaction solution was poured into saturated NH$_4$Cl, and the organic phase obtained by EA extraction of three times was dried and concentrated under reduced pressure. The target compound was separated by silica gel column to obtain 40 mg white solid of the target compound with a yield of 10%. (ES, m/z): [M+1]$^+$=406, H-NMR: (300 MHz, DMSO-d$^6$, ppm): δ14.80 (b, 1H), 10.33 (s, 1H), 9.49(b , 1H), 8.60 (s, 1H), 8.05 (dd, J=6.9, 2.7 Hz, 1H), 7.70 (m, 2H), 7.42 (t, J=9.0 Hz, 1H), 4.50 (d, J=5.4 Hz, 2H), and 2.71 (s, 3H).

Example 18 to Example 28 were Synthesis According to the Specific Route shown in Scheme 1 below

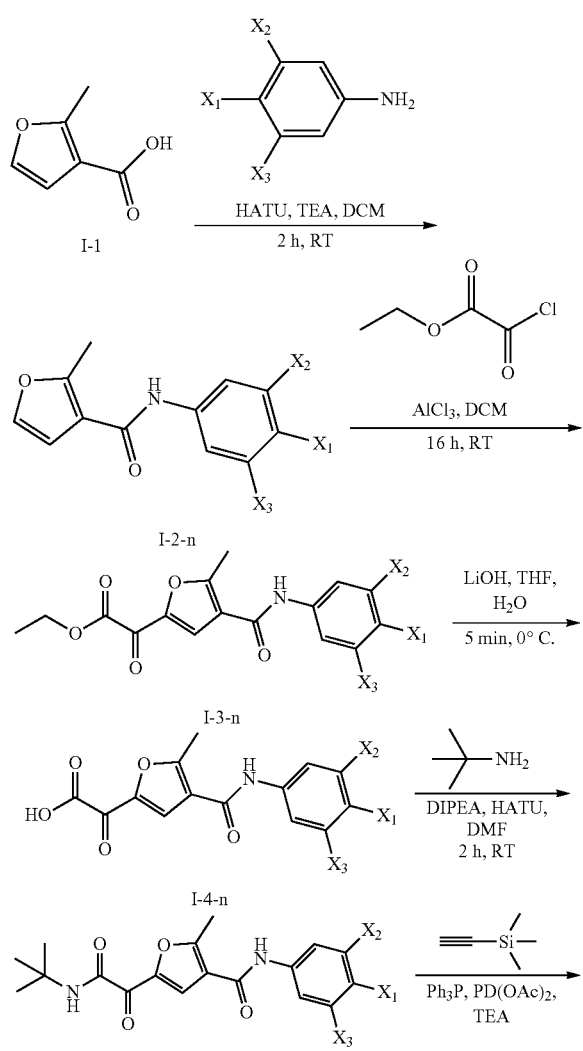

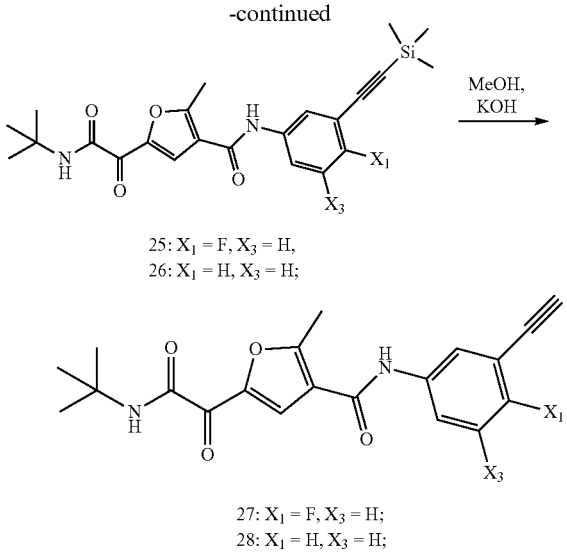

25: X$_1$ = F, X$_3$ = H,
26: X$_1$ = H, X$_3$ = H;

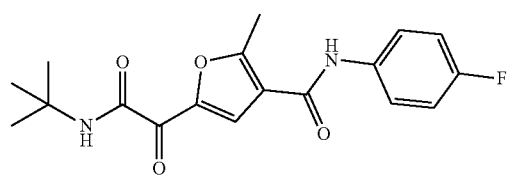 [SMILES: Cc1oc(C(=O)C(=O)NC(C)(C)C)cc1C(=O)Nc1ccc(F)cc1]

27: X$_1$ = F, X$_3$ = H;
28: X$_1$ = H, X$_3$ = H;

Example 18

2-Methyl-3-amide-N-(4-fluorophenyl)-5-(2-tert-butylamino-oxalyl)-furan (Compound 18)

Step 18a: 2-Methyl-3-amide-N-(2-fluorophenyl)-furan (Compound I-2-18)

3-Methylfuran-3-formic acid (I-1, 3.7 g, 1.0 eq.) was dissolved in 150 mL DCM, and TEA (8.1 mL, 3.0 eq.) and HATU (13.4 g, 1.2 eq.) were added with stirring, the system reacted at room temperature for 15 minutes, and then 4-fluoroaniline (6.5 g, 2.0 eq.) was added. The reaction was carried out at room temperature for 2 h, and the reaction was completed as detected by LCMS. The reaction solution was washed with saline and then with water. The mixture was then dried, spin dried, and mixed with sample, then the products ran through the normal phase column. 5.8 g of white solid product was obtained. (ES, m/z): [M+1]$^+$=220.

Step 18b: 2-Methyl-3-amide-N-(2-fluorophenyl)-5-oxalatoethyl-furan (Compound I-3-18)

Under the nitrogen protection, AlCl$_3$ (2.7 g, 4.0 eq.) was dissolved in dichloromethane, the reaction solution was cooled to 0° C., and then ethyl oxalyl chloride (2.7 g, 4.0 eq.) was added while stirring, and stir continued at 0° C. for 30 min. Then I-2-18 (1.1 g, 1.0 eq.) was added to the above reaction solution, and the reaction was allowed to warm up naturally for 16 h. TLC monitored the completion of the reaction. The reaction was quenched by adding dilute hydrochloric acid, and then the system was washed with water and saturated brine. The organic phase was dried and concentrated under reduced pressure, and separated by silica gel column to obtain 1.1 g of the target compound. (ES, m/z): [M+1]⁺=320.

I-3-18 (300 mg, 1.0 eq.) was dissolved in 6 mL of tetrahydrofuran and 2 mL of water, the reaction solution was cooled to 0° C., and LiOH (48 mg, 2.0 eq.) was added. After 5 minutes of reaction, TLC monitored the completion of the reaction. The mixture was concentrated under reduced pressure to remove tetrahydrofuran, pH was adjusted to 3 with 1M dilute hydrochloric acid under ice bath, then the solution was extracted twice with 10 times ethyl acetate. The organic phases were combined, and dried over anhydrous sodium sulfate, and concentrated under reduced pressure, and then was directly used in the next step. (ES, m/z): [M+1]⁺=292.

Step 18d: 2-Methyl-3-amide-N-(3-chloro-4-fluorophenyl)-5-(2-tert-butylamino-oxalyl)-furan (Compound 18)

Intermediate I-4-18 was dissolved in 5 mL DMF, DIPEA (365 mg, 3.0 eq.) and tert-butylamine (104 mg, 1.5 eq.) were added successively, then HATU (396 mg, 1.1 eq.) was added and the mixture reacted at room temperature for 2 h. TLC monitored the completion of the reaction. The reaction was quenched by adding water, then ethyl acetate was added, and then the solution was washed with saturated brine. The obtained organic phase was dried, concentrated under reduced pressure, and separated by silica gel column to obtain 90 mg of the target compound as a white solid. (ES, m/z): [M+1]⁺=347, H-NMR: (300 MHz, CDCl₃, ppm): δ8.42 (s, 1H), 7.57 (dt, J=6.9, 4.2 Hz, 2H), 7.50(s, 1H), 7.09 (t, J=4.2 Hz, 2H), 2.84(s, 3H), and 1.48 (s, 9H).

Example 19

2-Methyl-3-amide-N-(3,4-difluorophenyl)-5-(2-tert-butylamino-oxalyl)-furan (Compound 19)

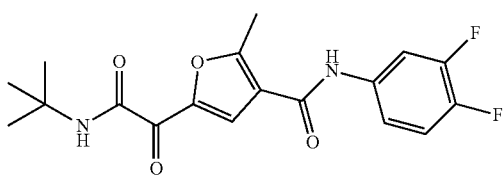 [SMILES: Cc1oc(C(=O)C(=O)NC(C)(C)C)cc1C(=O)Nc1ccc(F)c(F)c1]

According to the synthesis route and reaction conditions of Example 18, in step 19a, the raw material was replaced by 3,4-difluoroaniline, and Compound 19 was synthesized. The total yield was 15%. (ES, m/z): [M+1]⁺=365, H-NMR: (400 MHz, CDCl₃, ppm): δ 8.43 (s, 1H), 7.76 (dt, J =11.2, 7.6 Hz, 1H), 7.62(s, 1H), 7.24(s, 1H), 7.17 (m, 2H), 2.82(s, 3H), 1.48 (s, 9H).

Example 20

2-Methyl-3-amide-N-(3,4,5-trifluorophenyl)-5-(2-tert-butylamino-oxalyl)-furan (Compound 20)

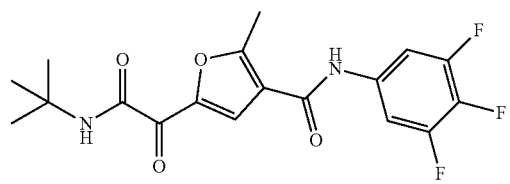 [SMILES: Cc1oc(C(=O)C(=O)NC(C)(C)C)cc1C(=O)Nc1cc(F)c(F)c(F)c1]

According to the synthesis route and reaction conditions of Example 18, in step 19a, the raw material was replaced with 3,4-difluoroaniline, and Compound 19 was synthesized. The total yield was 15%. (ES, m/z): [M+1]⁺=365, H-NMR: (400 MHz, CDCl₃, ppm): δ 8.43 (s, 1H), 7.76 (dt, J =11.2, 7.6 Hz, 1H), 7.62(s, 1H), 7.24(s, 1H), 7.17 (m, 2H), 2.82(s, 3H), 1.48 (s, 9H).

Example 20

2-Methyl-3-amide-N-(3,4,5-trifluorophenyl)-5-(2-tert-butylamino-oxalyl)-furan (Compound 20)

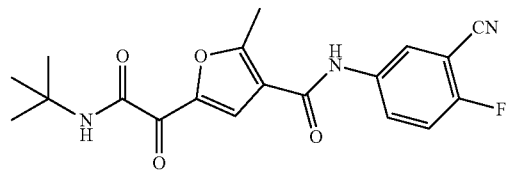 [SMILES: Cc1oc(C(=O)C(=O)NC(C)(C)C)cc1C(=O)Nc1ccc(F)c(C#N)c1]

According to the synthetic route and reaction conditions of Example 18, in step 21a, the raw material was replaced with 3-cyano-4-fluoroaniline, and Compound 21 was synthesized. The total yield was 11%. (ES, m/z): [M+1]⁺=372, H-NMR: (400 MHz, CDCl₃, ppm): δ8.43 (s, 1H), 7.75 (dt, J =8.4, 4.8 Hz, 1H), 7.60(s, 1H), 7.22(m, 1H), 7.17 (m, 2H), 2.82(s, 3H), and 1.48 (s, 9H).

Example 22

2-Methyl-3-amide-N-(4-trifluoromethylphenyl)-5-(2-tert-butylamino-oxalyl)-furan (Compound 22)

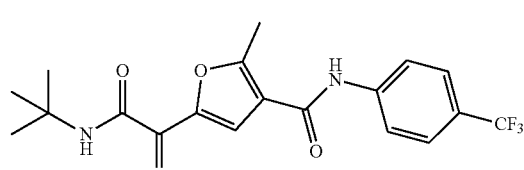

According to the synthesis route and reaction conditions of Example 18, the raw material was replaced with 4-trif luoromethylaniline in step 22a, and Compound 22 was synthesized. The total yield was 11%. (ES, m/z): [M+1]⁺=397, H-NMR: (300 MHz, CDCl₃, ppm): δ8.46(s, 1H), 7.76(d, J=8.4 Hz, 1H), 7.65(d, J=8.4 Hz, 1H), 7.23(s, 1H), 2.82(s, 3H), 1.48 (s, 9H).

Example 23

2-Methyl-3-amide-N-(3-bromo-4-fluorophenyl)-5-(2-tert-butylamino-oxalyl)-furan (Compound 23)

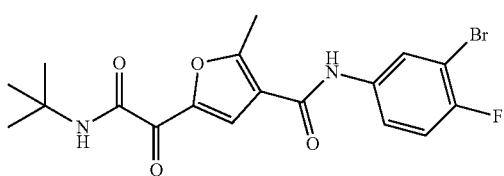 [SMILES: Cc1oc(C(=O)C(=O)NC(C)(C)C)cc1C(=O)Nc1ccc(F)c(Br)c1]

According to the synthetic route and reaction conditions of Example 18, the raw material was replaced with 3-bromo-4-fluoroaniline in step 23a, and Compound 23 was synthesized. The total yield was 12%. (ES, m/z): [M+1]⁺=425, 427.

Example 24

2-Methyl-3-amide-N-(3-iodophenyl)-5-(2-tert-butylamino-oxalyl)-furan (Compound 24)

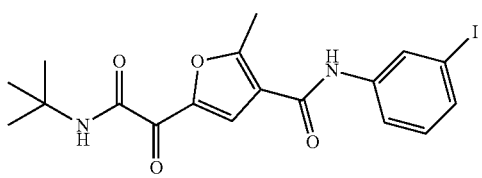 [SMILES: Cc1oc(C(=O)C(=O)NC(C)(C)C)cc1C(=O)Nc1cccc(I)c1]

According to the synthetic route and reaction conditions of Example 18, the raw material was replaced with 3-iodoaniline in step 24a, and Compound 24 was synthesized. The total yield was 12%. The total yield was 13%. (ES, m/z): [M+1]+=455.

Example 25

2-Methyl-3-amide-N-(3-trimethylsilylethynyl-4-fluorophenyl)-5-(2-tert-butylamino-oxalyl)-furan (Compound 25)

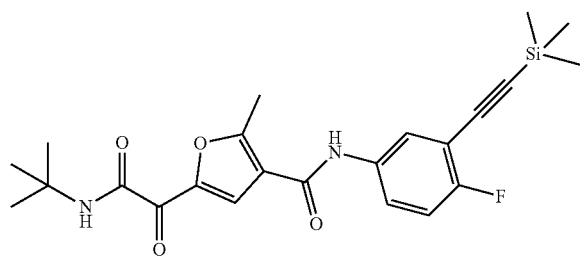 [SMILES: Cc1oc(C(=O)C(=O)NC(C)(C)C)cc1C(=O)Nc1ccc(F)c(C#C[Si](C)(C)C)c1]

Compound 23 (681 mg, 1.0 eq.) was dissolved in 15 mL triethylamine, and then trimethylsilylacetylene (441 mg, 3.0 eq.), Ph₃P (157 mg, 0.4 eq.) and Pd(OAc)₂ (101 mg, 0.3 eq.) were added, the atmosphere was replaced by nitrogen, and the system was heated to 100° C. for reflux and reacted overnight, LCMS detected the completion of the reaction, the reaction solution was filtered and spin-dried, and purified by silica gel column. The obtained product is Compound 25 as a yellow solid of 88 mg. (ES, m/z): [M+1]+=443.

Example 26:

2-Methyl-3-amide-N-(3-trimethylsilylethynylphenyl)-5-(2-tert-butylamino-oxalyl)-furan (Compound 26)

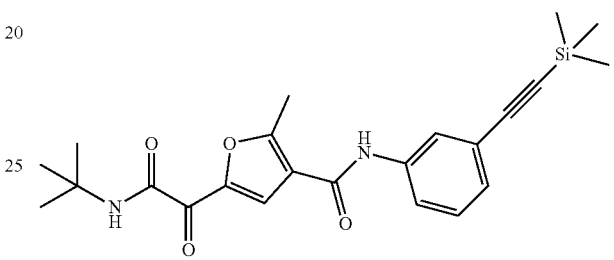

Compound 24 (600 mg, 1.0 eq.) was dissolved in 15 mL triethylamine, trimethylsilylacetylene (415 mg, 3.0 eq.), Ph₃P (148 mg, 0.4 eq.) and Pd(OAc)₂ (94 mg, 0.3 eq.) were added, the atmosphere was replaced with nitrogen, and the system was heated to 100° C. for reflux and reacted overnight, LCMS detected the completion of the reaction, the reaction solution was filtered and spin-dried, and purified by silica gel column. The obtained product is Compound 26 as a white solid of 67 mg. (ES, m/z): [M+1]⁺=425.

Example 27

2-Methyl-3-amide-N-(3-alkynyl-4-fluorophenyl)-5-(2-tert-butylamino-oxalyl)-furan (Compound 27)

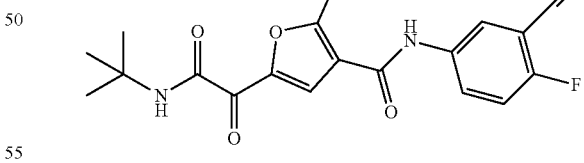

Compound 25 (85 mg, 1.0 eq.) was dissolved in 5 mL methanol, then KOH (13 mg, 1.2 eq.) was added, and the reaction was carried out at room temperature overnight. The reaction was completed by LCMS detection, and the product was purified by silica gel column. The obtained off-white solid is Compound 27. The yield of this step was 14%. (ES, m/z): [M+1]⁺=419, H-NMR: (300 MHz, DMSO-d⁶, ppm): δ10.27 (s, 1H), 8.53(s, 1H), 8.48(s , 1H), 7.99 (m, 1H), 7.78(m, 1H), 7.31(t, J=9.0 Hz, 1H), 4.52(s, 1H), 2.70 (s, 3H), 1.38 (s, 9H) .

Example 28

2-Methyl-3-amide-N-(3-alkynylphenyl)-5-(2-tert-butylamino-oxalyl)-furan (Compound 28)

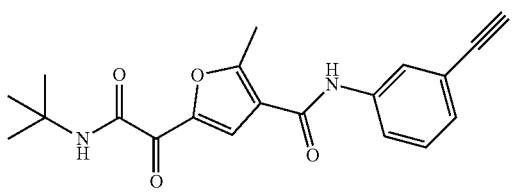 [SMILES: C#Cc1cccc(NC(=O)c2cc(C(=O)C(=O)NC(C)(C)C)oc2C)c1]

Compound 26 (67 mg, 1.0 eq.) was dissolved in 5 mL methanol, then KOH (10 mg, 1.2 eq.) was added, and the reaction was carried out at room temperature overnight. The reaction was completed by LCMS detection and the product was purified by silica gel column. The obtained off-white solid is compound 28. The yield of this step was 17%. (ES, m/z): [M+1]$^+$=353, H-NMR: (300 MHz, DMSO-d$^6$, ppm): δ10.24 (s, 1H), 8.50(s, 1H), 8.23 (s , 1H), 7.93 (s, 1H), 7.78(d, J=8.1 Hz, 1H), 7.37(t, J=7.8 Hz, 1H), 7.22(d, J=7.8 Hz, 1H), 4.20(s , 1H), 2.70 (s, 3H), 1.39 (s, 9H).

Example 29 to Example 41 were synthesis according to the specific route shown in Scheme 1 below

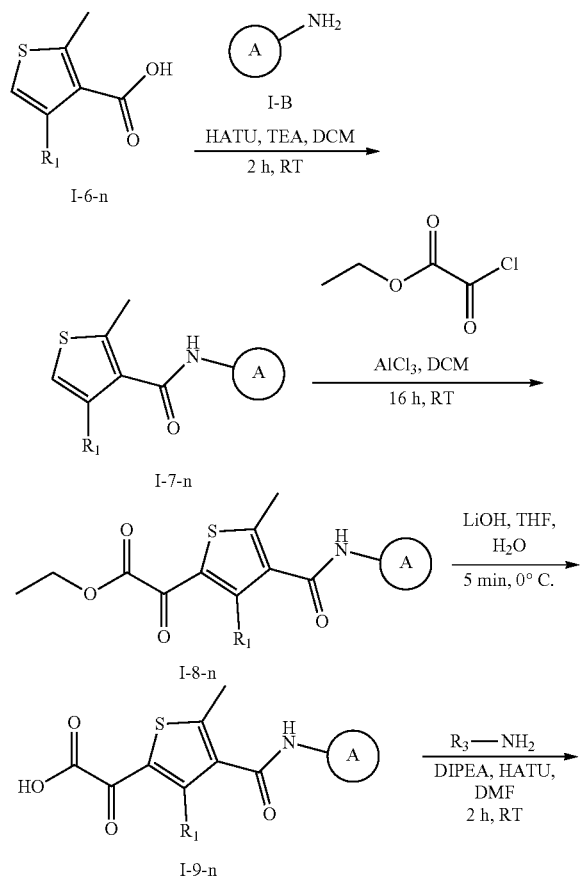

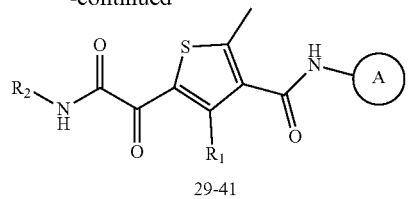
29-41

Example 29

2-Methyl-3-amide-N-(3-chloro-4-fluorophenyl)-5-(2-tert-butylamino-oxalyl)-thiophene (Compound 29)

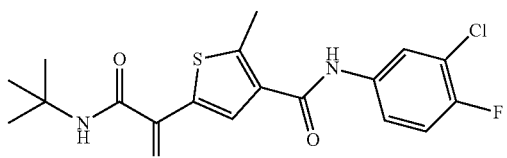

Step 29a: 2-Methyl-3-amide-N-(3-chloro-4-fluorophenyl)-thiophene (Compound I-7-29)

2-Methylthiophene-3-formic acid (I-6, 3.3 g, 1.0 eq.) was dissolved in 300 mL of dichloromethane, and triethylamine (7.0 g, 3.0 eq.) and HATU (10.6 g, 1.2 eq.) were added under stirring. After reacting at room temperature for 5 min, 3-chloro-4-fluoroaniline (4.0 g, 1.2 eq.) was added, and the reaction was carried out at room temperature for 2 h. TLC monitored the completion of the reaction. The reaction was terminated by adding water, then the system was washed with 30 mL of saturated brine by three times, the organic phase was dried and concentrated under reduced pressure, and separated by silica gel column to obtain 1.9 g of the target compound as a white solid with a yield of 30%. (ES, m/z): [M+1]$^+$=270.

Step 29b: 2-Methyl-3-amide-N-(3-chloro-4-fluorophenyl)-5-oxalatoethyl-thiophene (Compound I-8-29)

Under nitrogen protection, dissolve AlCl$_3$ (1.1 g, 4.0 eq.) in dichloromethane, then cool the reaction solution to 0° C., and add ethyl oxalyl chloride (1.1 g, 4.0 eq.) while stirring, and stir at 0° C. for 30 min. Then I-7-29 (538 g, 1.0 eq.) was added to the above reaction solution, and the reaction was allowed to warm up naturally for 16 h. TLC monitored the completion of the reaction. The reaction was quenched by adding dilute hydrochloric acid, and then the solution was washed with water and saturated brine. The organic phase was dried and concentrated under reduced pressure, and separated by a silica gel column to obtain 521 mg of the target compound as a pale yellow solid with a yield of 70%. (ES, m/z): [M+1]$^+$=370.

I-8-29 (369 mg, 1.0 eq.) was dissolved in 6 mL of tetrahydrofuran and 2 mL of water, the reaction solution was cooled to 0° C., and LiOH (84 mg, 2.0 eq.) was added. After 5 minutes of reaction, TLC monitored the completion of the reaction. The solution was concentrated under reduced pressure to remove tetrahydrofuran, the pH was then adjusted to 3 with 1M dilute hydrochloric acid under ice bath, and the solution was extracted twice with 10 times ethyl acetate, the organic phases were combined and dried over anhydrous sodium sulfate, then were concentrated under reduced pressure, and directly used in the next step. (ES, m/z): [M+1]⁺=341.

Step 29d:

2-Methyl-3-amide-N-(3-chloro-4-fluorophenyl)-5-(2-tert-butylamino-oxalyl)-thiophene (Compound 29)

Intermediate I-9-29 was dissolved in 5 mL DMF, DIPEA (387 mg, 3.0 eq.) and tert-butylamine (110 mg, 1.5 eq.) were added successively, then HATU (456 mg, 1.2 eq.) was added and the system reacted at room temperature for 2 h. TLC monitored the completion of the reaction. The reaction was quenched by adding water, then ethyl acetate was added, and the solution was then washed with saturated brine. The obtained organic phase was dried, concentrated under reduced pressure, and separated by silica gel column to obtain 106 mg of the target compound as a white solid with a yield of 27%. (ES, m/z): [M+1]⁺=397, H-NMR: (400 MHz, CDCl₃, ppm): δ8.56 (s, 1H), 7.86 (dd, J=8.8, 3.2 Hz, 1H), 7.23 (s, 1H), 7.42 (b, 1H), 7.14 (m,2H), 2.86 (s, 3H), 1.48 (s, 9H).

Example 30

2-Methyl-3-amide-N-(3-chloro-4-fluorophenyl)-5-(2-propargylamino-oxalyl)-thiophene (Compound 30)

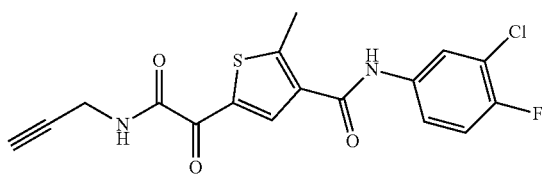 [SMILES: C#CCNC(=O)C(=O)c1cc(C(=O)Nc2ccc(F)c(Cl)c2)c(C)s1]

According to the synthesis route and reaction conditions of Example 29, in step 30d, the raw material was changed to propynylamine to synthesize Compound 30. The total yield was 25%. (ES, m/z): [M+1]⁺=379, H-NMR: (300 MHz, CDCl₃, ppm): δ8.44 (s, 1H), 7.86 (dd, J=7.2, 3.6 Hz, 1H), 7.80 (s, 1H), 7.61 (b, 1H), 7.38 (m, 1H), 7.14 (t, J=3.2 Hz,1H), 4.19 (dd, J=6.6, 3.6 Hz, 2H), 2.80 (s, 3H), 2.33 (t, J=3.6 Hz, 1H).

Example 31

2-Methyl-3-amide-N-(3-chloro-4-fluorophenyl)-5-(2-(3-methyl-3-oxetanino)-oxalyl)-thiophene (compound 31)

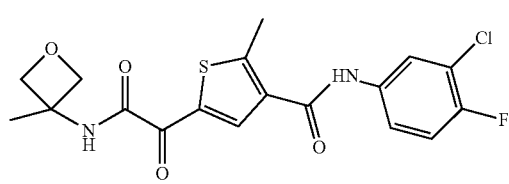 [SMILES: Cc1sc(C(=O)C(=O)NC2(C)COC2)cc1C(=O)Nc1ccc(F)c(Cl)c1]

According to the synthesis route and reaction conditions of Example 29, the raw material was replaced with 3-methyl-3-oxetanamine in step 31d, and Compound 31 was synthesized. The total yield was 25%. The total yield was 9%. (ES, m/z): [M+1]⁺=411.

Example 32

2-Methyl-3-amide-N-(3-chloro-4-fluorophenyl)-5-(2-cyclopentylamino-oxalyl)-thiophene (Compound 32)

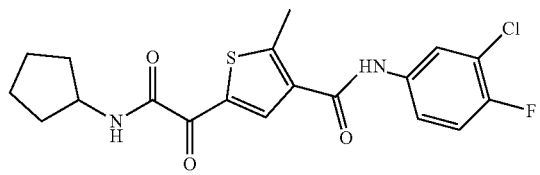 [SMILES: Cc1sc(C(=O)C(=O)NC2CCCC2)cc1C(=O)Nc1ccc(F)c(Cl)c1]

According to the synthesis route and reaction conditions of Example 29, in step 32d, the raw material was replaced with cyclopentylamine, and Compound 32 was synthesized. The total yield was 10%. (ES, m/z): [M+1]⁺=409.

Example 33

2-Methyl-3-amide-N-(3-chloro-4-fluorophenyl)-5-(2-((S)-1,1,1-trifluoropropan-2-amine (Yl)-oxalyl)-thiophene (Compound 33)

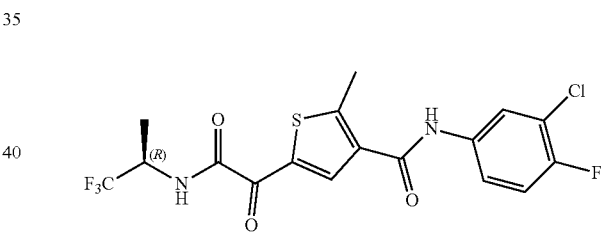

According to the synthetic route and reaction conditions of Example 29, in step 33d, the raw material was replaced with (S)-1,1,1-trifluoropropan-2-amine, and Compound 33 was synthesized. The total yield was 10%. (ES, m/z): [M+1]⁺=437.

Example 34

2-Methyl-3-amide-N-(3,4-difluorophenyl)-5-(2-tert-butylamino-oxalyl)-thiophene (Compound 34)

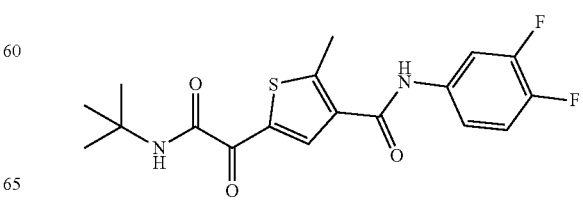

According to the synthetic route and reaction conditions of Example 29, in step 34a, the raw material amine was replaced with 3,4-difluoroaniline, and Compound 34 was synthesized. The total yield was 17%. (ES, m/z): [M+1]⁺=381, H-NMR: (300 MHz, DMSO-d⁶, ppm): δ10.45 (s, 1H), 8.44 (s, 1H), 8.27 (s , 1H), 7.90 (m, 1H), 7.48 (m, 2H), 2.74 (s, 3H), 1.38 (s, 9H).

Example 35

2-Methyl-3-amide-N-(3,4,5-trifluorophenyl)-5-(2-tert-butylamino-oxalyl)-thiophene (Compound 35)

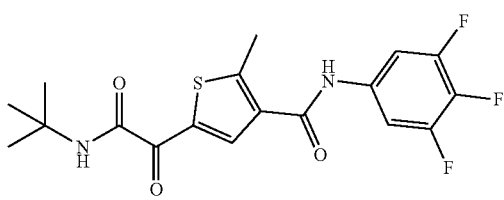 [SMILES: Cc1sc(C(=O)C(=O)NC(C)(C)C)cc1C(=O)Nc1cc(F)c(F)c(F)c1]

According to the synthetic route and reaction conditions of Example 29, in step 35a, the raw material amine was replaced with 3, 4, and 5-trifluoroaniline, and Compound 35 was synthesized. The total yield was 21%. (ES, m/z): [M+1]⁺=399, H-NMR: (300 MHz, DMSO-d⁶, ppm): δ 10.35 (s, 1H), 8.48 (s, 1H), 8.28 (s , 1H), 7.39 (m, 2H), 2.75 (s, 3H), and 1.38 (s, 9H).

Example 36

2,4-Dimethyl-3-amide-N-(3-chloro-4-fluorophenyl)-5-(2-tert-butylamino-oxalyl)-thiophene (Compound 36)

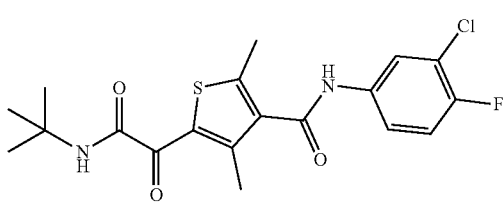 [SMILES: Cc1sc(C(=O)C(=O)NC(C)(C)C)c(C)c1C(=O)Nc1ccc(F)c(Cl)c1]

According to the synthetic route and reaction conditions of Example 29, the starting material 2, 4-dimethylthiophene-3-formic acid (I-6-36) was replaced in step 36a, and Compound 36 was synthesized. The total yield was 16%. (ES, m/z): [M+1]⁺=411, H-NMR: (300 MHz, CDCl₃, ppm): δ7.90 (dd, J=6.3, 2.4 Hz, 1H), 7.56 (s, 1H), 7.51 (m, 1H), 7.32 (s,1H), 7.17 (t, J=8.7 Hz, 1H), 2.62 (d, J=5.4 Hz, 3H), and 1.46 (s, 9H).

Example 37

2,4-Dimethyl-3-amide-N-(3,4-difluorophenyl)-5-(2-(3-methoxymethyl-3-oxetanamine))-oxalyl)-thiophene (Compound 37)

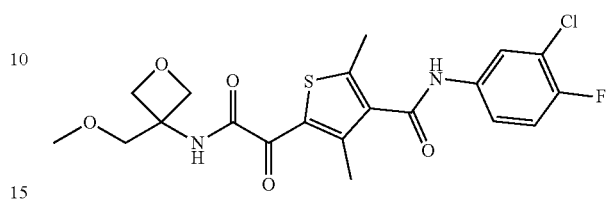

According to the synthetic route and reaction conditions of Example 29, in step 37a, the starting material was replaced with 2, 4-dimethylthiophene-3-formic acid (I-6-37), and the raw material amine was replaced with 3-methoxymethyl-3-oxetanamine, thus the Compound 37 was synthesized. The total yield was 11%. (ES, m/z): [M+1]+=455.

Example 38

2,4-Dimethyl-3-amide-N-(3-chloro-4-fluorophenyl)-5-(2-(1,1-dimethylpropynamido)-oxalyl)-thiophene (Compound 38)

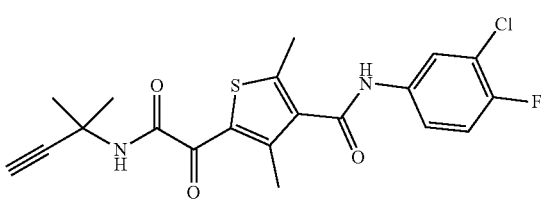 [SMILES: C#CC(C)(C)NC(=O)C(=O)c1sc(C)c(C(=O)Nc2ccc(F)c(Cl)c2)c1C]

According to the synthetic route and reaction conditions of Example 29, in step 38a, the starting material was replaced with 2, 4-dimethylthiophene-3-formic acid (I-6-38), and the raw material amine was replaced with 1,1-dimethyl propargyl amine, and then Compound 38 was synthesized. The total yield was 26%. (ES, m/z): [M+1]⁺=421, H-NMR: (300 MHz, DMSO-d⁶, ppm): δ10.66 (s, 1H), 8.88 (s, 1H), 8.04(dd , J=6.9, 2.4 Hz, 1H), 7.61(m, 1H), 7.44 (t, J=9.0 Hz, 1H), 3.25(s, 1H), 2.73(s, 3H), 2.28(s, 3H) , 1.58 (s, 6H).

Example 39

2,4-Dimethyl-3-amide-N-(benzofuran-5-yl)-5-(2-(1,1-dimethylpropynamido)-oxalyl)-Thiophene (Compound 39)

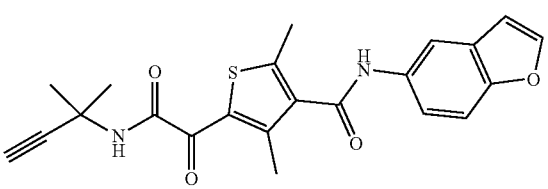 [SMILES: C#CC(C)(C)NC(=O)C(=O)c1sc(C)c(C(=O)Nc2ccc3occc3c2)c1C]

According to the synthetic route and reaction conditions of Example 29, in step 39a, the starting material was replaced with 2, 4-dimethylthiophene-3-formic acid (I-6-39), and the raw material amine was replaced with 1,1-dimethyl propargylamine: In step 39d, the raw material amine was replaced with 5-benzofuranamine to synthesize Compound 39. The total yield was 14%. (ES, m/z): [M+1]+=409.

Example 40

2,4-Dimethyl-3-amide-N-(benzofuran-5)-5-(2-(1-acetylenecyclopropane-1-amino)-oxalyl)-thiophene (Compound 40)

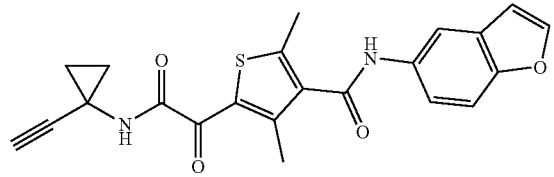 [SMILES: C#CC1(NC(=O)C(=O)c2sc(C)c(C(=O)Nc3ccc4occc4c3)c2C)CC1]

According to the synthetic route and reaction conditions of Example 29, in step 40a, the starting material was replaced with 2, 4-dimethylthiophene-3-formic acid (I-6-40), and the raw material amine was replaced with 1-acetylene cyclopropane-1-amine; in step 40d, the raw material amine was replaced with 5-benzofuranamine to synthesize Compound 40. The total yield was 14%. (ES, m/z): [M+1]$^+$=407.

Example 41

2,4-Dimethyl-3-amide-N-(benzofuran-5-yl)-5-(2-(3-methoxymethyl-3-oxetanyl))-oxalyl)-thiophene (Compound 41)

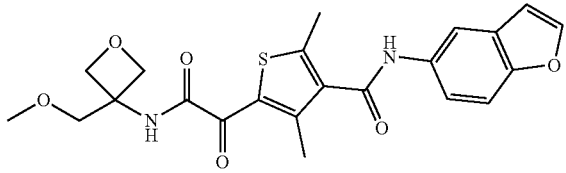 [SMILES: COCC1(NC(=O)C(=O)c2sc(C)c(C(=O)Nc3ccc4occc4c3)c2C)COC1]

According to the synthetic route and reaction conditions of Example 29, in step 41a, the starting material was replaced with 2, 4-dimethylthiophene-3-formic acid (I-6-41), and the raw material amine was replaced with 3-methoxy methyl-3-oxetanamine: In step 41d, the raw material amine was replaced with 5-benzofuranamine to synthesize Compound 41. The total yield was 15%. (ES, m/z): [M+1]$^+$=443.

Example 42 to Example 43 were synthesized according to the specific route shown in Scheme 1 below

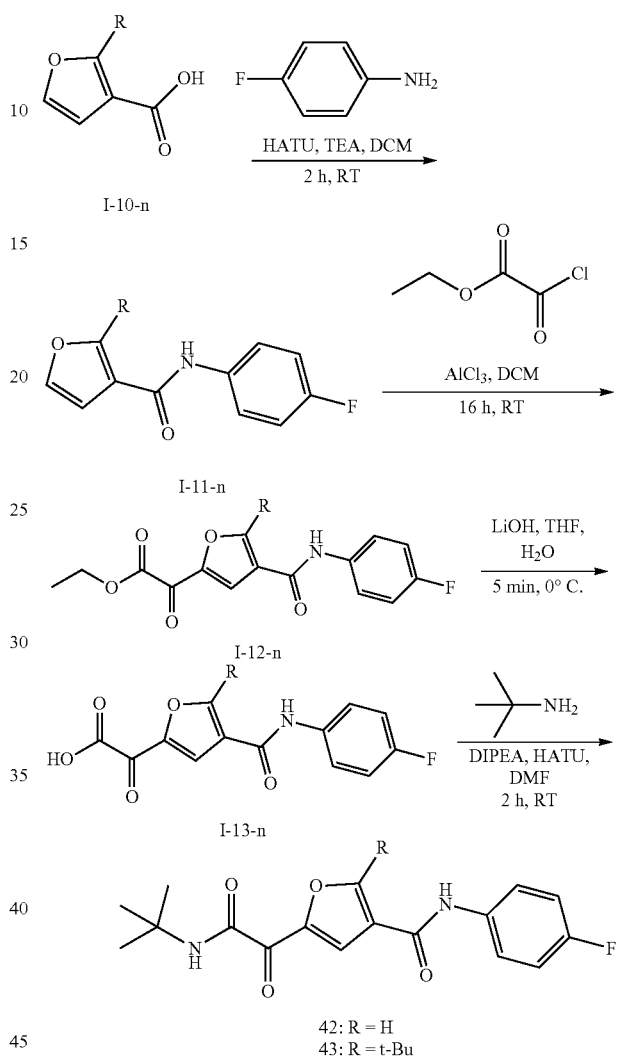

Example 42

3-Amide-N-(4-fluorophenyl)-5-(2-tert-butylamino-oxalyl)-furan (Compound 42)

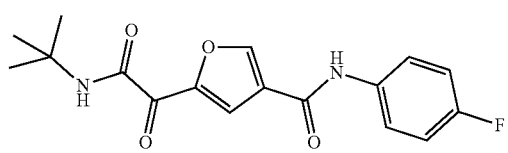 [SMILES: CC(C)(C)NC(=O)C(=O)c1cc(C(=O)Nc2ccc(F)cc2)co1]

Step 42a: 3-Amide-N-(4-fluorophenyl)-furan (Compound I-11-42)

4-Formic acid furan (I-10-42, 2.6 g, 1.0 eq.) was dissolved in 120 mL DCM, TEA (6.5 mL, 3.0 eq.) and HATU (10.7 g, 1.2 eq.) were added with stirring, and the system reacted at room temperature for 15 min., then 4-fluoroaniline (5.2 g, 2.0 eq.) was added. The reaction was carried out at room temperature for 2 h, and the reaction was completed as detected by LCMS. The reaction solution was washed with saline and then with water. The product solution was dried, spin dried and mixed with sample, and then ran through the normal phase column. The product was obtained as a white solid at 4.3 g. (ES, m/z): [M+1]$^+$=206.

Step 42 b: 3-Amide-N-(4-fluorophenyl)-5-oxalato-ethyl-furan (Compound I-12-42)

Under nitrogen protection, AlCl$_3$ (1.8 g, 4.0 eq.) was dissolved in dichloromethane, the reaction solution was cooled to 0° C., then ethyl oxalyl chloride (1.8 g, 4.0 eq.) was added while stirring, and the mixture was stirred at 0° C. for 30 min. Then I-11-42 (0.71 g, 1.0 eq.) was added to the above reaction solution, and the reaction was allowed to warm up naturally for 16 h. TLC monitored the completion of the reaction. The reaction was quenched by adding dilute hydrochloric acid, and then the mixture was washed with water and saturated brine. The organic phase was dried and concentrated under reduced pressure, and separated by silica gel column to obtain 756 mg of the target compound. (ES, m/z): [M+1]$^+$=306.

Step 42c: 3-Amide-N-(4-fluorophenyl)-5-oxalato-ethyl-furan (Compound I-12-42)

Under nitrogen protection, AlCl$_3$ (1.8 g, 4.0 eq.) was dissolved in dichloromethane, the reaction solution was cooled to 0° C., ethyl oxalyl chloride (1.8 g, 4.0 eq.) was added while stirring, and the mixture was stirred at 0° C. for 30 min. Then I-11-42 (0.71 g, 1.0 eq.) was added to the above reaction solution, and the reaction was allowed to warm up naturally for 16 h. TLC monitored the completion of the reaction. The reaction was quenched by adding dilute hydrochloric acid, and then the mixture was washed with water and saturated brine. The organic phase was dried and concentrated under reduced pressure, and separated by silica gel column to obtain 756 mg of the target compound. (ES, m/z): [M+1]$^+$=306.

Step 42d: 3-Amide-N-(4-fluorophenyl)-5-(2-tert-butylamino-oxalyl)-furan (Compound 42)

Intermediate I-13-42 was dissolved in 5 mL DMF, DIPEA (387 mg, 3.0 eq.) and tert-butylamine (110 mg, 1.5 eq.) were added successively, then HATU (456 mg, 1.2 eq.) was added and the system reacted at room temperature for 2 h. TLC monitored the completion of the reaction. The reaction was quenched by adding water, then ethyl acetate was added, and then the mixture was washed with saturated brine. The obtained organic phase was dried, concentrated under reduced pressure, and separated by silica gel column to obtain 79 mg of the target compound as a white solid. (ES, m/z): [M+1]$^+$=333, H-NMR: (300 MHz, CDCl$_3$, ppm): δ8.48 (s, 1H), 8.37 (s, 1H), 7.71 (s, 1H), 7.60 (m, 2H), 7.18 (s,1H), 7.10 (t, J=8.7 Hz, 2H), 1.48 (s, 9H).

Example 43

2-tert-Butyl-3-amide-N-(4-fluorophenyl)-5-(2-tert-butylamino-oxalyl)-furan (Compound 43)

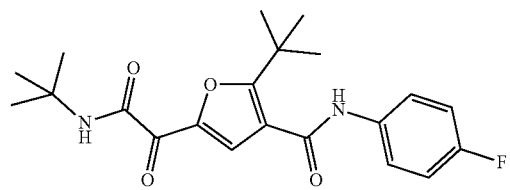 [SMILES: CC(C)(C)NC(=O)C(=O)c1cc(C(=O)Nc2ccc(F)cc2)c(C(C)(C)C)o1]

According to the synthetic route and reaction conditions of Example 42, the starting material was replaced with 2-tert-butylthiophene-3-formic acid (I-6-43) in step 42a, and Compound 43 was synthesized. The total yield was 13%. (ES, m/z): [M+1]$^+$=389, H-NMR: (300 MHz, CDCl$_3$, ppm): δ 8.35 (s, 1H), 7.61 (s, 1H), 7.56 (m, 2H), 7.19 (s,1H), 7.08 (t, Jcl32 8.7 Hz, 2H), 1.52 (s, 9H), 1.46 (s, 9H).

Example 44 to Example 48 were synthesis according to the specific route shown in Scheme 2 below

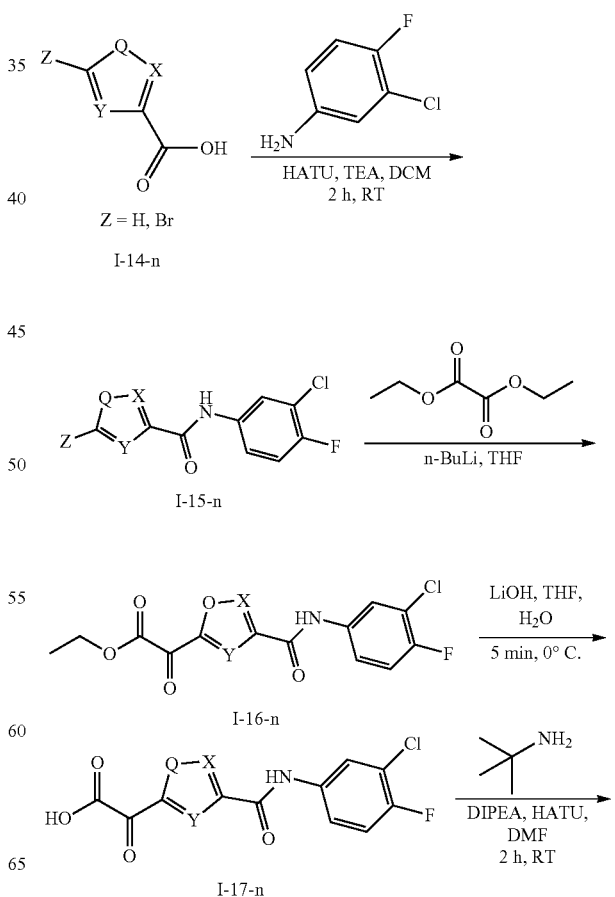

-continued

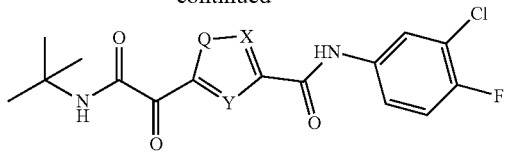

44: Q = S, X = CH, Y = N;
45: Q = S, X = C—CH₃, Y = N;
46: Q = O, X = CH, Y = N;
47: Q = O, X = C—CH₃, Y = N;
48: Q = O, X = N, Y = CH

Example 44

2-(2-Tert-Butylamino-oxalyl)-4-amide-N-(3-chloro-4-fluoro-phenyl)-thiazole (44)

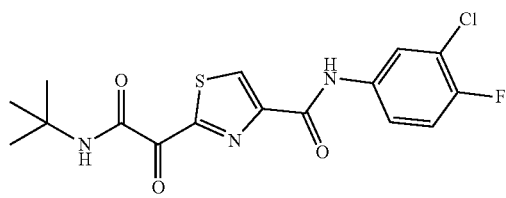 [SMILES: CC(C)(C)NC(=O)C(=O)c1nc(C(=O)Nc2ccc(F)c(Cl)c2)cs1]

Step 44a: 2-Bromo-4-amide-N-(3-chloro-4-fluoro-phenyl)-thiazole (Compound I-15-44)

2-Bromothiazole-4-carboxylic acid (I-14-44, 1.04 g, 1.0 eq.) was dissolved in 300 mL of dichloromethane, and triethylamine (1.5 g, 3.0 eq.) and HATU (2.3 g, 1.2 eq.) were added with stirring. After reacting at room temperature for 5 min, 3-chloro-4-fluoroaniline (0.9 g, 1.2 eq.) was added, and the reaction was carried out at room temperature for 2 h. TLC monitored the completion of the reaction. The reaction was terminated by adding water, and the mixture was washed with 30 mL of saturated brine by three times, the organic phase was dried and concentrated under reduced pressure, and separated by silica gel column to obtain 1.1 g of the target compound with a yield of 65%. (ES, m/z): [M+1]⁺=335, 337.

Step 44b: 2-Oxalatoethyl-4-amide-N-(3-chloro-4-fluorophenyl)-thiazole (I-16-44)

Under the protection of nitrogen, I-15-44 (1.0 g, 1.0 eq.) was dissolved in THF, the reaction solution was cooled to −78 ¤, and 1N n-BuLi solution (3.6 mL, 1.2 eq.) was slowly added dropwise with stirring. Keep stirring at −78° C. for 30 min, then slowly add diethyl oxalate (0.9 g, 2.0 eq.) dropwise to the above reaction solution, keep stirring at −78° C. for 30 min, and the system was naturally warmed to room temperature. The reaction was quenched by adding saturated ammonium chloride solution, and then the organic phase was extracted with ethyl acetate. The organic phase was dried and concentrated under reduced pressure, and separated by silica gel column to obtain 250 mg of the target compound with a yield of 23%. (ES, m/z): [M+1]⁺=357.

Step 44c: 2-Oxalo-4-amide-N-(3-chloro-4-fluorophenyl)-thiazole (I-17-44)

I-16-44 (240 mg, 1.0 eq.) was dissolved in 6 mL of tetrahydrofuran and 2 mL of water, the reaction solution was cooled to 0° C., and LiOH (32 mg, 2.0 eq.) was added. After 5 minutes of reaction, TLC monitored the completion of the reaction. The solution was concentrated under reduced pressure to remove tetrahydrofuran, and the pH was adjusted to 3 with 1M dilute hydrochloric acid under ice bath, then the solution was extracted twice with 10 times ethyl acetate, the organic phases were combined and then dried over anhydrous sodium sulfate, and again concentrate under reduced pressure, and was then directly used in the next step. (ES, m/z): [M+1]⁺=329.

Step 44d: 2-(2-Tert-Butylamino-oxalyl)-4-amide-N-(3-chloro-4-fluoro-phenyl)-thiazole (Compound 44)

Intermediate I-17-44 was dissolved in 5 mL DMF, DIPEA (259 mg, 3.0 eq.) and tert-butylamine (73 mg, 1.5 eq.) were added successively, then HATU (305 mg, 1.2 eq.) was added and the system reacted at room temperature for 2 h. TLC monitored the completion of the reaction. The reaction was quenched by adding water, then ethyl acetate was added, and then the solution was washed with saturated brine. The obtained organic phase was dried and concentrated under reduced pressure. The target compound was prepared by high performance liquid phase to obtain 51 mg of the target compound as a pale yellow solid, with a two-step yield of 20%. (ES, m/z): [M+1]⁺=384. H-NMR: (300 MHz, DMSO-d⁶, ppm): δ10.60 (s, 1H), 8.92 (s, 1H), 8.55 (s, 1H), 8.13 (dd, J=6.9, 2.7 Hz, 1H), 7.81 (m, 1H), 7.44 (t, J=9.0 Hz, 1H), and 1.40 (s, 9H).

Example 45

2-(2-Tert-Butylamino-oxalyl)-4-amide-N-(3-chloro-4-fluoro-phenyl)-5-methyl-thiazole (Compound 45)

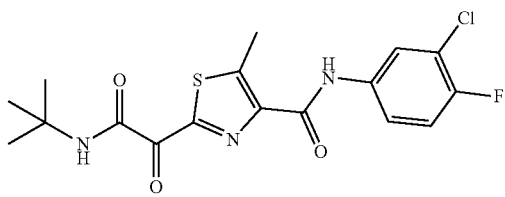 [SMILES: Cc1sc(C(=O)C(=O)NC(C)(C)C)nc1C(=O)Nc1ccc(F)c(Cl)c1]

According to the synthetic route and reaction conditions of Example 44, in step 45a, the raw material was replaced with 2-bromo-5-methylthiazole-4-carboxylic acid (I-14-45) to synthesize Compound 51. The total yield was 4%. (ES, m/z): [M+1]⁺=398.

Example 46

2-(2-Tert-butylamino-oxalyl)-4-amide-N-(3-chloro-4-fluoro-phenyl)-oxazole (Compound 46)

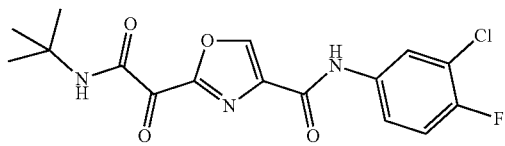 [SMILES: CC(C)(C)NC(=O)C(=O)c1nc(C(=O)Nc2ccc(F)c(Cl)c2)co1]

According to the synthetic route and reaction conditions of Example 44, in step 46a, the raw material was replaced with 2-bromo-oxazole-4-carboxylic acid (I-14-46) to synthesize Compound 46. The total yield was 3%. (ES, m/z): [M+1]⁺=368.

Example 47

2-(2-Tert-Butylamino-oxalyl)-4-amide-N-(3-chloro-4-fluoro-phenyl)-5-methyl-oxazole (Compound 47)

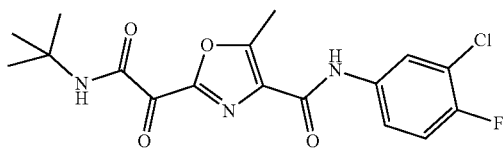 [SMILES: Cc1oc(C(=O)C(=O)NC(C)(C)C)nc1C(=O)Nc1ccc(F)c(Cl)c1]

According to the synthetic route and reaction conditions of Example 44, in step 47a, the raw material was replaced with 2-bromo-5-methyloxazole-4-carboxylic acid (I-14-47) to synthesize Compound 47. The total yield was 5%. (ES, m/z): [M+1]+=382.

Example 48

3-amide-N-(3-chloro-4-fluoro-phenyl)-5-(2-tert-butylamino-oxalyl)-isoxazole (Compound 48)

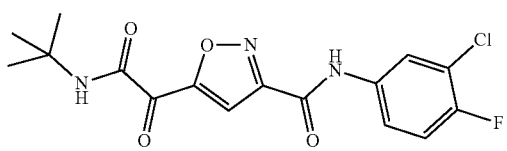 [SMILES: CC(C)(C)NC(=O)C(=O)c1cc(C(=O)Nc2ccc(F)c(Cl)c2)no1]

According to the synthetic route and reaction conditions of Example 44, in step 48a, the raw material was replaced with 2-bromoisoxazole-4-carboxylic acid (I-14-48) to synthesize Compound 48. The total yield was 5%, and the total yield was 4%. (ES, m/z): [M+1]⁺=368.

Example 49 to Example 51 were synthesis according to the specific route shown in Scheme 2 below

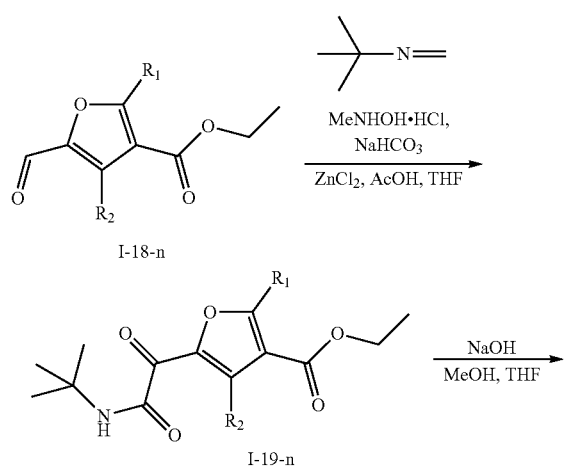

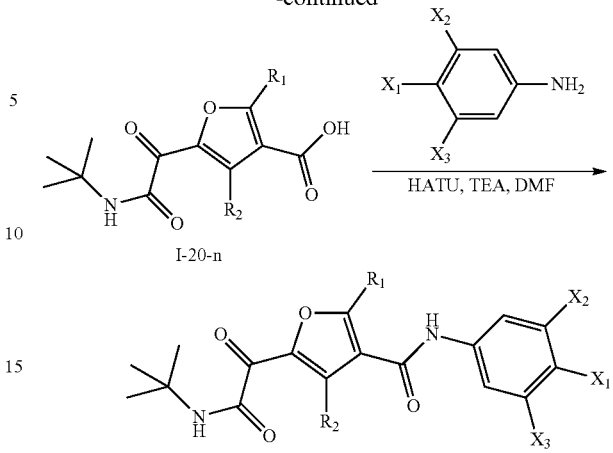

49: $R_1$ = CH₃, $R_2$ = Cl, $X_1$ = F, $X_2$ = F, $X_3$ = F;
50: $R_1$ = H, $R_2$ = Cl, $X_1$ = F, $X_2$ = Cl, $X_3$ = H;
51: $R_1$ = Cl, $R_2$ = H, $X_1$ = F, $X_2$ = Cl, $X_3$ = H

Example 49

2-Methyl-3-amide-N-(3,4,5-trifluorophenyl)-4-chloro-5-(2-tert-butylamino-oxalyl)-furan (Compound 49)

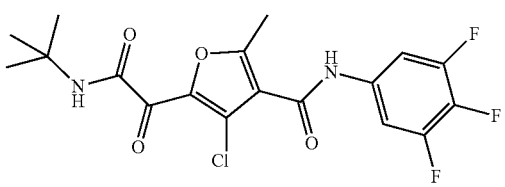 [SMILES: Cc1oc(C(=O)C(=O)NC(C)(C)C)c(Cl)c1C(=O)Nc1cc(F)c(F)c(F)c1]

Step 49a: 2-Methyl-3-ethylcarboxylate-4-chloro-5-(2-tert-butylamino-oxalyl)-furan (I-19-49)

Under the protection of nitrogen, add ZnCl₂ (2.0 g, 3.0 eq.) into the reaction flask, then add 20 mL THF, and add 2-methyl-3-ethylcarboxylate-4-chloro-5-aldehyde-furan (I-18-49, 1.0 g, 1.0 eq.), then MeNHOH.HCl (0.7 g, 1.6 eq.) and NaHCO₃ (0.7 g, 1.6 eq.) were added, the solution was stirred for 30 minutes, and then n-tert-butyl methylimine (0.8 g, 2.0 eq.) and AcOH (0.9 g, 3 eq.) were added, after the addition, the mixture was stirred at room temperature overnight. After the completion of the reaction, the reaction solution was diluted with ethyl acetate at 10 times of the volume, and was filtered through celite, and the filtrate was spin-dried. The product is then purified by normal phase column, and 550 mg of yellow oil was obtained with a yield of 38%. (ES, m/z): [M+1]⁺=316.

Step 49b: 2-Methyl-3-carboxylic acid-4-chloro-5-(2-tert-butylamino-oxalyl)-furan (I-20-49)

I-19-49 (450 mg, 1.0 eq.) was dissolved in 6 mL tetrahydrofuran, 6 mL methanol and 2 mL water, and NaOH (120 mg, 2.0 eq.) was added. After 30 minutes of reaction, TLC monitored the completion of the reaction. After the reaction was completed, add 10 times the volume of water and 10 times the volume of ethyl acetate to the reaction solution to separate the liquids, adjust the pH of the aqueous phase to about 3 with 1N HCl. Extract twice with ethyl acetate of 10 times the volume, combine the organic phases that was dried on sodium sulfate. The organic phase was spin-dried to obtain a crude product. The crude product was used directly in the next step. (ES, m/z): [M+1]$^+$=288.

Step 49c

2-Methyl-3-amide-N-(3,4,5-trifluorophenyl)-4-chloro-5-(2-tert-butylamino-oxalyl)-furan (Compound 49)

The 2-methyl-3-carboxylic acid-4-chloro-5-(2-tert-butylamino-oxalyl)-furan (I-20-49, 3.3 g, 1.0 eq.), 3, 4, 5-tri Fluoroaniline (194 mg, 2.0 eq.), DMF (2 mL), TEA (133 mg, 2.0 eq.) were added to the reaction flask sequentially, the temperature was cooled to 0 degree C., and HATU (377 mg, 1.5 eq.) was added. Naturally warm to room temperature and stir overnight.

After the reaction was completed, it was subjected to reverse-phase purification and then sent to preparation to obtain 70 mg of yellow solid with a yield of 12%. (ES, m/z): [M+1]$^+$=417. H-NMR: (300 MHz, DMSO-d$^6$, ppm): δ10.98 (b, 1H), 8.58(s, 1H), 7.66 (m, 2H), 2.74(s, 3H), 1.35(s, 9H).

Example 50

3-Amide-N-(3-chloro-4-fluoro-phenyl)-4-chloro-5-(2-tert-butylamino-oxalyl)-furan (Compound 50)

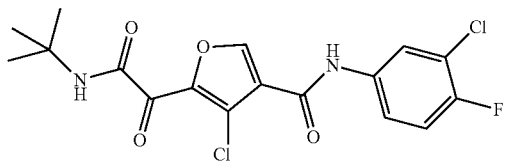 [SMILES: CC(C)(C)NC(=O)C(=O)c1occ(C(=O)Nc2ccc(F)c(Cl)c2)c1Cl]

According to the synthesis route and reaction conditions of Example 49, the raw material was replaced with 3-ethylcarboxylate-4-chloro-5-aldehyde furan (I-18-50) in step 50a, and the raw material was replaced with 3-chloro-4-fluoroaniline in step 50c, thus Compound 50 was synthesized. The total yield was 6%. (ES, m/z): [M+1]$^+$=401. H-NMR: (300 MHz, CDCl$_3$, ppm): δ8.40(s, 1H), 8.31 (s, 1H), 7.81(dd, J=6.9, 3.9 Hz, 1H), 7.48 (m, 1H), 7.21(t, J=8.7 Hz, 1H), 6.82 (s, 1H), 1.48 (s, 9H).

Example 51

2-Chloro-3-amide-N-(3-chloro-4-fluoro-phenyl)-5-(2-tert-butylamino-oxalyl)-furan (Compound 51)

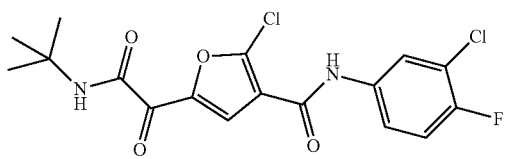 [SMILES: CC(C)(C)NC(=O)C(=O)c1cc(C(=O)Nc2ccc(F)c(Cl)c2)c(Cl)o1]

According to the synthetic route and reaction conditions of Example 49, the raw material was replaced with ethyl 2-chloro-3-ethylcarboxylate-5-aldehyde furan (I-18-51) in step 51a, and the raw material was replaced with 3-chloro-4-fluoroaniline in step 51c, thus Compound 51 was synthesized. The total yield was 5%. (ES, m/z): [M+1]$^+$=401.

Example 52 to Example 78 were synthesis according to the specific route shown in Scheme 3

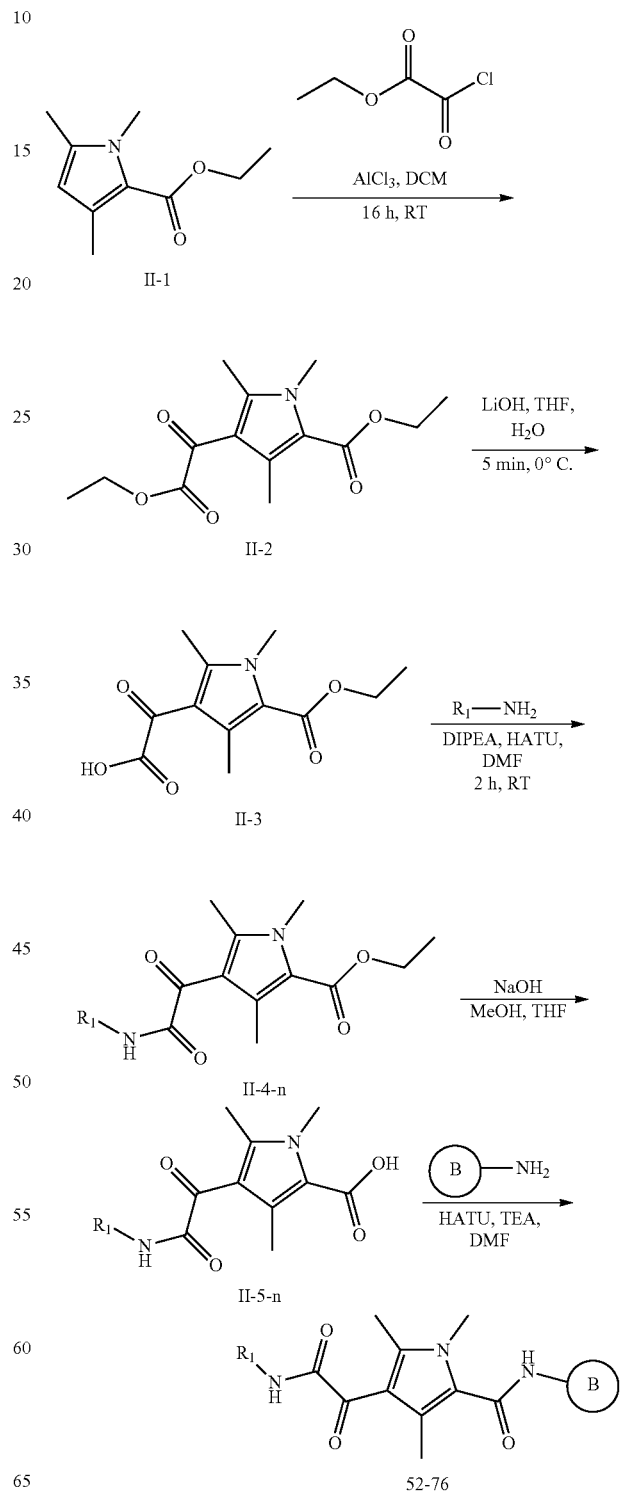

Example 52

1,3,5-Trimethyl-2-amide-N-(benzofuran-5)-4-(2-tert-butylamino-oxalyl)-pyrrole (Compound 52)

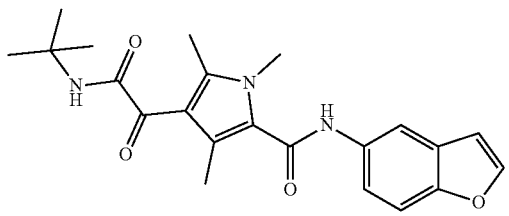 [SMILES: Cc1c(C(=O)C(=O)NC(C)(C)C)c(C)n(C)c1C(=O)Nc1ccc2occc2c1]

Step 52a: 1,3,5-Trimethyl-2-ethylcarboxylate-4-oxalatoethyl-pyrrole (II-2)

Under the protection of nitrogen, $AlCl_3$ (5.3 g, 4.0 eq.) was dissolved in dichloromethane, the reaction solution was reduced to 0° C., ethyl oxalyl chloride (5.5 g, 4.0 eq.) was added while stirring, and the mixture was stirred at 0° C. for 30 min. Then 1,3,5-trimethyl-2-ethylcarboxylate-pyrrole (II-1, 1.8 g, 1.0 eq.) was added to the above reaction solution, and the reaction was allowed to warm up naturally for 16 h. TLC monitored the completion of the reaction. The reaction was quenched by adding dilute hydrochloric acid, and then the solution was washed with water and saturated brine. The organic phase was dried and concentrated under reduced pressure, and separated by a silica gel column to obtain 2.1 g of the target compound with a yield of 74%. (ES, m/z): $[M+1]^+=282$.

Step 52 b: 1,3,5-Trimethyl-2-ethylcarboxylate-4-oxalo-pyrrole (II-3)

II-2 (2.1 g, 1.0 eq.) was dissolved in 60 mL of tetrahydrofuran and 20 mL of water, the reaction solution was cooled to 0° C., and LiOH (357 mg, 2.0 eq.) was added. After 5 minutes of reaction, TLC monitored the completion of the reaction. Concentrate under reduced pressure to remove tetrahydrofuran, adjust pH to 3 with 1M dilute hydrochloric acid under ice bath, extract twice with 10 times of ethyl acetate, combine the organic phases that was dried over anhydrous sodium sulfate, then it was concentrated under reduced pressure, and was directly used in the next step. (ES, m/z): $[M+1]^+=254$.

Step 52c: 1,3,5-Trimethyl-2-ethylcarboxylate-4-(2-tert-butylamino-oxalyl)-pyrrole (II-4-52)

Dissolve intermediate II-3 in 10 mL DMF, add DIPEA (2.9 g, 3.0 eq.), tert-butylamine (810 mg, 1.5 eq.) were added, then add HATU (3.4 g, 1.2 eq.), and the system reacted at room temperature for 6 h. TLC monitored the completion of the reaction. The reaction was quenched by adding water, then ethyl acetate was added, and the solution was washed with saturated brine. The obtained organic phase was dried and concentrated under reduced pressure. The target compound was prepared by high-performance liquid phase to obtain 1.5 g of the target compound as a pale yellow solid. The two-step yield was 66%. (ES, m/z): $[M+1]^+=309$.

Step 52d: 1,3,5-trimethyl-2-carboxylic acid-4-(2-tert-butylamino-oxalyl)-pyrrole (II-5-52)

Dissolve II-4-52 (308 mg, 1.0 eq.) in 6 mL tetrahydrofuran, 6 mL methanol and 2 mL water, and add NaOH (80 mg, 2.0 eq.). After 30 minutes of reaction, TLC monitored the completion of the reaction. After the reaction is completed, add 10 times the volume of water and 10 times the volume of ethyl acetate to the reaction solution to separate the liquids, adjust the pH of the aqueous phase to about 3 with 1N HCl. Extract twice with 10 times the volume of ethyl acetate, combine the organic phases, which was dried on anhydrous sodium sulfate. The organic phase was spin-dried to obtain a crude product. The crude product was used directly in the next step. (ES, m/z): $[M+1]^+=281$.

Step 52e 1,3,5-Trimethyl-2-amide-N-(benzofuran-5-yl)-4-(2-tert-butylamino-oxalyl)-pyrrole (Compound 52)

Add II-5-52, benzofuran-5-amine (266 mg, 2.0 eq.), DMF (2 mL), TEA (202 mg, 2.0 eq.) to the reaction flask in turn, reduce the temperature to 0 degrees C., and then HATU (570 mg, 1.5 eq.) was added. Naturally warm to room temperature and stir overnight. After the reaction was completed, it was subjected to reverse-phase purification and then sent to preparation and yielded 95 mg of pale yellow solid with a yield of 24%. (ES, m/z): $[M+1]^+=396$. H-NMR: (300 MHz, DMSO-$d^6$, ppm): δ10.23(s, 1H), 8.24 (s, 1H), 8.11(s , 1H), 7.98(s, 1H), 7.62 (s, 1H), 7.56 (s, 1H), 6.97 (s, 1H), 3.75(s, 3H), 2.51(s, 3H), 2.43 (s, 3H), 1.41(s, 9H).

Example 53

1,3,5-Trimethyl-2-amide-N-(benzofuran-5-yl)-4-(2-propargylamino-oxalyl)-pyrrole (Compound 53)

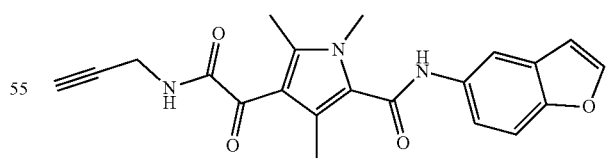

According to the synthesis route and reaction conditions of Example 52, in step 53c, the raw material amine was changed to propynylamine to synthesize Compound 53. The total yield was 11%. (ES, m/z): $[M+1]^+=378$. H-NMR: (300 MHz, DMSO-$d^6$, ppm): δ10.26(s, 1H), 9.14 (t, J=5.7 Hz, 1H), 8.11(s, 1H), 7.98(s, 1H), 7.56 (s, 2H), 6.97 (s, 1H), 4.01(dd, J=5.7, 3.3 Hz, 2H), 3.61(s, 3H) , 3.18(s, 1H), 2.41 (s, 3H), 2.57(s, 3H).

Example 54

1,3,5-Trimethyl-2-amide-N-(benzofuran-5-yl)-4-(2-(1,1-dimethylpropynamido)-oxalyl)-pyrrole (Compound 54)

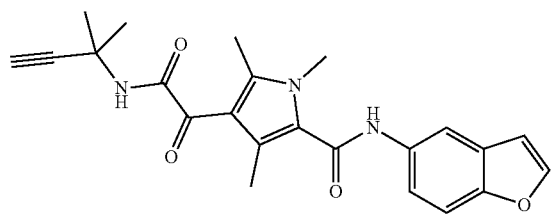 [SMILES: C#CC(C)(C)NC(=O)C(=O)c1c(C)c(C(=O)Nc2ccc3occc3c2)n(C)c1C]

According to the synthesis route and reaction conditions of Example 52, in step 54c, the raw material amine was changed to 1,1-dimethylpropynylamine to synthesize Compound 54. The total yield was 10%. (ES, m/z): [M+1]$^+$=406. H-NMR: (300 MHz, DMSO-d$^6$, ppm): δ10.26(s, 1H), 8.76 (s, 1H), 8.11(s , 1H), 7.99(s, 1H), 7.56 (s, 2H), 6.97 (s, 1H), 3.61(s, 3H), 3.22(s, 1H), 2.44(s, 3H), 2.29(s, 3H), 1.57(s, 6H).

Example 55

1,3,5-Trimethyl-2-amide-N-(benzofuran-5-yl)-4-(2-(1-ethynylcyclopropane-1-amino)-oxalyl)-Pyrrole (Compound 55)

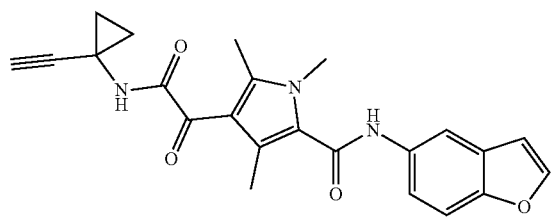 [SMILES: C#CC1(NC(=O)C(=O)c2c(C)c(C(=O)Nc3ccc4occc4c3)n(C)c2C)CC1]

According to the synthesis route and reaction conditions of Example 52, in step 55c, the raw material amine was replaced with 1-ethynylcyclopropaneamine, and Compound 55 was synthesized. The total yield was 11%. (ES, m/z): [M+1]$^+$=404. H-NMR: (300 MHz, DMSO-d$^6$, ppm): δ10.26 (s, 1H), 9.29(s, 1H), 8.11(s , 1H), 7.98(s, 1H), 7.56 (s, 2H), 6.97(s, 1H), 3.61(s, 3H), 2.41 (s, 3H), 2.32(s, 3H), 1.18(t, J=4.2 Hz, 2H), 1.06(t, J=4.2 Hz, 2H).

Example 56

1,3,5-Trimethyl-2-amide-N-(benzofuran-5-yl)-4-(2,4 (S)-1,1,1-trifluoropropane-2-Aminoyoxalyl)-pyrrole (Compound 56)

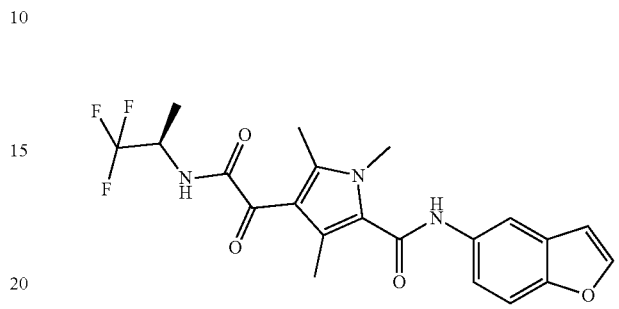

According to the synthetic route and reaction conditions of Example 52, in step 56c, the raw material amine was replaced with (S)-1,1,1-trifluoropropan-2-amine, and Compound 56 was synthesized. The total yield was 10%. (ES, m/z): [M+1]$^+$=436. H-NMR: (300 MHz, DMSO-d$^6$, ppm): δ10.29(s, 1H), 9.36(d, J=9.0 Hz, 1H), 8.11(s, 1H), 7.99(s, 1H), 7.56 (s, 2H), 6.97 (s, 1H), 4.74(m, 1H), 3.74(s, 3H), 2.41(s, 3H) , 2.36 (s, 3H), 1.32(d, J=6.9 Hz, 3H).

Example 57

1,3,5-Trimethyl-2-amide-N-(benzofuran-5-yl)-4-(2-(3-methyl-3-oxetanino)-oxalyl)-pyrrole (Compound 57)

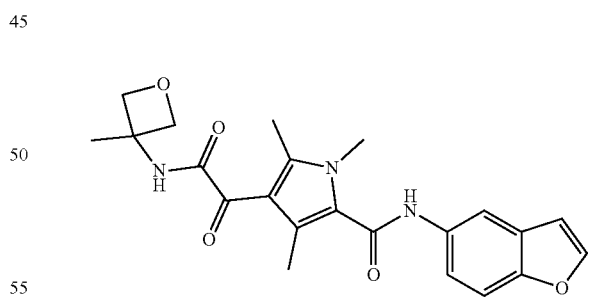

According to the synthesis route and reaction conditions of Example 52, in step 57c, the raw material amine was replaced with 3-methyl-3-oxetanamine to synthesize Compound 57. The total yield was 11%. (ES, m/z): [M+1]$^+$=410. H-NMR: (300 MHz, DMSO-d$^6$, ppm): δ10.26(s, 1H), 9.20 (s, 1H), 8.11(s, 1H), 7.99(d, J=2.1 Hz, 1H), 7.56 (s, 2H), 6.97(d, J =2.1 Hz, 1H), 4.68(d, J=6.3 Hz, 2H), 4.38(d, J=6.3 Hz, 2H), 3.62(s, 3H), 2.42(s, 3H), 2.28 (s, 3H), and 1.60(s, 3H).

Example 58

1,3,5-Trimethyl-2-amide-N-(benzofuran-5-yl)-4-(2-cyclopentylamino-oxalyl)-pyrrole (Compound 58)

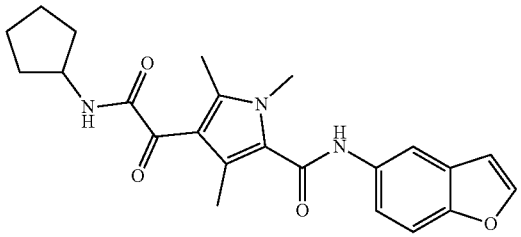 [SMILES: Cc1c(C(=O)C(=O)NC2CCCC2)c(C)n(C)c1C(=O)Nc1ccc2occc2c1]

According to the synthesis route and reaction conditions of Example 52, in step 58c, the raw material amine was replaced with cyclopentylamine, and Compound 58 was synthesized. The total yield was 13%. (ES, m/z): [M+1]$^+$=408. H-NMR: (300 MHz, DMSO-d$^6$, ppm): δ 10.25 (s, 1H), 8.65(d, J=2.1 Hz, 1H), 8.11(s, 1H), 7.98(d, J=2.1 Hz, 1H), 7.56(s, 2H), 6.97(d, J=2.1 Hz, 1H), 4.11(d, J=6.3 Hz, 1H), 3.83(s, 3H), 2.41(s, 3H), 2.26 (s, 3H), 1.86(m, 2H), 1.71(m, 2H), and 1.65(m, 4H).

Example 59

1,3,5-Trimethyl-2-amide-N-(benzofuran-5-yl)-4-(2-(thiazol-2-amino)-oxalyl)-pyrrole (Compound 59)

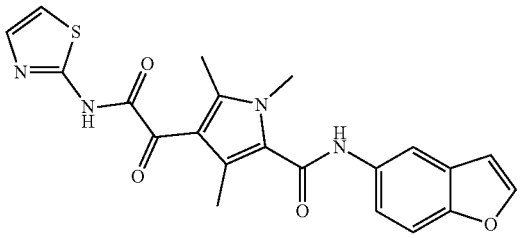 [SMILES: Cc1c(C(=O)C(=O)Nc2nccs2)c(C)n(C)c1C(=O)Nc1ccc2occc2c1]

According to the synthesis route and reaction conditions of Example 52, in step 59c, the raw material amine was replaced with thiazol-2-amine, and Compound 59 was synthesized. The total yield was 7%. (ES, m/z): [M+1]$^+$=423. H-NMR: (300 MHz, DMSO-d$^6$, ppm): δ13.00(b, 1H), 10.36 (s, 1H), 8.11(s, 1H), 7.98(s, 1H), 7.58(m, 3H), 7.38(d, J=3.6 Hz, 1H), 7.01 (s, 1H), 3.74(s, 3H), 2.41 (s, 3H), and 2.22(s, 3H).

Example 60

1,3,5-Trimethyl-2-amide-N-(benzofuran-5-yl)-4-(2-(N-methyl-1-carboxamide-3,3-difluorocyclobutane-1-amine)-oxalyl)-pyrrole (Compound 60)

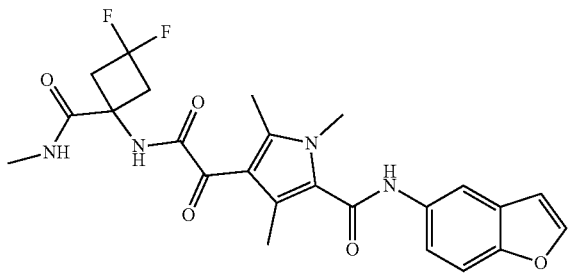 [SMILES: CNC(=O)C1(NC(=O)C(=O)c2c(C)c(C(=O)Nc3ccc4occc4c3)n(C)c2C)CC(F)(F)C1]

According to the synthetic route and reaction conditions of Example 52, in step 60c, the raw material amine was changed to N-methyl-1-carboxamide-3,3-difluorocyclobutane-1-amine to synthesize Compound 60. The total yield was 8%. (ES, m/z): [M+1]$^+$=487. H-NMR: (300 MHz, DMSO-d$^6$, ppm):δ10.25(s, 1H), 9.52(s, 1H), 8.11(s, 1H), 7.99(d, J=2.4 Hz, 1H), 7.72(t, J=4.8 Hz, 1H), 7.59 (s, 2H), 6.97(s, 1H), 3.62(s, 3H), 3.32(m, 2H), 2.98(m, 2H), 2.73(s, 3H), 2.39 (s, 3H), 2.26(s, 3H).

Example 61

1,3,5-Trimethyl-2-amide-N-(benzofuran-5-yl)-4-(2-(1-ethynyl-3,3-difluorocyclobutane)-1-amine)-oxalyl)-pyrrole (Compound 61)

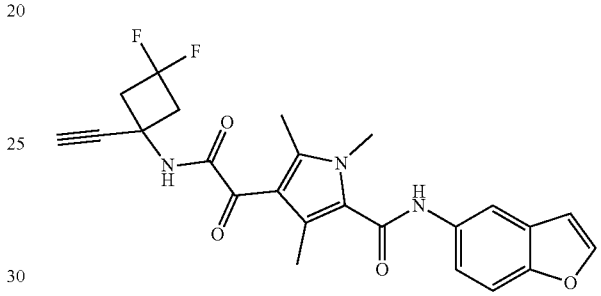

According to the synthetic route and reaction conditions of Example 52, in step 61c, the raw material amine was replaced with 1-ethynyl-3,3-difluorocyclobutane-1-amine to synthesize Compound 61. The total yield was 9%. (ES, m/z): [M+1]+=454.

Example 62

1,3,5-trimethyl-2-amide-N-(benzofuran-5-yl)-4-(2-(3-methoxymethyl-3-oxetan)(amino)-oxalyl)-pyrrole (Compound 62)

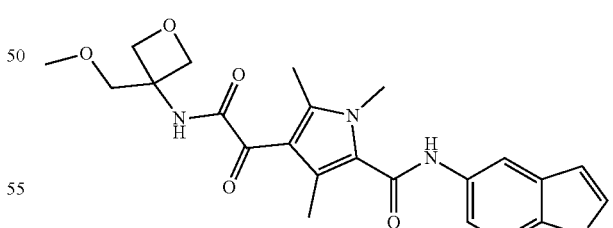

According to the synthetic route and reaction conditions of Example 52, the raw material amine was replaced with 3-methoxymethyl-3-oxetanamine in step 62c, and Compound 62 was synthesized. The total yield was 11%. (ES, m/z): [M+1]$^+$=440. H-NMR: (300 MHz, CDCl$_3$, ppm): δ 8.02(s, 1H), 7.67(s, 1H), 7.52(m, 2H), 7.42(m, 2H), 6.93(s, 1H), 4.96(d, J=6.9 Hz, 2H), 4.63(d, J=6.9 Hz, 2H), 3.98(s, 2H), 3.70(s, 3H), 3.53 (s, 3H), 2.45 (s, 6H).

Example 63

1,3,5-Trimethyl-2-amide-N-(benzothiophen-5-yl)-4-(2-propargylamino-oxalyl)-pyrrole (Compound 63)

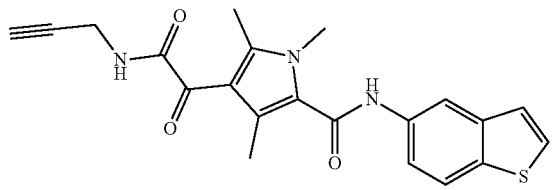 [SMILES: C#CCNC(=O)C(=O)c1c(C)c(C(=O)Nc2ccc3sccc3c2)n(C)c1C]

According to the synthesis route and reaction conditions of Example 52, in step 63c, the raw material amine was replaced with propynylamine; in step 63e, the raw material amine was replaced with 5-benzothiopheneamine, and Compound 63 was synthesized. The total yield was 8%. (ES, m/z): [M+1]$^+$=394. H-NMR: (300 MHz, DMSO-d$^6$, ppm): δ 10.35(s, 1H), 9.16(t, J=5.7 Hz, 1H), 8.38(s, 1H), 7.95(d, J=8.4 Hz, 1H), 7.78(d, J=5.4 Hz, 1H), 7.60(dd, J=8.7, 1.8 Hz, 1H), 7.46(d, J=5.4 Hz, 1H), 4.01(m, 2H), 3.76 (s, 3H), 3.12 (s, 1H), 2.41(s, 3H), 2.26(s, 3H).

Example 64

1,3,5-Trimethyl-2-amide-N-(1-methyl-1 H-indol-5-yl)-4-(2-propargylamino-oxalyl)-pyrrole (Compound 64)

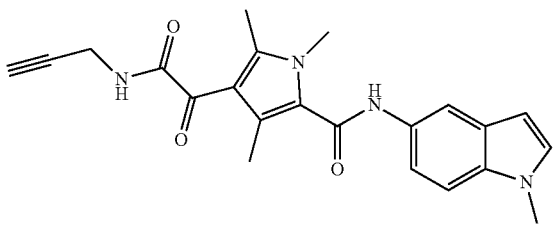 [SMILES: C#CCNC(=O)C(=O)c1c(C)c(C(=O)Nc2ccc3c(ccn3C)c2)n(C)c1C]

According to the synthesis route and reaction conditions of Example 52, in step 64c, the raw material amine was replaced with propynylamine; in step 64e, the raw material amine was replaced with 1-methyl-1H-5-indoleamine, and Compound 64 was synthesized. The total yield was 10%. (ES, m/z): [M+1]$^+$=391. H-NMR: (300 MHz, DMSO-d$^6$, ppm): δ10.07(s, 1H), 9.14(s, 1H), 7.98 (s , 1H), 7.39 (s, 2H), 7.31(s, 1H), 6.40(s, 1H), 4..01(s, 2H), 3.78 (s, 3H), 3.61(s, 3H), 3.18 (s, 1H), 2.40(s, 3H), 2.26(s, 3H).

Example 65

1,3,5-Trimethyl-2-amide-N-(benzofuran-6-yl)-4-(2-propargylamino-oxalyl)-pyrrole (Compound 65)

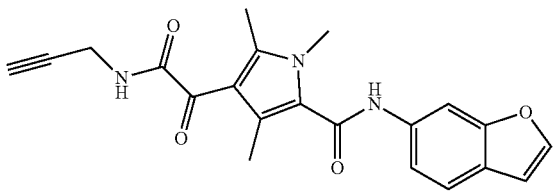 [SMILES: C#CCNC(=O)C(=O)c1c(C)c(C(=O)Nc2ccc3ccoc3c2)n(C)c1C]

According to the synthetic route and reaction conditions of Example 52, in step 65c, the raw material amine was replaced with propynylamine; in step 65c, the raw material amine was replaced with 6-benzofuranamine, and Compound 65 was synthesized. The total yield was 6%. (ES, m/z): [M+1]$^+$=378.

Example 66

1,3,5-Trimethyl-2-amide-N-(naphthalen-2-yl)-4-(2-propargylamino-oxalyl)-pyrrole (Compound 66)

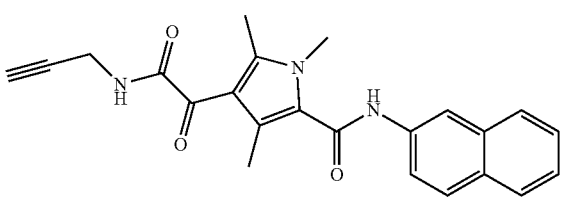 [SMILES: C#CCNC(=O)C(=O)c1c(C)c(C(=O)Nc2ccc3ccccc3c2)n(C)c1C]

According to the synthesis route and reaction conditions of Example 52, in step 66c, the raw material amine was replaced with propynylamine; in step 66e, the raw material amine was replaced with 2-naphthylamine, and Compound 66 was synthesized. The total yield was 13%. (ES, m/z): [M+1]$^+$=388. H-NMR: (300 MHz, DMSO-d$^6$, ppm): δ10.45 (s, 1H), 9.17(t, J =5.7 Hz, 1H), 8.42(s, 1H), 7.87(m, 3H), 7.37(dd, J=8.7, 1.8 Hz, 1H), 7.46 (m, 2H), 4.01(dd, J=5.7, 2.4 Hz, 2H) , 3.87(s, 3H), 3.20(s, 1H), 2.42(s, 3H), 2.28(s, 3H).

Example 67

1,3,5-Trimethyl-2-amide-N-(quinoxalin-6-yl)-4-(2-propargylamino-oxalyl)-pyrrole (Compound 67)

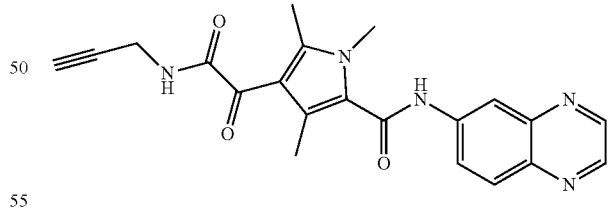

According to the synthesis route and reaction conditions of Example 52, in step 67c, the raw material amine was replaced with propynylamine; in step 67e, the raw material amine was replaced with 6-quinoxalinamine, and Compound 67 was synthesized. The total yield was 4%. (ES, m/z): [M+1]$^+$=390. H-NMR: (300 MHz, DMSO-d$^6$, ppm): δ 10.74(s, 1H), 9.18(t, J=5.7 Hz, 1H) , 8.91(d, J=2.1 Hz, 1H), 8.50(d, J=2.1 Hz, 1H), 8.60(s, 1H), 8.09(s, 2H), 4.01(dd, J=5.4, 3.0 Hz, 2H), 3.65(s, 3H), 3.19 (t, J=2.4 Hz, 1H), 2.43(s, 3H), 2.29(s, 3H).

Example 68

1,3,5-Trimethyl-2-amide-N-(quinolin-6-yl)-4-(2-propargylamino-oxalyl)-pyrrole (Compound 68)

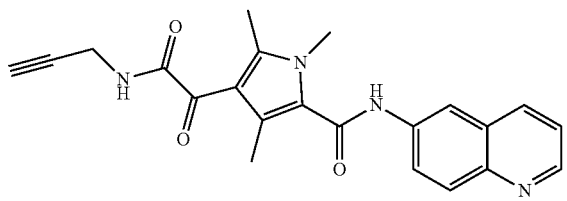 [SMILES: C#CCNC(=O)C(=O)c1c(C)c(C(=O)Nc2ccc3ncccc3c2)n(C)c1C]

According to the synthesis route and reaction conditions of Example 52, in step 68c, the raw material amine was replaced with propynylamine; in step 68e, the raw material amine was replaced with 6-quinolinamine to synthesize Compound 68. The total yield is 3%. (ES, m/z): [M+1]$^+$=389. H-NMR: (300 MHz, DMSO-d$^6$, ppm): δ 10.68 (s, 1H), 9.16(m, 1H), 8.94(d, J=3.0 Hz, 1H), 8.61(s, 1H), 8.07(m, 2H), 7.69(m, 1H), 4.01(m, 2H), 3.70(s, 3H), 3.19 (s, 1H), 2.43(s, 3H), 2.35(s, 3H).

Example 69

1,3,5-Trimethyl-2-amide-N-(2,3-dihydrobenzofuran-5-yl)-4-(2-propargylamino-oxalyl)-pyrrole (Compound 69)

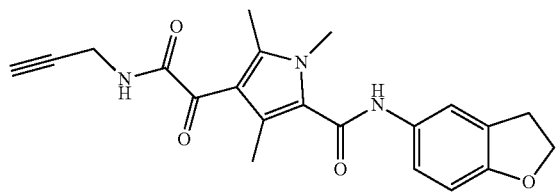 [SMILES: C#CCNC(=O)C(=O)c1c(C)c(C(=O)Nc2ccc3c(c2)CCO3)n(C)c1C]

According to the synthetic route and reaction conditions of Example 52, in step 69c, the raw material amine was replaced with propynylamine; in step 69e, the raw material amine was replaced with 2,3-dihydrobenzofuran-5-amine to synthesize Compound 69. The total yield was 8%. (ES, m/z): [M+1]$^+$=380. H-NMR: (300 MHz, DMSO-d$^6$, ppm): δ 10.06 (s, 1H), 9.14(t, J =5.7 Hz, 1H) , 7.62(s, 1H), 7.36(d, J =8.7 Hz, 1H), 6.72(d, J =8.7 Hz, 1H), 4.51(t, J=8.7 Hz, 2H), 4.00 (dd, J=5.4, 2.4 Hz, 2H), 3.58(s, 3H), 3.19(m, 3H), 2.42(s, 3H), 2.27(s, 3H).

Example 70

1,3,5-Trimethyl-2-amide-N-(benzothiazol-5-yl)-4-(2-propargylamino-oxalyl)-pyrrole (Compound 70)

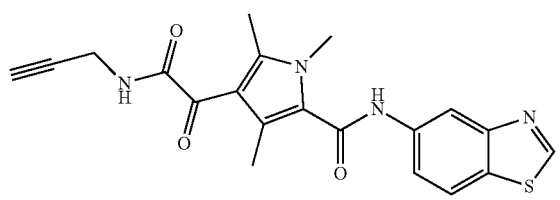 [SMILES: C#CCNC(=O)C(=O)c1c(C)c(C(=O)Nc2ccc3ocnc3c2)n(C)c1C]

According to the synthesis route and reaction conditions of Example 52, in step 70c, the raw material amine was replaced with propynylamine; in step 70e, the raw material amine was replaced with 5-benzothiazolamine, and Compound 70 was synthesized. The total yield was 2%. (ES, m/z): [M+1]$^+$=395. H-NMR: (300 MHz, DMSO-d$^6$, ppm): δ 10.48(s, 1H), 9.40(s, 1H), 9.17(t, J=5.4 Hz, 1H), 8.57(s, 1H), 8.12(d, J=8.7 Hz, 1H), 7.76(dd, J=8.7, 1.5 Hz, 1H), 4.01(dd, J=5.4, 2.4 Hz, 2H), 3.70(s, 3H), 3.20(s, 1H), 2.42(s, 3H), 2.27(s, 3H).

Example 71

1,3,5-Trimethyl-2-amide-N-(benzoxazol-5-yl)-4-(2-propargylamino-oxalyl)-pyrrole (Compound 71)

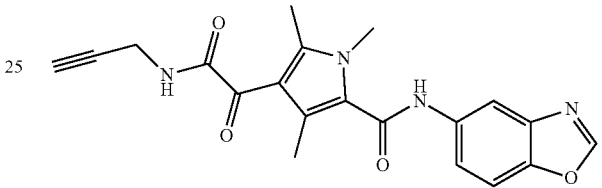

According to the synthetic route and reaction conditions of Example 52, in step 71c, the raw material amine was replaced with propargylamine; in step 71e, the raw material amine was replaced with 5-benzoxazolamine, and Compound 71 was synthesized. The total yield was 2%. (ES, m/z): [M+1]$^+$=379.

Example 72

1,3,5-Trimethyl-2-amide-N-(1-methyl-1H-benzimidazol-5-yl)-4-(2-propargylamino-oxalyl)-Pyrrole (Compound 72)

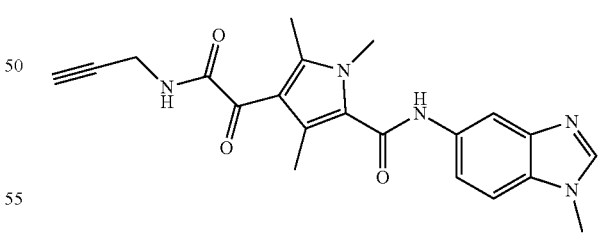

According to the synthesis route and reaction conditions of Example 52, in step 72c, the raw material amine was replaced with propargylamine; in step 72e, the raw material amine was replaced with 1-methyl-1H-benzimidazole-5-amine to synthesize Compound 72. The total yield was 3%. (ES, m/z): [M+1]$^+$=392. H-NMR: (300 MHz, DMSO-d$^6$, ppm): δ10.26(s, 1H), 9.14(m, 1H), 8.23(s, 1H), 8.03(s, 1H), 7.61 (s, 2H), 4.04 (m, 5H), 3.62(s, 3H), 3.19(s, 1H), 2.41 (s, 3H), 2.26(s, 3H).

Example 73

1,3,5-trimethyl-2-amide-N-(1-methyl-1 H-indazol-5-yl)-4-(2-propargylamino-oxalyl)-pyrrole (Compound 73)

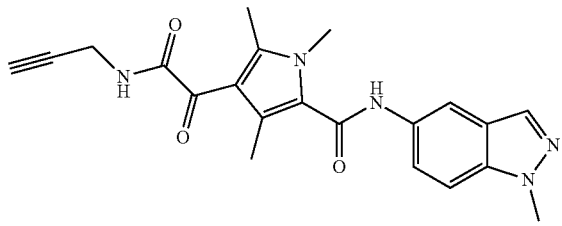 [SMILES: C#CCNC(=O)C(=O)c1c(C)c(C(=O)Nc2ccc3c(cnn3C)c2)n(C)c1C]

According to the synthesis route and reaction conditions of Example 52, in step 73c, the raw material amine was replaced with propargylamine; in step 73e, the raw material amine was replaced with 1-methyl-1H-indazol-5-amine to synthesize Compound 73. The total yield was 2%. (ES, m/z): [M+1]$^+$=392. H-NMR: (300 MHz, DMSO-d$^6$, ppm): δ 10.21 (s, 1H), 9.16(t, J =5.7 Hz, 1H) , 8.16(s, 1H), 8.09(s, 1H), 7.53(t, J =8.7 Hz, 2H), 4.01(dd, J =5.7, 3.0 Hz, 2H), 3.83(s, 3H), 3.62(s, 3H), 3.19(s, 1H), 2.41(s, 3H), 2.26(s, 3H).

Example 74

1,3,5-Trimethyl-2-amide-N-(benzisoxazol-5-yl)-4-(2-propargylamino-oxalyl)-pyrrole (Compound 74)

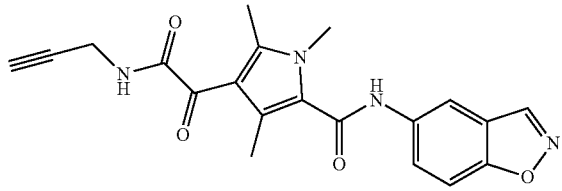 [SMILES: C#CCNC(=O)C(=O)c1c(C)c(C(=O)Nc2ccc3oncc3c2)n(C)c1C]

According to the synthetic route and reaction conditions of Example 52, in step 74c, the raw material amine was replaced with propargylamine; in step 74e, the raw material amine was replaced with 5-benzisoxazolamine, and Compound 74 was synthesized. The yield was 5%. (ES, m/z): [M+1]+=379. H-NMR: (300 MHz, DMSO-d6, ppm): δ 9.24(t, J=5.4 Hz, 1H), 7.17(d, J=9.3 Hz, 1H), 6.93(s, 1H), 6.91(s, 1H), 5.62(d, J =4.8 Hz, 2H), 4.01(d, J =3.3 Hz, 2H), 3.80(s, 3H) , 3.20(s, 1H), 2.42(s, 3H), 2.36(s, 3H).

Example 75

1,3,5-Trimethyl-2-amide-N-(4-fluorobenzofuran-5-yl)-4-(2-propargylamino-oxalyl)-pyrrole (Compound 75)

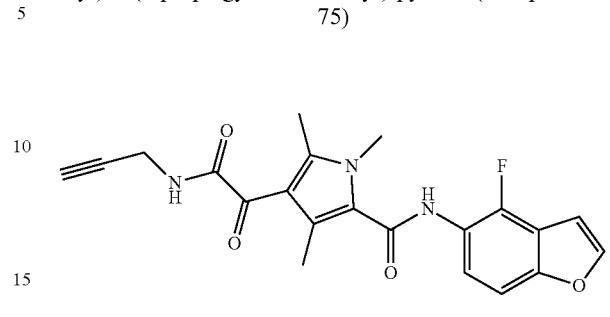

According to the synthetic route and reaction conditions of Example 52, in step 75c, the raw material amine was replaced with propynylamine; in step 75e, the raw material amine was replaced with 4-fluorobenzofuran-5-amine to synthesize Compound 75. The total yield was 9%. (ES, m/z): [M+1]$^+$=396.

Example 76

1,3,5-Trimethyl-2-amide-N-(4-chlorobenzofuran-5-yl)-4-(2-propargylamino-oxalyl)-pyrrole (Compound 76)

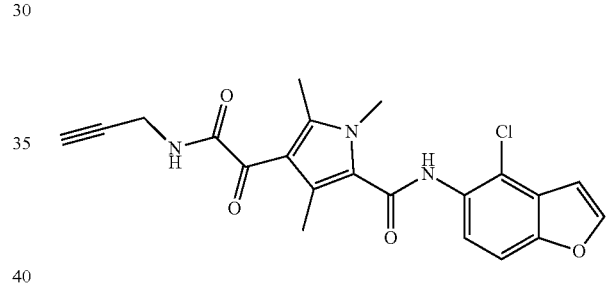

According to the synthesis route and reaction conditions of Example 52, in step 76c, the raw material amine was replaced with propynylamine; in step 76e, the raw material amine was replaced with 4-chlorobenzofuran-5-amine, and Compound 76 was synthesized. The total yield was 11%. (ES, m/z): [M+1]$^+$=412.

Example 77

1,3,5-trimethyl-2-amide-N-(benzofuran-5-yl)-4-(2-(3,3-difluoro-1-(1H-1,2,3-Triazol-4-yl)cyclobutane-1-amino)-oxalyl)-pyrrole (Compound 77)

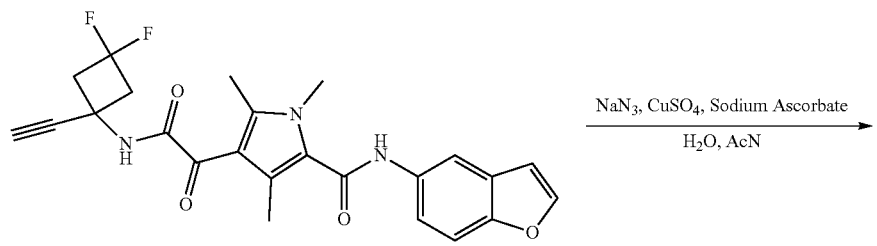

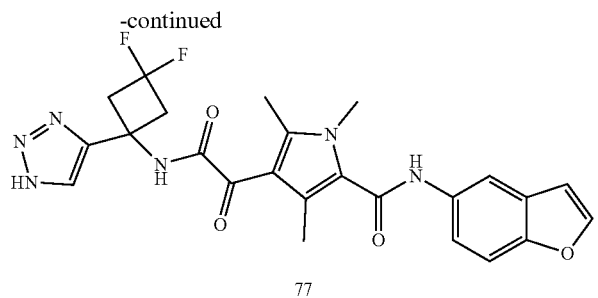

77

Dissolve NaN₃ (192 mg, 6.6 eq.) in 1 mL of water, place it in a microwave tube, add Compound 61 (203 mg, 1.0 eq.), acetonitrile 1 mL, and then add CuSO₄ (86 mg, 1.2 eq.) and sodium ascorbate (44 mg, 0.5 eq.) to the above reaction solution; microwave the system at 80¤ for 1 h, then the reaction solution was injected into saturated NH₄Cl, and the organic phase obtained by EA extraction of three times was dried and concentrated under reduced pressure. After separation by high performance liquid chromatography, 40 mg of the target compound (as white solid) was obtained, and the yield was 18%. (ES, m/z): [M+1]⁺=497, H-NMR: (300 MHz, DMSO-d⁶, ppm): δ14.90(b, 1H), 10.26(s, 1H), 9.73(s , 1H), 8.10(s, 1H), 7.98(s, 1H), 7.81(s, 1H), 7.56(s, 3H), 6.97(s, 1H), 3.60(s, 3H), 3.25(m, 4H), 3.23 (s, 3H), 2.08(s, 3H).

Example 78

1,3,5-trimethyl-2-amide-N-(benzofuran-5-yl)-4-(2-(2-(1H-1,2,3-triazole-4-yl)-2-propylamino)-oxalyl)-pyrrole (Compound 78)

According to the synthetic route and reaction conditions of Example 77, the starting material was replaced with Compound 54 to synthesize Compound 78. The yield was 22%. (ES, m/z): [M+1]⁺=449, H-NMR: (300 MHz, CDCl₃, ppm): δ 8.01(s, 1H), 7.98(b, 1H), 7.65(s, 1H) , 7.62(d, J=2.1 Hz, 1H), 7.47(s, 1H),7.44(s, 1H), 7.37(d, J=8.4 Hz, 2H), 3.66(s, 3H), 2.34(s, 3H), 2.27(s, 3H), 1.85(s, 6H).

Example 79 to Example 82 were synthesis according to the specific route shown in Scheme 4

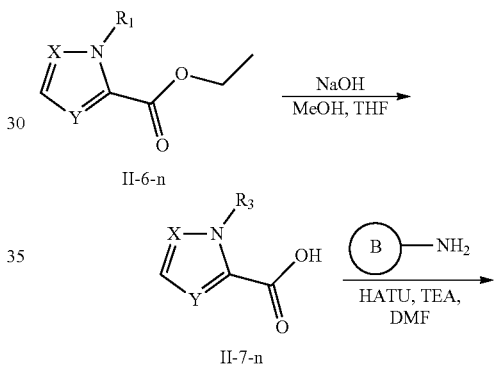

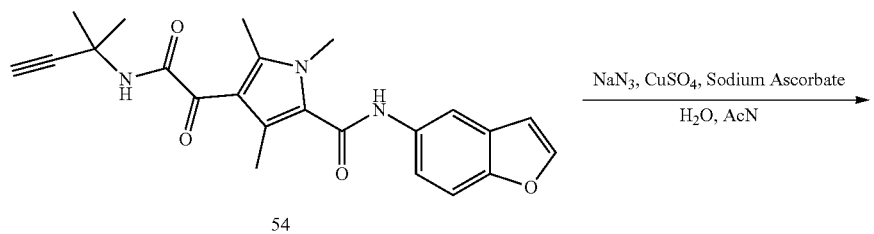

54

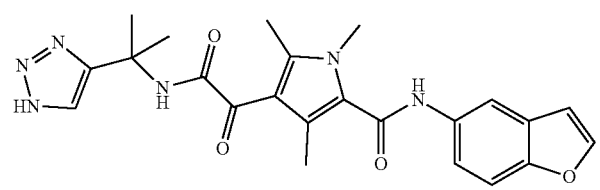

78

-continued

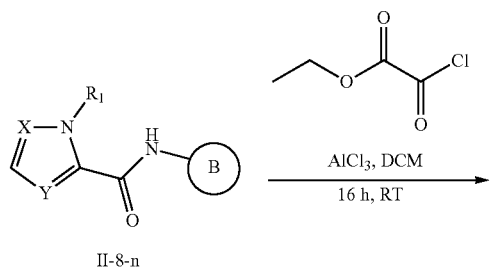

II-8-n

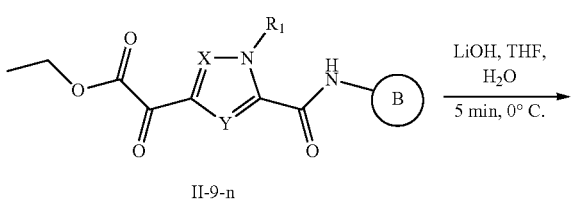

II-9-n

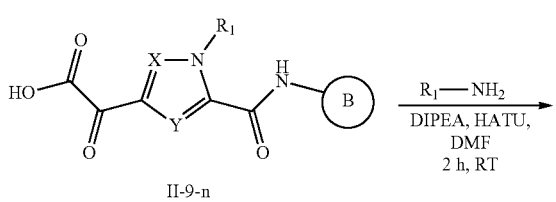

II-9-n

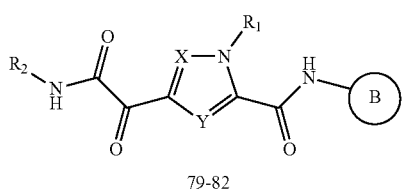

79-82

Example 79

1-Cyclopropyl-2-amide-N-(benzofuran-5-yl)-3,5-dimethyl-4-(2-(1,1-dimethylpropynamine)-oxalyl) pyrrole (Compound 79)

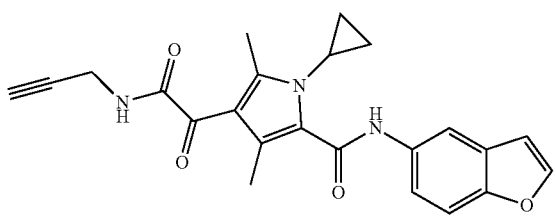 [SMILES: C#CCNC(=O)C(=O)c1c(C)c(C(=O)Nc2ccc3occc3c2)n(C2CC2)c1C]

Step 79a:
1-Cyclopropyl-3,5-dimethyl-pyrrole-2-carboxylic acid (II-7-79)

Dissolve 1-cyclopropyl-2-ethylcarboxylate-3,5-dimethyl-pyrrole (II-6-79, 537 mg, 1.0 eq.) in 6 mL tetrahydrofuran, 6 mL methanol and 2 mL water, add NaOH (240 mg, 2.0 eq.). After 30 minutes of reaction, TLC monitored the completion of the reaction. After the reaction is completed, add 10 times volume of water and 10 times volume of ethyl acetate to the reaction solution to separate the liquids, adjust the pH of the aqueous phase to about 3 with 1N HCl. Extract twice with 10 times volume of ethyl acetate, combine the organic phases that was dried with anhydrous sodium sulfate. The organic phase was spin-dried to obtain a crude product. The crude product was used directly in the next step. (ES, m/z): $[M+1]^+=180$.

Step 79b: 1-Cyclopropyl-2-amide-N-(benzofuran-5-yl)-3,5-dimethyl-pyrrole (II-8-79)

Add II-7-79, benzofuran-5-amine (798 mg, 2.0 eq.), DMF (20 mL), TEA (606 mg, 2.0 eq.) into the reaction flask in turn, reduce the temperature to 0 degrees C., and then HATU (1.7 g, 1.5 eq.) was added. Naturally warm to room temperature and stir overnight. After the completion of the reaction, post-processing, reverse-phase purification and preparation, 300 mg of light yellow solid was obtained with a yield of 34%. (ES, m/z): $[M+1]^+=295$.

Step 79c: 1-Cyclopropyl-2-amide-N-(benzofuran-5-yl)-3,5-dimethyl-4-oxalatoethyl-pyrrole (II-9-79)

Under the protection of nitrogen, AlCl$_3$ (532 mg, 4.0 eq.) was dissolved in dichloromethane, the reaction solution was cooled to 0¤, ethyl oxalyl chloride (548 g, 4.0 eq.) was added with stirring, and the mixture was stirred at 0¤ for 30 min. Then 1,3,5-trimethyl-2-ethylcarboxylate-pyrrole (II-8-79, 295 mg, 1.0 eq.) was added to the above reaction solution, and the reaction was allowed to warm up naturally for 16 h. TLC monitored the completion of the reaction. The reaction was quenched by adding dilute hydrochloric acid, and then the system was washed with water and saturated brine. The organic phase was dried and concentrated under reduced pressure, and separated by a silica gel column to obtain 213 mg of the target compound with a yield of 54%. (ES, m/z): $[M+1]^+=395$.

Step 79d: 1-Cyclopropyl-2-amide-N-(benzofuran-5-yl)-3,5-dimethyl-4-oxalo-pyrrole (II-10-79)

II-9-79 (213 mg, 1.0 eq.) was dissolved in 6 mL tetrahydrofuran and 2 mL water, the reaction solution was cooled to 0° C., and LiOH (26 mg, 2.0 eq.) was added. After 5 minutes of reaction, TLC monitored the completion of the reaction. The solution was concentrated under reduced pressure to remove tetrahydrofuran, then the pH was adjusted to 3 with 1M dilute hydrochloric acid under ice bath, the solution was extracted twice with 10 times ethyl acetate; and the organic phases were combined, dried over anhydrous sodium sulfate, and then concentrated under reduced pressure, and then was directly used in the next step. (ES, m/z): $[M+1]^+=367$.

Step 79e

1-Cyclopropyl-2-amide-N-(benzofuran-5-yl)-3,5-dimethyl-4-(2-(1,1-dimethylpropynamido)-Oxalyl) pyrrole (Compound 79)

Intermediate II-10-79 was dissolved in 5 mL DMF, DIPEA (209 mg, 3.0 eq.) and 1,1-dimethylpropynamine (67 mg, 1.5 eq.) were added successively, and HATU (246 mg ,1.2 eq.) was added and reacted at room temperature for 2 h. TLC monitored the completion of the reaction. The reaction was quenched by adding water, then ethyl acetate was added, and then the solution washed with saturated brine. The obtained organic phase was dried, concentrated under reduced pressure, and separated by a silica gel column to obtain 48 mg of the target compound as a white solid. The two-step yield was 21%. (ES, m/z): [M+1]$^+$=432.

Example 80

1-Difluoromethyl-2-amide-N-(benzofuran-5-yl)-3,5-dimethyl-4-(2-(1,1-dimethylpropyne)Amino)-oxalyl) pyrrole (Compound 80)

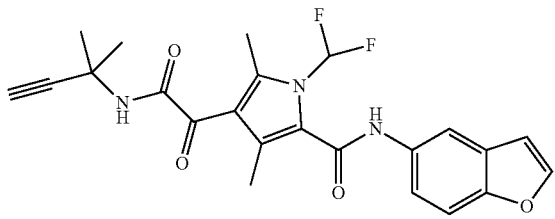 [SMILES: C#CC(C)(C)NC(=O)C(=O)c1c(C)c(C(=O)Nc2ccc3occc3c2)n(C(F)F)c1C]

According to the synthetic route and reaction conditions of Example 79, in step 80a, the starting material was replaced with 1-difluoromethyl-3,5-dimethyl-pyrrole-2-carboxylic acid (II-7-80) to synthesize the Compound 80. The total yield was 5%. (ES, m/z): [M+1]$^+$=442.

Example 81

1-Methylsulfo-2-amide-N-(3.4-difluorophenyl)-3,5-dimethyl-4-(2-(1,1-dimethylpropynamine)-oxalyl) pyrrole (Compound 81)

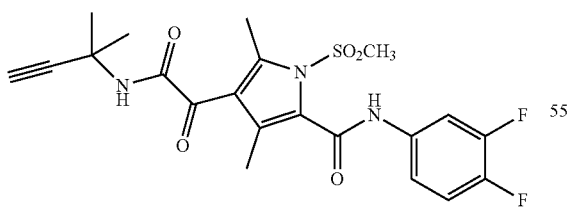

According to the synthetic route and reaction conditions of Example 79, in step 81a, the starting material was replaced with 1-methylsulfo-3,5-dimethyl-pyrrole-2 -carboxylic acid (II-7-81); and in step 81e, the raw material amine was replaced with 3.4-difluoroaniline, and Compound 81 was synthesized. The total yield was 1%. (ES, m/z): [M+1]$^+$=466.

Example 82

1-(2,2,2-trifluoroethyl)-2-amide-N-(3.4-difluorophenyl)-3,5-dimethyl-4-(2-(1,1-Dimethylpropynylamino)-oxalyl)-pyrrole (Compound 82)

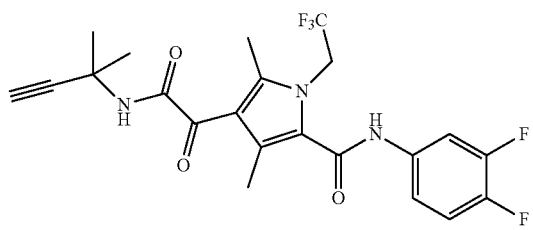 [SMILES: C#CC(C)(C)NC(=O)C(=O)c1c(C)c(C(=O)Nc2ccc(F)c(F)c2)n(CC(F)(F)F)c1C]

According to the synthetic route and reaction conditions of Example 79, in step 82a, the starting material was replaced with 1-(2,2,2-trifluoroethyl)-3,5-dimethyl-pyrrole-2-carboxylic acid (II -7-82); and in step 81e, the raw material amine was changed to 3, 4-difluoroaniline to synthesize compound 82. The total yield was 2%. (ES, m/z): [M+1]$^+$=470.

Example 83

2-Amide-N-(3-chloro-4-fluoro-phenyl)-3-methyl-4-(2-tert-butylamino-oxalyl)-furan (Compound 83)

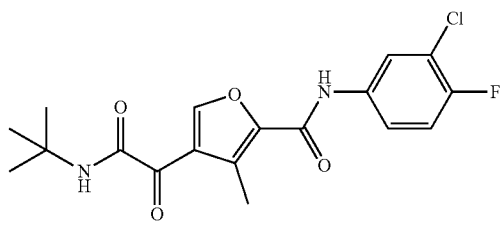 [SMILES: Cc1c(C(=O)C(=O)NC(C)(C)C)coc1C(=O)Nc1ccc(F)c(Cl)c1]

According to Scheme 3, in accordance with the synthetic route and reaction conditions of Example 52, the starting material was replaced with 3-methyl-2-ethyl carboxylate-furan in step 83a; and the raw material amine was replaced with 3-chloro-4-fluoro-aniline in step 83e, thus the compound 83 was synthesized. The total yield was 8%. (ES, m/z): [M+1]$^+$=381. H-NMR: (300 MHz, DMSO-d$^6$, ppm): δ 10.67(s, 1H), 8.91(s, 1H), 8.12(dd, J=6.9, 2.4 Hz, 1H), 8.01(s, 1H), 7.76(s, 1H), 7.55(t, J=4.8 Hz, 1H), 2.56(s, 3H), 1.37(s, 9H).

Example 84

2-amide-N-(3-chloro-4-fluoro-phenyl)-3,5-dimethyl-4-(2-tert-butylamino-oxalyl)-furan (Compound 84)

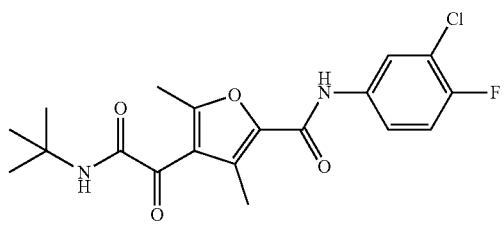 [SMILES: Cc1oc(C(=O)Nc2ccc(F)c(Cl)c2)c(C)c1C(=O)C(=O)NC(C)(C)C]

According to Scheme 3, in accordance with the synthesis route and reaction conditions of Example 52, the starting material is replaced with 3,5-dimethyl-2-ethylcarboxylate-furan in step 84a; the raw material amine is replaced with 3-chloro-4-fluoro-aniline in step 84e, thus the Compound 84 was synthesized. The total yield was 12%. (ES, m/z): [M+1]$^+$=395.

Example 85

2-Amide-N-(3-chloro-4-fluoro-phenyl)-3-methyl-4-(2-tert-butylamino-oxalyl)-thiophene (Compound 85)

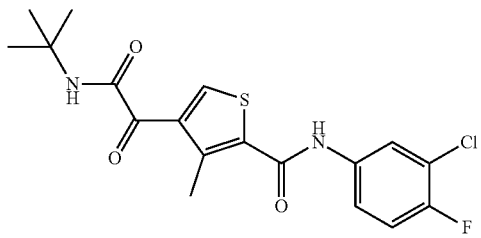 [SMILES: Cc1c(C(=O)C(=O)NC(C)(C)C)csc1C(=O)Nc1ccc(F)c(Cl)c1]

According to Scheme 3, according to the synthetic route and reaction conditions of Example 52, the starting material was replaced with 3-methyl-2-ethyl carboxylate-thiophene in step 85a; and the raw material amine was replaced with 3-chloro-4-fluoro-aniline in step 85e, thus the Compound 85 was synthesized. The total yield was 7%. (ES, m/z): [M+1]$^+$=397. H-NMR: (300 MHz, DMSO-d$^6$, ppm): δ 10.55 (s, 1H), 8.37(s, 1H), 8.01(dd, J=6.9, 2.4 Hz, 1H), 7.92(s, 1H), 7.66(s, 1H), 7.45(t, J=4.8 Hz, 1H), 2.46(s, 3H), 1.38(s, 9H).

Example 86

2-Amide-N-(3-chloro-4-fluoro-phenyl)-3,5-dimethyl-4-(2-tert-butylamino-oxalyl)-thiophene (Compound 86)

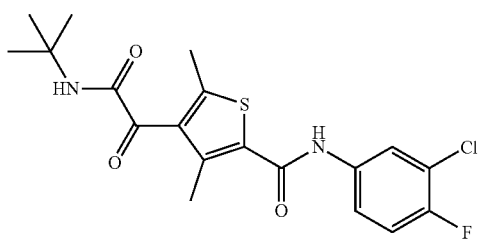 [SMILES: Cc1sc(C(=O)Nc2ccc(F)c(Cl)c2)c(C)c1C(=O)C(=O)NC(C)(C)C]

According to Scheme 3, in accordance with the synthesis route and reaction conditions of Example 52, the starting material was replaced with 3,5-dimethyl-2-ethylcarboxylate-thiophene in step 86a; and the raw material amine was replaced with 3-chloro-4-fluoro-aniline in step 86e, thus the Compound 84 was synthesized. The total yield was 5%. (ES, m/z): [M+1]$^+$=411.

Example 87

1,3-Dimethyl-2-amide-N-(benzofuran-5-yl)-4-(2-(3-methoxymethyl-3-oxetanino))-Oxalyl)-pyrrole (Compound 90)

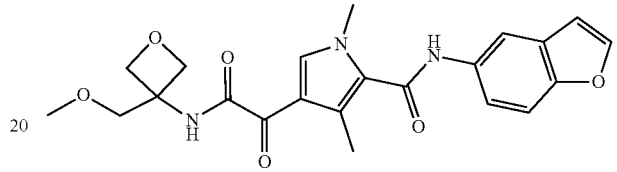

According to Scheme 3, in accordance with the synthesis route and reaction conditions of Example 52, the starting material was replaced with 1,3-dimethyl-2-ethylcarboxylate-pyrrole in step 87a; the raw material amine was replaced with 3-methyl-3-oxetanamin in step 87e, thus the Compound 90 was synthesized. The total yield was 8%. (ES, m/z): [M+1]$^+$=426. H-NMR: (300 MHz, DMSO-d$^6$, ppm): δ 10.25(s, 1H), 9.24(s, 1H), 8.11(s, 1H), 8.07(s, 1H), 7.99(d, J=2.1 Hz, 1H), 7.56(m, 2H), 6.98(d, J=1.8 Hz, 1H), 4.68(d, J=6.9 Hz, 2H), 4.51(d, J=6.9 Hz, 2H), 3.78(s, 3H), 3.70(s, 2H), 3.32(s, 3H), 2.42(s, 3H).

Example 88

1-Methyl-2-amide-N-(benzofuran-5-yl)-4-(2-(3-methoxymethyl-3-oxetanino)-oxalyl)-pyrrole (Compound 91)

According to Scheme 3, in accordance with the synthetic route and reaction conditions of Example 52, the starting material is replaced with ethyl 1-methyl-2-ethylcarboxylate-pyrrole in step 88a; the raw material amine is replaced with 3-methyl-3-oxetanamine in step 88e, thus the Compound 91 was synthesized. The total yield was 10%. (ES, m/z): [M+1]+=412. H-NMR: (300 MHz, DMSO-d$^6$, ppm): δ 10.16(s, 1H), 9.32(s, 1H), 8.16(s, 1H), 8.11(s, 1H), 7.98(d, J=2.1 Hz, 1H), 7.61(s, 1H), 7.57(m, 2H), 6.96(s, 1H), 4.69(d, J=6.6 Hz, 2H), 4.51(d, J=6.6 Hz, 2H), 3.99(d, J=8.4 Hz, 3H), 3.70(s, 2H), 3.38(s, 3H).

Example 89

1,5-Dimethyl-2-amide-N-(benzofuran-5-yl)-4-(2-(3-methoxymethyl-3-oxetanyl))-oxalyl)-pyrrole (Compound 92)

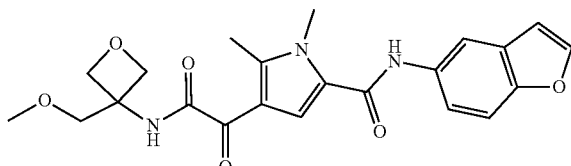

According to Scheme 3, in accordance with the synthesis route and reaction conditions of Example 52, the starting material is replaced with 1,5-dimethyl-2-ethylcarboxylate-pyrrole in step 89a; the raw material amine is replaced with 3-methyl-3-oxetanamine in step 89e, thus the Compound 92 was synthesized. The total yield was 10%. (ES, m/z): $[M+1]^+=426$. H-NMR: (300 MHz, CDCl$_3$, ppm): δ 8.16(s, 1H), 8.11(s, 1H), 7.97(s, 1H), 7.85(s, 1H), 7.57(s, 1H), 7.48(d, J=6.0 Hz, 1H), 7.35(d, J=2.1 Hz, 1H), 6.79(m, 1H), 5.99(d, J=6.9 Hz, 2H), 4.63(d, J=6.9 Hz, 2H), 3.97(s, 3H), 3.88(s, 2H), 3.46(s, 3H), 2.67(s, 3H).

Effect Example-Biological Activity Test

According to in vivo and in vitro biological experiments, the compounds of the present invention especially the preferred compounds not only have strong activity against HBV virus, but are also generally of very low toxicity, as well as good pharmacokinetic characteristics in vivo. They obviously feature the advantages of druggability. According to the structure-activity analysis of all structural molecules in this patent, it can be clearly concluded that molecules in the general formula are a type of molecular structures with high activity, low toxicity, and strong druggability.

I. Anti-hepatitis B Virus Activity and HepG2.2.15 Cell Activity Experiment

1. Experimental Method

In this experiment, real-time fluorescent quantitative PCR (qPCR) method was used to detect the content of HBV DNA in the supernatant of HepG2.2.15 cells to determine the anti-hepatitis B virus activity of the compound in HepG2.2.15 cells, and to detect cell viability impact of the test compound against HepG2.2.15 by Cell-titer Blue method. In the experiment, entecavir (ETV) was used as a reference compound to monitor the quality of the experiment.

1.1 Antiviral Experiments

On day 1, the cells were planted into a 96-well plate, the compound was added to treat the cells on day 2, a new culture medium containing the compound was replaced on day 5, and the supernatant was collected on day 8 to extract DNA. Quantitative PCR was used to detect the content of HBV DNA.

Both the test compound and the control compound were diluted in a series of 3 times with 8 concentration points, and 2 replicate wells were measured in parallel. The final concentration of DMSO in the culture medium is 0.5%.

The calculation formula of the inhibition percentage is as follows:

% inh.=(1−HBV copy number of sample/HBV copy number of 0.5% DMSO control)×100

$EC_{50}$ was analyzed by Graphpad Prism software (four parameter logistic equations). 1.2 Cytotoxicity Test (Cell-titer Blue method)

The compound concentration, plate layout, and compound treatment process are consistent with the antiviral experiments. In six days after the cells were treated with the compound, the cell viability was measured with Cell-titer Blue.

Analyze the data and calculate relative cell viability: Use the following formula to calculate the percentage of cell viability:

% Cell viability=(sample fluorescence reading-fluorescence reading of culture medium control)/ (fluorescence reading of DMSO control-fluorescence reading of the culture medium control)× 100.

Finally, GraphPad Prism software was used to calculate the $CC_{50}$ value of the compound.

2. Experimental Results

The anti-hepatitis B virus (HBV) inhibitor of the present invention can inhibit the transcription of the virus so as to achieve the antiviral effect. The content of HBV DNA in the supernatant of HepG2.2.15 cells was detected by real-time fluorescent quantitative PCR (qPCR) method to determine the anti-hepatitis B virus activity of the compound in HepG2.2.15 cells (expressed by $EC_{50}$), and the test compound pair were detected by Cell-titer Blue for HepG2.2.15 cell activity influence (expressed by $CC_{50}$). The following grades were used: For the $EC_{50}$ of anti-hepatitis B virus activity, I:>50 M; II:≤50 M and >5 M; III: ≤5 M and>0.5 M; IV: ≤0.5 M and>0.05 M; V: ≤0.05 M; for the $CC_{50}$ of normal HepG2.2.15 cell viability, use the actual test value or the numerical value expressed in the order of magnitude, for example, ">100 μM" means that the molecule has $CC_{50}$ value for cell activity as greater than the highest concentration tested, and the highest concentration actually used in this test is 100 μM. The results are shown in Table 1. It was reported in the literature that Cpd 7a (Compound 7a in WO 2017/156255 A1) is a highly active anti-hepatitis B virus (HBV) inhibitor and has no significant effect on the activity of normal cells. We use Cpd 7a as a control together with the compound of the present invention in the tests. The compound of the present invention can effectively inhibit the transcription of the virus so as to achieve the antiviral effect without obvious influence on the normal HepG2.2.15 cell activity.

TABLE 1

Anti-hepatitis B virus activity ($EC_{50}$) and HepG2.2.15 cell activity ($CC_{50}$) of some compounds

| Compound | Anti HBV activity ($EC_{50}$) | HepG2.2.15 cell viability $CC_{50}$ (μM) | Compound | Anti HBV activity ($EC_{50}$) | HepG2.2.15 cell viability $CC_{50}$ (μM) |
|---|---|---|---|---|---|
| 1 | III | >100 | 2 | II | 61 |
| 3 | III | >100 | 4 | III | >100 |
| 5 | II | >100 | 6 | II | 82 |
| 7 | I | 29 | 8 | II | >100 |
| 9 | II | >100 | 10 | I | >100 |
| 16 | IV | >100 | 17 | II | >100 |
| 18 | III | >100 | 19 | III | >100 |
| 20 | IV | >100 | 21 | III | >100 |
| 22 | I | >100 | 27 | II | >100 |
| 28 | II | >100 | 29 | IV | >100 |
| 30 | III | >100 | 34 | IV | >100 |
| 35 | III | >100 | 36 | V | >100 |
| 38 | V | >100 | 39 | V | >100 |

TABLE 1-continued

Anti-hepatitis B virus activity (EC$_{50}$) and HepG2.2.15 cell activity (CC$_{50}$) of some compounds

| Compound | Anti HBV activity (EC$_{50}$) | HepG2.2.15 cell viability CC$_{50}$ (μM) | Compound | Anti HBV activity (EC$_{50}$) | HepG2.2.15 cell viability CC$_{50}$ (μM) |
|---|---|---|---|---|---|
| 41 | V | >100 | 42 | II | >100 |
| 43 | II | >100 | 44 | I | 28 |
| 49 | II | 47 | 52 | V | >100 |

TABLE 1-continued

Anti-hepatitis B virus activity (EC$_{50}$) and HepG2.2.15 cell activity (CC$_{50}$) of some compounds

| Compound | Anti HBV activity (EC$_{50}$) | HepG2.2.15 cell viability CC$_{50}$ (μM) | Compound | Anti HBV activity (EC$_{50}$) | HepG2.2.15 cell viability CC$_{50}$ (μM) |
|---|---|---|---|---|---|
| 53 | V | >100 | 54 | V | >100 |
| 55 | V | >100 | 56 | V | >100 |
| 57 | V | >100 | 58 | V | >100 |
| 59 | V | >100 | 60 | V | >100 |
| 62 | V | >100 | 63 | IV | >100 |
| 64 | III | >100 | 66 | IV | >100 |
| 67 | III | >100 | 68 | III | >100 |
| 69 | IV | >100 | 70 | III | >100 |
| 72 | III | >100 | 73 | III | >100 |
| 74 | III | >100 | 77 | V | >100 |
| 78 | V | >100 | 81 | IV | >100 |
| 83 | I | >100 | 85 | III | 96 |
| Cpd 7a | V | >100 | / | / | / |

II. Pharmacokinetics (PK) Experiments

1. Experimental Method

Male SD rats weighing 215-343 grams were fasted overnight before the test. The test compound was completely dissolved in 5% of the total volume of DMSO and then diluted with 30% Captisol to 2 mg/mL, and then it was administered by gavage at dosage of 20 mg/kg. In 15 minutes, 30 minutes, 1, 2, 4, 6, 8 and 24 hours after the administration, blood was taken from the end of the tails of rats at about 0.3 ml at each time point. The blood sample was placed in a centrifuge tube containing K2-EDTA, and centrifuged (@3500 rpm, 10 minutes, 4° C.). Take the plasma and store it in an ultra-low temperature refrigerator at −80° C. 50 μL of plasma sample was mixed with 135 μl of acetonitrile (including the internal standard IS), and then vortexed for 30 s, centrifuged at 15000 rpm at 4° C. for 10 min, and 10 μl of supernatant was taken as sample and injected into LC-MS/MS for analysis.

2. Experimental Results

The Compound 2, Compound 8, Compound 11, Compound 36, and Compound 42 provided by the present invention are well absorbed after oral administration in rats, and the blood exposure is relatively high. The results are shown in FIG. 1 and Table 2. The Tmax of the compound of the present invention was 0.5-1.67 hours, and the Cmax was 3673-9433 ng/ml, which is 2.1-5.3 times the Cmax of the reference compound Cpd 7a; AUC$_{0-24\ h}$ was 17113-87187 ng/ml*h, and was 1.4-7.2 times of the reference compound Cpd 7a AUC$_{0-24\ h}$. Cmax refers to the maximum plasma concentration, T1/2 is the half-life, AUC$_{0-24}$ refers to the area under the 0-24 hour time-concentration curve, and AUC$_{0-inf}$ refers to the area under the 0-Inf time-concentration curve.

TABLE 2

The pharmacokinetics of intragastric administration (20 mg/kg) in rats

| PK Index | Unit | Cpd 7a | Compound 36 | Compound 52 | Compound 53 | Compound 54 |
|---|---|---|---|---|---|---|
| T½ | h | 3.34 | 12.23 | 2.39 | 2.48 | 2.52 |
| Tmax | h | 2.42 | 0.5 | 1.0 | 1.58 | 1.67 |
| Cmax | ng/ml | 1785 | 3730 | 3673.33 | 3933.33 | 9433.33 |
| AUC$_{0-24}$ | ng/ml*h | 11996.94 | 25831.25 | 17113.88 | 26336.03 | 87187.28 |
| AUC$_{0-inf}$ | ng/ml*h | 12101.15 | 32618.03 | 17131.63 | 26395.76 | 87434.77 |

The invention claimed is:

1. A compound, pharmaceutically acceptable salt or stereoisomer thereof, the compound is selected from:

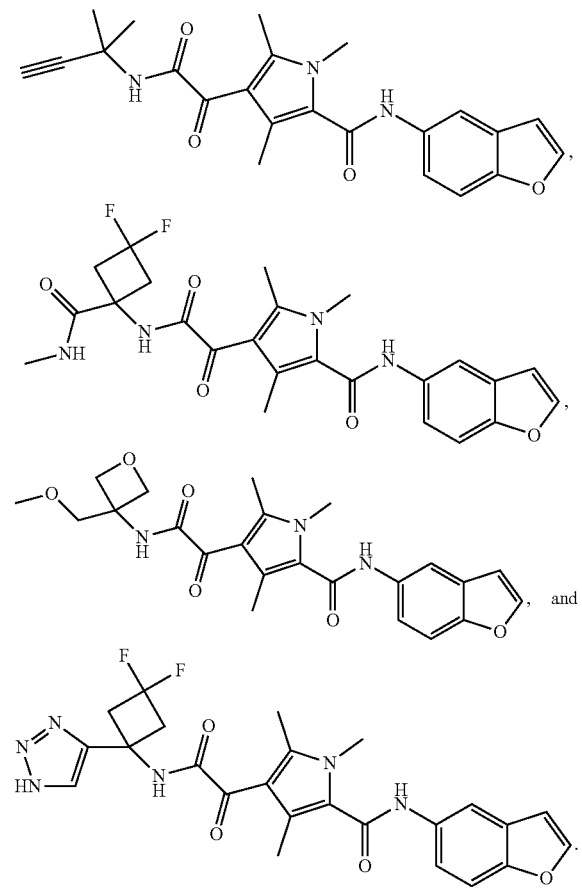 [SMILES: C#CC(C)(C)NC(=O)C(=O)c1c(C)c(C(=O)Nc2ccc3occc3c2)n(C)c1C ; CNC(=O)C1(NC(=O)C(=O)c2c(C)c(C(=O)Nc3ccc4occc4c3)n(C)c2C)CC(F)(F)C1 ; COCC1(NC(=O)C(=O)c2c(C)c(C(=O)Nc3ccc4occc4c3)n(C)c2C)COC1 ; Cc1c(C(=O)C(=O)NC2(c3c[nH]nn3)CC(F)(F)C2)c(C)n(C)c1C(=O)Nc1ccc2occc2c1]

, and

.

2. A pharmaceutical composition, which comprises the compound, pharmaceutically acceptable salt or stereoisomer thereof of claim 1, and pharmaceutically acceptable auxiliary material.

3. The pharmaceutical composition of claim 2, wherein the pharmaceutically acceptable auxiliary material is at least one of excipient, diluent, disintegrant, glidant and lubricant.

4. The pharmaceutical composition of claim 2, which further comprises one or more antiviral agents.

5. The pharmaceutical composition of claim 2, wherein the pharmaceutically acceptable auxiliary material includes dicalcium phosphate, cellulose, compressible sugar, dicalcium phosphate dehydrate, lactose mannitol, microcrystalline cellulose, starch and/or tricalcium phosphate.

6. The pharmaceutical composition of claim 4, wherein the antiviral agent is at least one of hepatitis B virus (HBV) polymerase inhibitor, interferon, virus entry inhibitor, virus maturation inhibitor, assembly regulator, reverse transcriptase inhibitor, and TLR-agonist.

7. The pharmaceutical composition of claim 6, wherein the reverse transcriptase inhibitor is at least one of Entecavir, Tenofovir, HepDirect-Tenofovir, Entricitabine, Adefovir, HepDirect-Adefovir (Pradefovir), Acyclovir, Ganciclovir, GS-7340 (TAF), Bestfovir, Birinapant (HY-16591), Ribavirin and Efavirenz.

8. The pharmaceutical composition of claim 7, wherein the reverse transcriptase inhibitor is Tenofovir.

9. A compound, pharmaceutically acceptable salt or stereoisomer thereof, wherein the compound is selected from:

| Compound No. | Structural Formula |
|---|---|
| 62 | 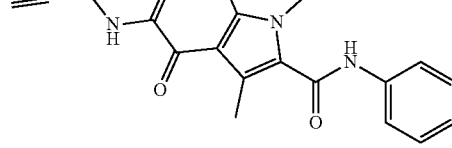 |
| 52 | |
| 53 | |
| 54 | |
| 55 | 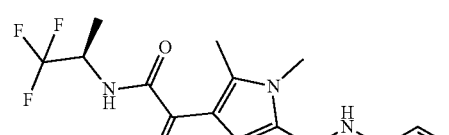 |
| 56 | |
| 57 |  |
| 58 | |
| 59 | |
| 60 | |

| Compound No. | Structural Formula |
|---|---|
| 77 | 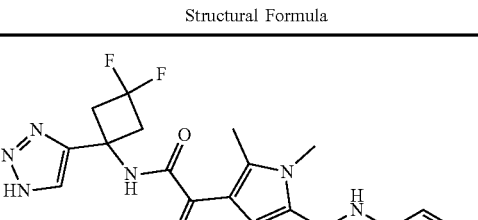 |
| 78 | 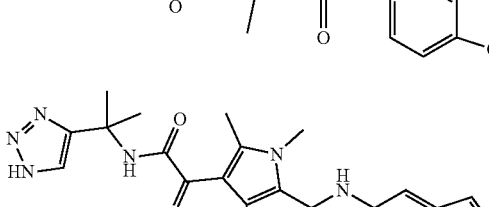 |
10. A method for treating, eradicating, reducing or inhibiting HBV infection or for alleviating liver injury caused by HBV infection, which comprises administering to a patient in need thereof an effective dosage of the compound pharmaceutically acceptable salt or stereoisomer thereof of claim 1.
* * * * *